United States Patent
Mao et al.

(10) Patent No.: US 11,098,315 B2
(45) Date of Patent: Aug. 24, 2021

(54) BIOSYNTHETIC PRODUCTION OF STEVIOL GLYCOSIDES AND PROCESSES THEREFORE

(71) Applicant: Conagen Inc., Bedford, MA (US)

(72) Inventors: Guohong Mao, Burlington, MA (US); Jacob Edward Vick, Cambridge, MA (US); Michael Batten, Westford, MA (US); Yang Luo, Wuxi Jiangsu (CN); Yilin Wu, Wuxi Jiangsu (CN); Beihua Zhang, Wuxi Jiangsu (CN); David Byun, Bedford, MA (US); Xiaodan Yu, Lexington, MA (US)

(73) Assignee: Conagen Inc., Bedford, MA (US)

( * ) Notice: Subject to any disclaimer, the term of this patent is extended or adjusted under 35 U.S.C. 154(b) by 42 days.

(21) Appl. No.: 16/117,652

(22) Filed: Aug. 30, 2018

(65) Prior Publication Data

US 2019/0078102 A1    Mar. 14, 2019

Related U.S. Application Data

(60) Provisional application No. 62/555,809, filed on Sep. 8, 2017, provisional application No. 62/408,179, filed on Oct. 14, 2016.

(51) Int. Cl.

| | | |
|---|---|---|
| *C07H 21/04* | (2006.01) | |
| *C12N 9/10* | (2006.01) | |
| *C12N 9/14* | (2006.01) | |
| *C12N 15/81* | (2006.01) | |
| *C12N 15/82* | (2006.01) | |
| *C12N 15/74* | (2006.01) | |
| *C12N 9/42* | (2006.01) | |
| *A21D 13/062* | (2017.01) | |
| *A23G 4/10* | (2006.01) | |
| *A23L 2/60* | (2006.01) | |
| *A23L 27/30* | (2016.01) | |
| *C12P 19/56* | (2006.01) | |
| *C07H 15/256* | (2006.01) | |
| *C07H 1/00* | (2006.01) | |
| *A23K 20/163* | (2016.01) | |

(52) U.S. Cl.
CPC ........... *C12N 15/81* (2013.01); *A21D 13/062* (2013.01); *A23G 4/10* (2013.01); *A23L 2/60* (2013.01); *A23L 27/36* (2016.08); *C07H 1/00* (2013.01); *C07H 15/256* (2013.01); *C12N 9/1062* (2013.01); *C12N 9/1081* (2013.01); *C12N 9/2445* (2013.01); *C12N 15/74* (2013.01); *C12N 15/8243* (2013.01); *C12N 15/8245* (2013.01); *C12P 19/56* (2013.01); *A23K 20/163* (2016.05); *C12Y 204/01013* (2013.01); *C12Y 204/01028* (2013.01); *C12Y 302/01021* (2013.01)

(58) Field of Classification Search
CPC .. A23L 27/36; A23L 2/60; C12P 19/56; C12P 19/44; C12Y 204/01013; C12Y 302/01021; C12Y 204/01017; C12Y 204/01028; C12N 9/1051; C12N 15/52; C12N 15/74; C12N 15/81
USPC .......................... 536/23.2; 435/320.1, 252.2
See application file for complete search history.

(56) References Cited

U.S. PATENT DOCUMENTS

| | | |
|---|---|---|
| 9,522,929 B2 | 12/2016 | Mao et al. |
| 9,527,880 B2 | 12/2016 | Mao et al. |
| 9,567,619 B2 | 2/2017 | Mao et al. |
| 9,643,990 B2 | 5/2017 | Mao et al. |
| 9,765,104 B2 | 9/2017 | Mao et al. |
| 9,783,566 B2 | 10/2017 | Mao et al. |
| 9,850,270 B2 | 12/2017 | Mao et al. |
| 9,908,913 B2 | 3/2018 | Mao et al. |
| 9,988,414 B2 | 6/2018 | Mao et al. |
| 10,010,099 B2 | 7/2018 | Mao et al. |
| 10,010,101 B2 | 7/2018 | Mao et al. |
| 10,023,604 B2 | 7/2018 | Mao et al. |
| 10,059,732 B2 | 8/2018 | Mao et al. |
| 10,081,826 B2 | 9/2018 | Mao et al. |
| 10,138,263 B2 | 11/2018 | Mao et al. |
| 10,160,781 B2 | 12/2018 | Mao et al. |
| 10,253,344 B2 | 4/2019 | Mao et al. |
| 10,724,062 B2 | 7/2020 | Mao et al. |
| 2011/0091634 A1 | 4/2011 | Abelyan et al. |
| 2016/0095338 A1 | 4/2016 | Mao et al. |
| 2016/0183574 A1 | 6/2016 | Chen et al. |
| 2016/0186225 A1 | 6/2016 | Mikkelsen et al. |
| 2016/0251635 A1 | 9/2016 | Mao et al. |
| 2016/0298159 A1 | 10/2016 | Tao et al. |
| 2017/0362267 A1 | 12/2017 | Mao et al. |
| 2018/0009835 A1 | 1/2018 | Mao et al. |
| 2018/0037600 A1 | 2/2018 | Mao et al. |

(Continued)

FOREIGN PATENT DOCUMENTS

| | | |
|---|---|---|
| WO | WO 2013/026151 A1 | 2/2013 |
| WO | WO 2014/193934 A1 | 12/2014 |

(Continued)

OTHER PUBLICATIONS

Kisselev L., Structure, 2002, vol. 10: 8-9.*
Witkowski et al., Biochemistry 38:11643-11650, 1999.*
Whisstock et al., Quarterly Reviews of Biophysics 2003, vol. 36 (3): 307-340.*
Devos et al., Proteins: Structure, Function and Genetics, 2000, vol. 41: 98-107.*
U.S. Appl. No. 16/382,280, filed Apr. 12, 2019, Mao et al.

(Continued)

*Primary Examiner* — Robert B Mondesi
*Assistant Examiner* — Mohammad Y Meah
(74) *Attorney, Agent, or Firm* — Wolf, Greenfield & Sacks, P.C.; John Keyes

(57) ABSTRACT

The present invention relates to the production of steviol glycoside rebaudiosides D4, WB1 and WB2 and the production of rebaudioside M from Reb D4.

49 Claims, 18 Drawing Sheets

Specification includes a Sequence Listing.

(56) References Cited

U.S. PATENT DOCUMENTS

| | | |
|---|---|---|
| 2018/0057519 A1 | 3/2018 | Mao et al. |
| 2018/0057520 A1 | 3/2018 | Mao et al. |
| 2018/0057521 A1 | 3/2018 | Mao et al. |
| 2018/0057522 A1 | 3/2018 | Mao et al. |
| 2018/0244709 A1 | 8/2018 | Mao et al. |
| 2018/0258124 A1 | 9/2018 | Mao et al. |
| 2018/0258125 A1 | 9/2018 | Mao et al. |
| 2018/0258126 A1 | 9/2018 | Mao et al. |
| 2019/0078102 A1 | 3/2019 | Mao et al. |
| 2019/0345528 A1 | 11/2019 | Mao et al. |

FOREIGN PATENT DOCUMENTS

| | | | |
|---|---|---|---|
| WO | WO 2016/073740 A1 | 11/2015 | |
| WO | WO 2016/043926 A1 | 3/2016 | |
| WO | WO 2016/054540 A1 | 4/2016 | |
| WO | WO 2016/120486 A1 | 8/2016 | |
| WO | WO 2018/164747 A1 | 9/2018 | |

OTHER PUBLICATIONS

PCT/US2017/056457, Jan. 18, 2018, International Search Report and Written Opinion.
PCT/US2017/056457, Apr. 25, 2019, International Preliminary Report on Patentability.
International Search Report and Written Opinion for Application No. PCT/US2017/056457 dated Jan. 18, 2018.
International Preliminary Report on Patentability for Application No. PCT/US2017/056457 dated Apr. 25, 2019.
Talha et al., Analysis of stevioside in Stevia rebaudiana, J. Med. Plants. Mar. 23, 2012; 6(11):2216-2219.
Brandle, J. E. et al., (1998). Stevia Rebaudiana: Its Agricultural, Biological, and Chemical Properties, Canadian J. Slant Science. 78 (4): 527-36.
Ceunen, S., and J.M. C. Geuns, Steviol Glycosides: Chemical Diversity, Metabolism, and Function, J. Nat. Prod., 2013, 76 (6), pp. 1201-1228 (2013).
Du J et al., (2011), Engineering microbial factories for synthesis of value-added products, J Ind Microbiol. Biotechnol. 38: 873-90.
Häusler A, and Münch T., (1997), Microbial production of natural flavors, ASM News 63:551-59.
Prakash I., et al.; Isolation and Characterization of a Novel Rebaudioside M Isomer from a Bioconversion Reaction of Rebaudioside A and NMR Comparison Studies of Rebaudioside M Isolated from Stevia rebaudiana Bertoni and Stevia rebaudiana Morita, Biomolecules, Jun. 2014; 4(2): 374-89. (Published online 2014 Mar. 31, 2014).
Prakash I., et al., Development of Next Generation Stevia Sweetener: Rebaudioside M, Foods, 2014, 3:162-175.
Shockey JM. et al., (2003), *Arabidopsis* contains a large superfamily of acyl-activating enzymes: phylogenetic and biochemical analysis reveals a new class of acyl-coenzyme A synthetases. Plant Physiol 132 1065-76.
U.S. Appl. No. 16/904,797, filed Jun. 18, 2020, Mao et al.
17861012.7, Sep. 4, 2020, Extended European Search Report.

* cited by examiner

SEQUENCE LISTING

```
<160> NUMBER OF SEQ ID NOS: 10

<210> SEQ ID NO 1
<211> LENGTH: 458
<212> TYPE: PRT
<213> ORGANISM: Stevia rebaudiana

<400> SEQUENCE: 1

Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
            35                  40                  45

Asn Phe Asn Lys Pro Lys Thr Ser Asn Tyr Pro His Phe Thr Phe Arg
        50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
                100                 105                 110

Glu Glu Asp Glu Glu Val Ser Cys Leu Ile Thr Asp Ala Leu Trp Tyr
            115                 120                 125

Phe Ala Gln Ser Val Ala Asp Ser Leu Asn Leu Arg Arg Leu Val Leu
        130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190
```

```
Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
                260                 265                 270

Pro Ser Ser Val Leu Tyr Val Ser Phe Gly Ser Thr Ser Glu Val Asp
                275                 280                 285

Glu Lys Asp Phe Leu Glu Ile Ala Arg Gly Leu Val Asp Ser Lys Gln
            290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
                340                 345                 350

Phe Trp Thr His Ser Gly Trp Asn Ser Thr Leu Glu Ser Val Cys Glu
                355                 360                 365

Gly Val Pro Met Ile Phe Ser Asp Phe Gly Leu Asp Gln Pro Leu Asn
            370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
                420                 425                 430

Lys Ala Asp Val Ser Leu Met Lys Gly Gly Ser Ser Tyr Glu Ser Leu
            435                 440                 445

Glu Ser Leu Val Ser Tyr Ile Ser Ser Leu
        450                 455

<210> SEQ ID NO 2
<211> LENGTH: 1377
<212> TYPE: DNA
<213> ORGANISM: Stevia rebaudiana

<400> SEQUENCE: 2
atggagaata agacagaaac aaccgtaaga cggaggcgga ggattatctt gttccctgta     60
ccatttcagg gccatattaa tccgatcctc aattagcaa acgtcctcta ctccaaggga    120
ttttcaataa caatcttcca tactaacttt aacaagccta aaacgagtaa ttatcctcac    180
tttacattca ggttcattct agacaacgac cctcaggatg agcgtatctc aaatttacct    240
acgcatggcc ccttggcagg tatgcgaata ccaataatca tgagcatgg agccgatgaa    300 ctccgtcgcg agttagagct tctcatgctc gcaagtgagg aagacgagga agtttcgtgc    360
ctaataactg atgcgctttg gtacttcgcc caatcagtcg cagactcact gaatctacgc    420
cgtttggtcc ttatgacaag ttcattattc aactttcacg cacatgtatc actgccgcaa    480
tttgacgagt tgggttacct ggacccggat gacaaaacgc gattggagga caagcgtcg    540 ggcttcccca tgctgaaagt caaagatatt aagagcgctt atagtaattg gcaaattctg    600
```

```
aaagaaattc tcggaaaaat gataaagcaa accaaagcgt cctctggagt aatctggaac    660
tccttcaagg agttagagga atctgaactt gaaacggtca tcagagaaat ccccgctccc    720
tcgttcttaa ttccactacc caagcacctt actgcaagta gcagttccct cctagatcat    780
gaccgaaccg tgtttcagtg gctggatcag caaccccgt cgtcagttct atatgtaagc    840
tttgggagta cttcggaagt ggatgaaaag gacttcttag agattgcgcg agggctcgtg    900
gatagcaaac agagcttcct gtgggtagtg agaccgggat cgttaaggg ctcgacgtgg    960 gtcgagccgt tgccagatgg ttttctaggg gagagaggga gaatcgtgaa atgggttcca    1020
cagcaagagg ttttggctca cggagctata ggggcctttt ggacccactc tggttggaat    1080
tctactcttg aaagtgtctg tgaaggcgtt ccaatgatat tttctgattt tgggcttgac    1140
cagcctctaa acgctcgcta tatgtctgat gtgttgaagg ttggcgtgta cctggagaat    1200
ggttgggaaa gggggggaaat tgccaacgcc atacgccggg taatggtgga cgaggaaggt    1260
gagtacatac gtcagaacgc tcgggtttta aaacaaaaag cggacgtcag ccttatgaag    1320
ggaggtagct cctatgaatc cctagaatcc ttggtaagct atatatcttc gttataa       1377
```

<210> SEQ ID NO 3
<211> LENGTH: 458
<212> TYPE: PRT
<213> ORGANISM: Stevia rebaudiana

<400> SEQUENCE: 3

```
Met Asn Trp Gln Ile Leu Lys Glu Ile Leu Gly Lys Met Ile Lys Gln
1               5                   10                  15

Thr Lys Ala Ser Ser Gly Val Ile Trp Asn Ser Phe Lys Glu Leu Glu
            20                  25                  30

Glu Ser Glu Leu Glu Thr Val Ile Arg Glu Ile Pro Ala Pro Ser Phe
        35                  40                  45

Leu Ile Pro Leu Pro Lys His Leu Thr Ala Ser Ser Ser Leu Leu
    50                  55                  60

Asp His Asp Arg Thr Val Phe Gln Trp Leu Asp Gln Gln Pro Pro Ser
65                  70                  75                  80

Ser Val Leu Tyr Val Ser Phe Gly Ser Thr Ser Glu Val Asp Glu Lys
                85                  90                  95

Asp Phe Leu Glu Ile Ala Arg Gly Leu Val Asp Ser Lys Gln Ser Phe
            100                 105                 110

Leu Trp Val Val Arg Pro Gly Phe Val Lys Gly Ser Thr Trp Val Glu
        115                 120                 125

Pro Leu Pro Asp Gly Phe Leu Gly Glu Arg Gly Arg Ile Val Lys Trp
    130                 135                 140

Val Pro Gln Gln Glu Val Leu Ala His Gly Ala Ile Gly Ala Phe Trp
145                 150                 155                 160

Thr His Ser Gly Trp Asn Ser Thr Leu Glu Ser Val Cys Glu Gly Val
                165                 170                 175

Pro Met Ile Phe Ser Asp Phe Gly Leu Asp Gln Pro Leu Asn Ala Arg
            180                 185                 190

Tyr Met Ser Asp Val Leu Lys Val Gly Val Tyr Leu Glu Asn Gly Trp
        195                 200                 205

Glu Arg Gly Glu Ile Ala Asn Ala Ile Arg Arg Val Met Val Asp Glu
    210                 215                 220

Glu Gly Glu Tyr Ile Arg Gln Asn Ala Arg Val Leu Lys Gln Lys Ala
225                 230                 235                 240
```

```
Asp Val Ser Leu Met Lys Gly Gly Ser Ser Tyr Glu Ser Leu Glu Ser
            245                 250                 255

Leu Val Ser Tyr Ile Ser Ser Leu Glu Asn Lys Thr Glu Thr Thr Val
            260                 265                 270

Arg Arg Arg Arg Ile Ile Leu Phe Pro Val Pro Phe Gln Gly His
            275                 280                 285

Ile Asn Pro Ile Leu Gln Leu Ala Asn Val Leu Tyr Ser Lys Gly Phe
            290                 295                 300

Ser Ile Thr Ile Phe His Thr Asn Phe Asn Lys Pro Lys Thr Ser Asn
305                 310                 315                 320

Tyr Pro His Phe Thr Phe Arg Phe Ile Leu Asp Asn Asp Pro Gln Asp
                325                 330                 335

Glu Arg Ile Ser Asn Leu Pro Thr His Gly Pro Leu Ala Gly Met Arg
            340                 345                 350

Ile Pro Ile Ile Asn Glu His Gly Ala Asp Glu Leu Arg Arg Glu Leu
            355                 360                 365

Glu Leu Leu Met Leu Ala Ser Glu Glu Asp Glu Val Ser Cys Leu
        370                 375                 380

Ile Thr Asp Ala Leu Trp Tyr Phe Ala Gln Ser Val Ala Asp Ser Leu
385                 390                 395                 400

Asn Leu Arg Arg Leu Val Leu Met Thr Ser Ser Leu Phe Asn Phe His
                405                 410                 415

Ala His Val Ser Leu Pro Gln Phe Asp Glu Leu Gly Tyr Leu Asp Pro
            420                 425                 430

Asp Asp Lys Thr Arg Leu Glu Glu Gln Ala Ser Gly Phe Pro Met Leu
            435                 440                 445

Lys Val Lys Asp Ile Lys Ser Ala Tyr Ser
            450                 455

<210> SEQ ID NO 4
<211> LENGTH: 1377
<212> TYPE: DNA
<213> ORGANISM: Stevia rebaudiana

<400> SEQUENCE: 4
atgaactggc aaatcctgaa agaaatcctg ggtaaaatga tcaaacaaac caaagcgtcg      60
tcgggcgtta tctggaactc cttcaaagaa ctggaagaat cagaactgga aaccgttatt     120
cgcgaaatcc cggctccgtc gttcctgatt ccgctgccga acatctgac cgcgagcagc      180 agcagcctgc tggatcacga ccgtacggtc tttcagtggc tggatcagca accgccgtca     240
tcggtgctgt atgtttcatt cggtagcacc tctgaagtcg atgaaaaaga ctttctggaa     300
atcgctcgcg gctggtggta gtaaacag tccttcctgt gggtggttcg tccgggtttt      360
gtgaaaggca gcacgtgggt tgaaccgctg ccggatggct tcctgggtga acgcggccgt     420
attgtcaaat gggtgccgca gcaagaagtg ctggcacatg gtgctatcgg cgcgttttgg     480
acccactctg gttggaacag tacgctggaa tccgtttgcg aaggtgtccc gatgattttc     540
agcgattttg gcctggacca gccgctgaat gcccgctata tgtctgatgt tctgaaagtc     600
ggtgtgtacc tggaaaacgg ttgggaacgt ggcgaaattg cgaatgccat ccgtcgcgtt     660
atggtcgatg aagaaggcga atacattcgc cagaacgctc gtgtcctgaa acaaaaagcg     720
gacgtgagcc tgatgaaagg cggtagctct tatgaatcac tggaatcgct ggttagctac     780
atcagttccc tggaaaataa aaccgaaacc acggtgcgtc gccgtcgccg tattatcctg     840
```

```
ttcccggttc cgtttcaggg tcatattaac ccgatcctgc aactggcgaa tgttctgtat    900
tcaaaaggct tttcgatcac catcttccat acgaacttca acaaaccgaa aaccagtaac    960
tacccgcact ttacgttccg ctttattctg gataacgacc cgcaggatga acgtatctcc   1020
aatctgccga cccacggccc gctggccggt atgcgcattc cgattatcaa tgaacacggt   1080
gcagatgaac tgcgccgtga actggaactg ctgatgctgg ccagtgaaga agatgaagaa   1140
gtgtcctgtc tgatcaccga cgcactgtgg tatttcgccc agagcgttgc agattctctg   1200
aacctgcgcc gtctggtcct gatgacgtca tcgctgttca atttcatgc gcacgtttct    1260 ctgccgcaat tgatgaact gggctacctg gacccggatg acaaaaccccg tctggaagaa    1320 caagccagtg gttttccgat gctgaaagtc aaagacatta aatccgccta ttcgtaa      1377
```

<210> SEQ ID NO 5
<211> LENGTH: 839
<212> TYPE: PRT
<213> ORGANISM: Pichia pastoris

<400> SEQUENCE: 5

```
Met Thr Gln Leu Asp Val Glu Ser Leu Ile Gln Glu Leu Thr Leu Asn
1               5                   10                  15

Glu Lys Val Gln Leu Leu Ser Gly Ser Asp Phe Trp His Thr Thr Pro
            20                  25                  30

Val Arg Arg Leu Gly Ile Pro Lys Met Arg Leu Ser Asp Gly Pro Asn
        35                  40                  45

Gly Val Arg Gly Thr Lys Phe Phe Asn Gly Val Pro Thr Ala Cys Phe
    50                  55                  60

Pro Cys Gly Thr Gly Leu Gly Ala Thr Phe Asp Lys Glu Leu Leu Lys
65                  70                  75                  80

Glu Ala Gly Ser Leu Met Ala Asp Glu Ala Lys Ala Lys Ala Ala Ser
                85                  90                  95

Val Val Leu Gly Pro Thr Ala Asn Ile Ala Arg Gly Pro Asn Gly Gly
            100                 105                 110

Arg Gly Phe Glu Ser Phe Gly Glu Asp Pro Val Val Asn Gly Leu Ser
        115                 120                 125

Ser Ala Ala Met Ile Asn Gly Leu Gln Gly Lys Tyr Ile Ala Ala Thr
    130                 135                 140

Met Lys His Tyr Val Cys Asn Asp Leu Glu Met Asp Arg Asn Cys Ile
145                 150                 155                 160

Asp Ala Gln Val Ser His Arg Ala Leu Arg Glu Val Tyr Leu Leu Pro
                165                 170                 175

Phe Gln Ile Ala Val Arg Asp Ala Asn Pro Arg Ala Ile Met Thr Ala
            180                 185                 190

Tyr Asn Lys Ala Asn Gly Glu His Val Ser Gln Ser Lys Phe Leu Leu
        195                 200                 205

Asp Glu Val Leu Arg Lys Glu Trp Gly Trp Asp Gly Leu Leu Met Ser
    210                 215                 220

Asp Trp Phe Gly Val Tyr Asp Ala Lys Ser Ser Ile Thr Asn Gly Leu
225                 230                 235                 240

Asp Leu Glu Met Pro Gly Pro Pro Gln Cys Arg Val His Ser Ala Thr
                245                 250                 255

Asp His Ala Ile Asn Ser Gly Glu Ile His Ile Asn Asp Val Asp Glu
            260                 265                 270

Arg Val Arg Ser Leu Leu Ser Leu Ile Asn Tyr Cys His Gln Ser Gly
        275                 280                 285
```

```
Val Thr Glu Glu Asp Pro Thr Ser Asp Asn Asn Thr Pro Glu Thr
    290             295                 300
Ile Glu Lys Leu Arg Lys Ile Ser Arg Glu Ser Ile Val Leu Leu Lys
305                 310                 315                 320
Asp Asp Asp Arg Asn Arg Ser Ile Leu Pro Leu Lys Lys Ser Asp Lys
                    325                 330                 335
Ile Ala Val Ile Gly Asn Asn Ala Lys Gln Ala Ala Tyr Cys Gly Gly
                340                 345                 350
Gly Ser Ala Ser Val Leu Ser Tyr His Thr Thr Pro Phe Asp Ser
        355                 360                 365
Ile Lys Ser Arg Leu Glu Asp Ser Asn Thr Pro Ala Tyr Thr Ile Gly
    370                 375                 380
Ala Asp Ala Tyr Lys Asn Leu Pro Pro Leu Gly Pro Gln Met Thr Asp
385                 390                 395                 400
Ser Asp Gly Lys Pro Gly Phe Asp Ala Lys Phe Val Gly Ser Pro
                405                 410                 415
Thr Ser Lys Asp Arg Lys Leu Ile Asp His Phe Gln Leu Thr Asn Ser
                420                 425                 430
Gln Val Phe Leu Val Asp Tyr Tyr Asn Glu Gln Ile Pro Glu Asn Lys
        435                 440                 445
Glu Phe Tyr Val Asp Val Glu Gly Gln Phe Ile Pro Glu Glu Asp Gly
    450                 455                 460
Thr Tyr Asn Phe Gly Leu Thr Val Phe Gly Thr Gly Arg Leu Phe Val
465                 470                 475                 480
Asp Asp Lys Leu Val Ser Asp Ser Ser Gln Asn Gln Thr Pro Gly Asp
                485                 490                 495
Ser Phe Phe Gly Leu Ala Ala Gln Glu Val Ile Gly Ser Ile His Leu
                500                 505                 510
Val Lys Gly Lys Ala Tyr Lys Ile Lys Val Leu Tyr Gly Ser Ser Val
        515                 520                 525
Thr Arg Thr Tyr Glu Ile Ala Ala Ser Val Ala Phe Glu Gly Gly Ala
    530                 535                 540
Phe Thr Phe Gly Ala Ala Lys Gln Arg Asn Glu Asp Glu Glu Ile Ala
545                 550                 555                 560
Arg Ala Val Glu Ile Ala Lys Ala Asn Asp Lys Val Val Leu Cys Ile
                565                 570                 575
Gly Leu Asn Gln Asp Phe Glu Ser Glu Gly Phe Asp Arg Pro Asp Ile
                580                 585                 590
Lys Ile Pro Gly Ala Thr Asn Lys Met Val Ser Ala Val Leu Lys Ala
        595                 600                 605
Asn Pro Asn Thr Val Ile Val Asn Gln Thr Gly Thr Pro Val Glu Met
    610                 615                 620
Pro Trp Ala Ser Asp Ala Pro Val Ile Leu Gln Ala Trp Phe Gly Gly
625                 630                 635                 640
Ser Glu Ala Gly Thr Ala Ile Ala Asp Val Leu Phe Gly Asp Tyr Asn
                645                 650                 655
Pro Ser Gly Lys Leu Thr Val Thr Phe Pro Leu Arg Phe Glu Asp Asn
                660                 665                 670
Pro Ala Tyr Leu Asn Phe Gln Ser Asn Lys Gln Ala Cys Trp Tyr Gly
        675                 680                 685
Glu Asp Val Tyr Val Gly Tyr Arg Tyr Tyr Glu Thr Ile Asp Arg Pro
    690                 695                 700
```

Val Leu Phe Pro Phe Gly His Gly Leu Ser Phe Thr Glu Phe Asp Phe
705                 710                 715                 720

Thr Asp Met Phe Val Arg Leu Glu Glu Glu Asn Leu Glu Val Glu Val
            725                 730                 735

Val Val Arg Asn Thr Gly Lys Tyr Asp Gly Ala Glu Val Val Gln Leu
        740                 745                 750

Tyr Val Ala Pro Val Ser Pro Ser Leu Lys Arg Pro Ile Lys Glu Leu
    755                 760                 765

Lys Glu Tyr Ala Lys Ile Phe Leu Ala Ser Gly Ala Lys Thr Val
770                 775                 780

His Leu Ser Val Pro Ile Lys Tyr Ala Thr Ser Phe Phe Asp Glu Tyr
785                 790                 795                 800

Gln Lys Lys Trp Cys Ser Glu Lys Gly Glu Tyr Thr Ile Leu Leu Gly
                805                 810                 815

Ser Ser Ser Ala Asp Ile Lys Val Ser Gln Ser Ile Thr Leu Glu Lys
                820                 825                 830

Thr Thr Phe Trp Lys Gly Leu
        835

<210> SEQ ID NO 6
<211> LENGTH: 2520
<212> TYPE: DNA
<213> ORGANISM: Pichia pastoris

<400> SEQUENCE: 6

```
atgacccaac tggatgtgga gagcctgatt caagagctga ccctgaacga aaaggtgcaa      60
ctgctgagcg gtagcgactt ctggcatacc accccggttc gtcgtctggg catcccgaag     120
atgcgtctga gcgacggtcc gaacggcgtt cgtggtacca aattctttaa cggtgttccg     180
accgcgtgct tcccgtgcgg taccggtctg ggcgcgacct tgacaaagga actgctgaaa     240
gaggcgggta gcctgatggc ggatgaagcg aaagcgaaag cggcgagcgt ggttctgggt     300
ccgaccgcga acattgcgcg tggtccgaac ggtggccgtg gcttcgagag cttcggcgag     360
gacccggtgg ttaacggtct gagcagcgcg gcgatgatca acggcctgca gggcaagtac     420
attgcggcga ccatgaaaca ctatgtttgc aacgatctgg aaatggaccg taactgcatt     480
gacgcgcaag ttagccaccg tgcgctgcgt gaggtgtacc tgctgccgtt ccaaatcgcg     540
gtgcgtgatg cgaacccgcg tgcgattatg accgcgtata caaggcgaa cggcgaacac     600
gttagccaga gcaaattcct gctggacgaa gtgctgcgta aggagtgggg ctgggatggt     660
ctgctgatga gcgactggtt tggtgtttac gatgcgaaaa gcagcatcac caacggcctg     720
gacctggaga tgccgggtcc gccgcagtgc cgtgtgcaca gcgcgaccga tcacgcgatc     780
aacagcggcg aaatccacat taacgatgtt gacgagcgtg tgcgtagcct gctgagcctg     840
attaactact gccaccaaag cggtgttacc gaggaagatc cggaaaccag cgacaacaac     900
acccccggaaa ccatcgagaa gctgcgtaaa atcagccgtg agagcattgt gctgctgaag     960
gacgatgacc gtaaccgtag cattctgccg ctgaagaaaa gcgacaaaat cgcggttatt    1020
ggtaacaacg cgaaacaagc ggcgtattgc ggtggcggta gcgcgagcgt gctgagctat    1080
cacaccacca ccccgttcga cagcatcaag agccgtctgg aagatagcaa caccccggcg    1140
tacaccattg gtgcggacgc gtataaaaac ctgccgccgc tgggtccgca aatgaccgat    1200
agcgacggca gccggggttt tgatgcgaaa ttctttgttg cagcccgac cagcaaggat    1260
cgtaaactga tcgaccactt ccagctgacc aacagccaag tttttctggt ggactactat    1320
```

-continued

```
aacgaacaga tcccggaaaa caaggagttc tacgttgacg tggagggtca atttattccg    1380
gaggaagatg gcacctataa cttcggtctg accgtgtttg gtaccggccg tctgttcgtt    1440
gatgacaaac tggttagcga cagcagccag aaccaaaccc cgggcgatag cttctttggt    1500
ctggcggcgc aggaagtgat cggcagcatt cacctggtga agggtaaagc gtacaagatc    1560
aaagttctgt atggcagcag cgtgacccgt acctacgaaa ttgcggcgag cgttgcgttt    1620
gagggcggtg cgttcacctt tggtgcggcg aaacagcgta acgaagacga ggaaatcgcg    1680
cgtgcggtgg agattgcgaa ggcgaacgac aaagtggttc tgtgcatcgg cctgaaccaa    1740
gatttcgaaa gcgagggttt tgatcgtccg gacatcaaga ttccgggcgc gaccaacaaa    1800
atggttagcg cggtgctgaa ggcgaacccg aacaccgtta ttgtgaacca gaccggtacc    1860
ccggttgaga tgccgtgggc gagcgatgcg ccggtgatcc tgcaagcgtg gtttggcggt    1920
agcgaggcgg gtaccgcgat gcggatgttt ctgtttggcg actacaaccc gagcggcaag    1980
ctgaccgtga ccttcccgct gcgttttgag gataacccgg cgtacctgaa cttccagagc    2040
aacaaacaag cgtgctggta tggcgaagac gtttacgtgg gttatcgtta ctatgagacc    2100
atcgatcgtc cggtgctgtt cccgtttggt cacggcctga gcttcaccga gttcgatttt    2160
accgacatgt ttgttcgtct ggaggaagag aacctggaag ttgaggtggt tgtgcgtaac    2220
accggcaagt acgacggtgc ggaagtggtg cagctgtatg ttgcgccggt tagcccgagc    2280
ctgaaacgtc cgatcaagga actgaaagag tacgcgaaaa ttttcctggc gagcggtgaa    2340
gcgaagaccg ttcacctgag cgtgccgatc aaatacgcga ccagcttctt tgatgagtat    2400
caaaagaaat ggtgcagcga aaagggcgag tataccattc tgctgggtag cagcagcgcg    2460
gacatcaaag ttagccaaag catcaccctg gaaaaaacca ccttctggaa aggtctgtaa    2520
```

<210> SEQ ID NO 7
<211> LENGTH: 481
<212> TYPE: PRT
<213> ORGANISM: Stevia rebaudiana

<400> SEQUENCE: 7

```
Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
                20                  25                  30

Leu Leu His His Lys Gly Leu Gln Ile Thr Phe Val Asn Thr Asp Phe
            35                  40                  45

Ile His Asn Gln Phe Leu Glu Ser Ser Gly Pro His Cys Leu Asp Gly
        50                  55                  60

Ala Pro Gly Phe Arg Phe Glu Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
                100                 105                 110

Pro Pro Thr Cys Ile Ile Ser Asp Gly Phe Leu Ser Val Phe Thr Ile
            115                 120                 125

Asp Ala Ala Lys Lys Leu Gly Ile Pro Val Met Met Tyr Trp Thr Leu
        130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
```

```
                    165                 170                 175
Leu Asp Thr Val Ile Asp Trp Val Pro Gly Met Glu Gly Ile Arg Leu
            180                 185                 190

Lys Asp Phe Pro Leu Asp Trp Ser Thr Asp Leu Asn Asp Lys Val Leu
            195                 200                 205

Met Phe Thr Thr Glu Ala Pro Gln Arg Ser His Lys Val Ser His His
            210                 215                 220

Ile Phe His Thr Phe Asp Glu Leu Glu Pro Ser Ile Ile Lys Thr Leu
225                 230                 235                 240

Ser Leu Arg Tyr Asn His Ile Tyr Thr Ile Gly Pro Leu Gln Leu Leu
            245                 250                 255

Leu Asp Gln Ile Pro Glu Glu Lys Lys Gln Thr Gly Ile Thr Ser Leu
            260                 265                 270

His Gly Tyr Ser Leu Val Lys Glu Glu Pro Glu Cys Phe Gln Trp Leu
            275                 280                 285

Gln Ser Lys Glu Pro Asn Ser Val Val Tyr Val Asn Phe Gly Ser Thr
            290                 295                 300

Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
            325                 330                 335

Gly Glu Asn Ala Val Leu Pro Pro Glu Leu Glu Glu His Ile Lys Lys
            340                 345                 350

Arg Gly Phe Ile Ala Ser Trp Cys Ser Gln Glu Lys Val Leu Lys His
            355                 360                 365

Pro Ser Val Gly Gly Phe Leu Thr His Cys Gly Trp Gly Ser Thr Ile
            370                 375                 380

Glu Ser Leu Ser Ala Gly Val Pro Met Ile Cys Trp Pro Tyr Ser Trp
385                 390                 395                 400

Asp Gln Leu Thr Asn Cys Arg Tyr Ile Cys Lys Glu Trp Glu Val Gly
            405                 410                 415

Leu Glu Met Gly Thr Lys Val Lys Arg Asp Glu Val Lys Arg Leu Val
            420                 425                 430

Gln Glu Leu Met Gly Glu Gly Gly His Lys Met Arg Asn Lys Ala Lys
            435                 440                 445

Asp Trp Lys Glu Lys Ala Arg Ile Ala Ile Ala Pro Asn Gly Ser Ser
            450                 455                 460

Ser Leu Asn Ile Asp Lys Met Val Lys Glu Ile Thr Val Leu Ala Arg
465                 470                 475                 480

Asn

<210> SEQ ID NO 8
<211> LENGTH: 1446
<212> TYPE: DNA
<213> ORGANISM: Stevia rebaudiana

<400> SEQUENCE: 8
atggacgcta tggccacgac cgaaaagaaa ccgcacgtta tctttattcc gttcccggca      60
cagagtcaca tcaaggctat gctgaagctg gcccaactgc tgcatcacaa aggcctgcaa     120
attacctttg tgaacacgga tttcatccat aatcagtttc tggaaagctc tggccgcac     180 tgcctggatg gtcgccgggg ttttcgcttc gaaaccatcc ggatggtgt ctcgcatagc     240 ccggaagcct ctattccgat ccgtgaatcg ctgctgcgca gcattgaaac caactttctg     300
```

```
gatcgtttca tcgacctggt gacgaaactg ccggacccgc cgacgtgcat tatctccgac      360
ggctttctgt cagttttcac cattgatgcg gccaaaaagc tgggtatccc ggtcatgatg      420
tattggacgc tggcagcttg tggctttatg ggtttctacc atattcactc actgatcgaa      480
aaaggctttg caccgctgaa ggatgctagt tatctgacca acggctatct ggataccggtc     540 attgactggg tgccgggcat ggaaggtatc cgtctgaaag atttcccgct ggactggagc      600
accgatctga atgacaaagt gctgatgttt accacggaag cgccgcagcg ctctcataaa      660
gttagtcatc acattttca caccttcgat gaactggaac cgtcgattat caaaaccctg       720
agcctgcgtt ataatcatat ttacaccatt ggcccgctgc aactgctgct ggaccaaatc      780
ccggaagaaa agaaacaaac cggcatcacg tcgctgcacg ttatagccct ggtgaaagaa      840
gaaccggaat gcttccagtg gctgcaatct aaggaaccga cagtgtggt ttacgtgaat        900 tttggttcca ccacggttat gtcactggaa gatatgaccg aatttggctg gggtctggca      960
aactctaacc attattttct gtggatcatc cgtagtaacc tggtcattgg cgaaaatgca     1020
gtgctgccgc cggaactgga agaacacatt aaaaagcgcg gtttcatcgc ttcctggtgt     1080
tcacaggaaa aagttctgaa gcatccgtcc gtcggcggtt ttctgaccca ctgcggctgg     1140
ggtagcacga ttgaatctct gagtgctggt gttccgatga tttgctggcc gtatagctgg     1200
gatcaactga ccaactgccg ctacatctgt aaagaatggg aagtcggcct ggaaatgggt     1260
acgaaagtga agcgtgacga agttaaacgc ctggtccaag aactgatggg cgaaggcggt     1320
cataaaatgc gtaacaaagc gaaggattgg aaagaaaagg cccgcattgc gattgcgccg     1380
aacggcagca gcagcctgaa cattgacaaa atggtgaagg aaatcaccgt tctggcgcgt     1440
aattaa                                                                1446
```

<210> SEQ ID NO 9
<211> LENGTH: 459
<212> TYPE: PRT
<213> ORGANISM: Hordeum vulgare

<400> SEQUENCE: 9

```
Met Asp Gly Asn Ser Ser Ser Pro Leu His Val Val Ile Cys Pro
1               5                   10                  15

Trp Leu Ala Leu Gly His Leu Leu Pro Cys Leu Asp Ile Ala Glu Arg
            20                  25                  30

Leu Ala Ser Arg Gly His Arg Val Ser Phe Val Ser Thr Pro Arg Asn
        35                  40                  45

Ile Ala Arg Leu Pro Pro Leu Arg Pro Ala Val Ala Pro Leu Val Asp
    50                  55                  60

Phe Val Ala Leu Pro Leu Pro His Val Asp Gly Leu Pro Glu Gly Ala
65                  70                  75                  80

Glu Ser Thr Asn Asp Val Pro Tyr Asp Lys Phe Glu Leu His Arg Lys
                85                  90                  95

Ala Phe Asp Gly Leu Ala Ala Pro Phe Ser Glu Phe Leu Arg Ala Ala
            100                 105                 110

Cys Ala Glu Gly Ala Gly Ser Arg Pro Asp Trp Leu Ile Val Asp Thr
        115                 120                 125

Phe His His Trp Ala Ala Ala Ala Val Glu Asn Lys Val Pro Cys
    130                 135                 140

Val Met Leu Leu Leu Gly Ala Ala Thr Val Ile Ala Gly Phe Ala Arg
145                 150                 155                 160

Gly Val Ser Glu His Ala Ala Ala Ala Val Gly Lys Glu Arg Pro Ala
```

```
                    165                 170                 175
Ala Glu Ala Pro Ser Phe Glu Thr Glu Arg Arg Lys Leu Met Thr Thr
                180                 185                 190

Gln Asn Ala Ser Gly Met Thr Val Ala Glu Arg Tyr Phe Leu Thr Leu
            195                 200                 205

Met Arg Ser Asp Leu Val Ala Ile Arg Ser Cys Ala Glu Trp Glu Pro
        210                 215                 220

Glu Ser Val Ala Ala Leu Thr Thr Leu Ala Gly Lys Pro Val Val Pro
225                 230                 235                 240

Leu Gly Leu Leu Pro Pro Ser Pro Glu Gly Gly Arg Gly Val Ser Lys
                245                 250                 255

Glu Asp Ala Ala Val Arg Trp Leu Asp Ala Gln Pro Ala Lys Ser Val
            260                 265                 270

Val Tyr Val Ala Leu Gly Ser Glu Val Pro Leu Arg Ala Glu Gln Val
        275                 280                 285

His Glu Leu Ala Leu Gly Leu Glu Leu Ser Gly Ala Arg Phe Leu Trp
    290                 295                 300

Ala Leu Arg Lys Pro Thr Asp Ala Pro Asp Ala Ala Val Leu Pro Pro
305                 310                 315                 320

Gly Phe Glu Glu Arg Thr Arg Gly Arg Gly Leu Val Val Thr Gly Trp
                325                 330                 335

Val Pro Gln Ile Gly Val Leu Ala His Gly Ala Val Ala Ala Phe Leu
            340                 345                 350

Thr His Cys Gly Trp Asn Ser Thr Ile Glu Gly Leu Leu Phe Gly His
        355                 360                 365

Pro Leu Ile Met Leu Pro Ile Ser Ser Asp Gln Gly Pro Asn Ala Arg
    370                 375                 380

Leu Met Glu Gly Arg Lys Val Gly Met Gln Val Pro Arg Asp Glu Ser
385                 390                 395                 400

Asp Gly Ser Phe Arg Arg Glu Asp Val Ala Ala Thr Val Arg Ala Val
                405                 410                 415

Ala Val Glu Glu Asp Gly Arg Arg Val Phe Thr Ala Asn Ala Lys Lys
            420                 425                 430

Met Gln Glu Ile Val Ala Asp Gly Ala Cys His Glu Arg Cys Ile Asp
        435                 440                 445

Gly Phe Ile Gln Gln Leu Arg Ser Tyr Lys Ala
    450                 455

<210> SEQ ID NO 10
<211> LENGTH: 1380
<212> TYPE: DNA
<213> ORGANISM: Hordeum vulgare

<400> SEQUENCE: 10
atggatggta actcctcctc ctcgccgctg catgtggtca tttgtccgtg gctggctctg      60
ggtcacctgc tgccgtgtct ggatattgct gaacgtctgg cgtcacgcgg ccatcgtgtc     120
agttttgtgt ccaccccgcg caacattgcc cgtctgccgc cgctgcgtcc ggctgttgca     180
ccgctggttg atttcgtcgc actgccgctg ccgcatgttg acgtctgcc ggagggtgcg     240 gaatcgacca tgatgtgcc gtatgacaaa tttgaactgc accgtaaggc gttcgatggt     300
ctggcggccc cgtttagcga atttctgcgt gcagcttgcg cagaaggtgc aggttctcgc     360
ccggattggc tgattgtgga cacctttcat cactgggcgg cggcggcggc ggtggaaaac     420
aaagtgccgt gtgttatgct gctgctgggt gcagcaacgg tgatcgctgg tttcgcgcgt     480
```

```
ggtgttagcg aacatgcggc ggcggcggtg ggtaaagaac gtccggctgc ggaagccccg    540
agttttgaaa ccgaacgtcg caagctgatg accacgcaga atgcctccgg catgaccgtg    600
gcagaacgct atttcctgac gctgatgcgt agcgatctgg ttgccatccg ctcttgcgca    660
gaatgggaac cggaaagcgt ggcagcactg accacgctgg caggtaaacc ggtggttccg    720
ctgggtctgc tgccgccgag tccggaaggc ggtcgtggcg tttccaaaga agatgctgcg    780
gtccgttggc tggacgcaca gccggcaaag tcagtcgtgt acgtcgcact gggttcggaa    840
gtgccgctgc gtgcggaaca agttcacgaa ctggcactgg gcctggaact gagcggtgct    900
cgctttctgt gggcgctgcg taaaccgacc gatgcaccgg acgccgcagt gctgccgccg    960
ggtttcgaag aacgtacccg cggccgtggt ctggttgtca cgggttgggt gccgcagatt   1020
ggcgttctgc tcatggtgc ggtggctgcg tttctgaccc actgtggctg gaactctacg   1080
atcgaaggcc tgctgttcgg tcatccgctg attatgctgc cgatcagctc tgatcagggt   1140
ccgaatgcgc gcctgatgga aggccgtaaa gtcggtatgc aagtgccgcg tgatgaatca   1200
gacggctcgt ttcgtcgcga agatgttgcc gcaaccgtcc gcgccgtggc agttgaagaa   1260
gacggtcgtc gcgtcttcac ggctaacgcg aaaaagatgc aagaaattgt ggccgatggc   1320
gcatgccacg aacgttgtat tgacggtttt atccagcaac tgcgcagtta caaggcgtga   1380
```

BIOSYNTHETIC PRODUCTION OF STEVIOL GLYCOSIDES AND PROCESSES THEREFORE

CROSS-REFERENCE TO RELATED APPLICATIONS

This application claims priority to U.S. Provisional Application No. 62/408,179, filed on Oct. 14, 2016, and U.S. Provisional Application No. 62/555,809, filed on Sep. 8, 2017, the contents of each of which are incorporated by reference herein in their entirety.

FIELD OF THE INVENTION

The field of the invention relates to methods and processes useful in the production of specific steviol glycosides. More specifically, the present disclosure provides for the production of a previously unknown rebaudioside, rebaudioside D4 ("Reb D4") that can then be converted to rebaudioside M ("Reb M") via enzymatic conversion. The present disclosure also provides for production of previously unknown rebaudiosides, rebaudioside WB1 ("Reb WB1") and rebaudioside WB2 ("Reb WB2").

BACKGROUND OF THE INVENTION

The present disclosure is focused on the production of novel steviosides Reb D4, Reb WB1 and Reb WB2 and on conversion of Reb D4 to Reb M. In particular, the present disclosure relates to the synthesis of Reb D4 and its consequent use in the production of Reb M.

Steviol glycosides are natural products isolated from *Stevia rebaudiana* leaves, and are widely used as high intensity, low-caloric sweeteners in food, feed and beverages. Naturally occurring steviol glycosides have the same base diterpene structure (steviol) but differ in the number and structure of carbohydrate residue modifications (e.g. glucose, rhamnose, and xylose residues) at the C13 and C19 positions of the steviol backbone. Steviol glycosides with known structures include stevioside, rebaudioside A, rebaudioside B, rebaudioside C, rebaudioside D, rebaudioside E, rebaudioside F, rebaudioside M and dulcoside A. In terms of commercial utilization rebaudioside M itself has been generally regarded as safe (GRAS' status).

On dry weight basis, stevioside, rebaudioside A, rebaudioside C, and dulcoside A, account for 9.1, 3.8, 0.6, and 0.30 percent of the total weight of the steviol glycosides in wild type *Stevia* leaves, respectively, while the other steviol glucosides, such as Reb M are present in significantly lower amounts. Extracts from *Stevia rebaudiana* plant are commercially available, where such extracts typically contain stevioside and rebaudioside A as the primary components. The other known steviol glycosides typically are present in the *stevia* extract as minor or trace components. For example, the amount of rebaudioside A in commercial preparations can vary from about 20% to more than 90% of the total steviol glycoside content, while the amount of rebaudioside B is typically about 1-2%, the amount of rebaudioside C can be about 7-15%, and the amount of rebaudioside D can be about 2% of the total steviol glycosides. In such extracts rebaudioside M is present only in vanishingly small amounts. Interestingly, Rebaudioside E is also one of the least abundant steviol glycosides present in *Stevia rebaudiana* plant varieties, accounting for less than 0.5% of total glycosides.

As natural sweeteners, different steviol glycosides have different degrees of sweetness, 'mouth feel' and specific after-tastes associated with each rebaudioside species tested. Relative to table sugar (i.e., "sucrose") the sweetness of steviol glycosides is significantly higher. For example, stevioside is 100-150 times sweeter than sucrose but has a bitter after-taste as noted in taste tests, while rebaudiosides A and E are 250-450 times sweeter than sucrose and the after-taste is much better than stevioside, however, a noticeable after-taste is still present. Accordingly, the taste profiles of any *stevia* extracts are profoundly affected by the relative content of the steviol glycosides in the extract, which in turn may are affected by the environmental conditions experienced by the underlying plants and the extraction process used. These variations in plant production, weather conditions and extraction conditions can lead to inconsistent compositions of the steviol glycosides in the *stevia* extracts, such that the taste profile varies strongly among different batches of extraction products.

The taste profile of *stevia* extracts also can be affected by plant-derived or environment-derived contaminants (such as pigments, lipids, proteins, phenolics and saccharides) that remain in the product after the extractions process. These contaminants typically have their own off-flavors undesirable for the use of the *stevia* extract as a sweetener in consumer products. In addition, the cost of isolating individual or specific combinations of steviol rebaudiosides that are not abundant in *stevia* extracts is cost and resource prohibitive. Given that there is a limited quality and availability of some specific steviol glycosides, commercial supply can be better addressed by bio-conversion, where natural enzymes, or specific microbes can be modified to carry needed enzymes and use commercially significant fermentation processes to specifically increase the production of glycosides of interest. For example, bio-conversion of stevioside to Reb E has been reported previously (see, e.g., PCT Application Publication Nos. WO/2015/065650 and WO/2015/171555) using enzymes obtained from modified microbes. Alternatively, other non-biologic synthetic means can be used to develop steviol glycosides of interest.

From a biological perspective all steviol glycosides are formed by a series of glycosylation reactions of steviol, which typically are catalyzed by UDP-glycosyltransferase (UGT) enzymes using uridine 5'-diphosphoglucose (UDP-glucose) as a donor of the sugar moiety. In plants, UGTs are a very divergent group of enzymes that transfer a glucose residue from UDP-glucose to steviol. In these reactions stevioside is often an intermediate in the biosynthesis of various rebaudioside compounds. For example, glycosylation of stevioside at the C-3' at the C-13-O-glucose of stevioside yields rebaudioside A; while glycosylation at the C-2' at the 19-O-glucose position of stevioside yields rebaudioside E.

As described herein, specific and directed glycosylation of rebaudioside E (at the C-19-O-glucose) can produce rebaudioside Reb D4 and further glycosylation of Reb D4 by UGT enzymes produces rebaudioside M. However, until the instant disclosure the synthetic steps for the production of D4 enzymatically had not been reported.

According to the current disclosure, a practical approach to improve the taste quality of *stevia* extracts is to increase the yield of those rebaudioside compounds that have more desirable taste characteristics in general and to do this via a more productive synthetic pathway. Of those steviol glycosides tested many believe that Reb M has the most desirable taste and chemical characteristics for use in food and beverages. As stated above, however, the plant has vanishingly small amounts of this compound present in its leaves and therefore an alternative biosynthetic needs to be developed for the large-scale production of this glycoside as well as to provide alternate sweeteners to the food and beverage industry.

Accordingly, there is a need for steviol glycosides with better and more consistent taste profiles to be developed as commercial products and for such steviol glycosides to utilize a relative common starting substrate, such as more abundant steviol glycosides as starting molecule, so that such production of desirable glycosides can be commercially as cost effective as possible. The present disclosure provides a method of producing rebaudioside M from a previously unknown steviol glycoside, Reb D4, as well as methods for producing Reb D4, Reb WB1 and Reb WB2.

Going further, the extraction process from plants, typically employs solid-liquid extraction techniques using solvents like hexane, chloroform, and ethanol for steviol glycoside recovery (Catchpole et al., 2003). However, solvent extraction is itself energy intensive, leads to problems of toxic waste disposal, requires extensive acreage for the plants themselves to be grown and yields a product that requires further purification for minor constituents to be recovered. Thus, new production methods are also needed to reduce costs of steviol glycoside production and lessen the environmental impact of large scale cultivation and processing (Yao et al., 1994). One such potential solution is the use of fermentation bio-conversion technology that allows the production in certain microbial species that increases the selectivity, abundance and purity of desired steviol glycosides available for commerce.

In addition to the above, while consumers approve and actively seek natural and biological sources for food, feed, flavor or medicinal components they are also concerned about sourcing, consistent taste profile and environmentally sustainable production. Into this situation the microbial fermentation and production methods of the current disclosure provide Reb M in quantities useful for a variety of industries and research while doing so in a more natural fashion than inorganic synthesis or current plant extraction techniques.

Accordingly, a need exists for the development of a novel method of producing Reb M economically and conveniently to further enable human and animal consumption.

SUMMARY OF THE INVENTION

Aspects of the disclosure relate to steviol glycosides, methods of producing the steviol glycosides, and compositions comprising the steviol glycosides. In some aspects, the present disclosure encompasses methods of producing Reb M from previously unreported steviol glycoside Reb D4.

In particular, the current disclosure provides for the production of steviol glycoside rebaudioside D4 "Reb D4" which is identified as (13-[(2-O-β-D-glucopyranosyl-β-D-glucopyranosyl)oxy] ent-kaur-16-en-19-oic acid-[(2-O-β-D-glucopyranosyl-3-O-β-D-glucopyranosyl-(3-D-glucopyranosyl) ester]) and its conversion to Reb M by a specific UDP-glycosyltransferase (See FIG. 1). The present disclosure also provides for the production of Reb WB1 and Reb WB2 as described herein.

The current methods described herein provide an approach for the synthesis of specific steviol glycosides using synthetic pathways.

An alternative embodiment is producing rebaudioside D4 from rebaudioside W utilizing a pathway through RebWB1.

A further embodiment is producing rebaudioside M from rebaudioside D4.

In one embodiment of the current disclosure, a method is provided that allows for the production of Reb M using a pathway through Reb WB2, Reb WB1 and Reb D4.

In an alternative embodiment, beta glucosidase is used to catalyze the enzymatic bioconversion of Reb W to Reb WB1, see FIG. 14.

In some aspects, the disclosure provides a steviol glycoside Reb D4 having the structure:

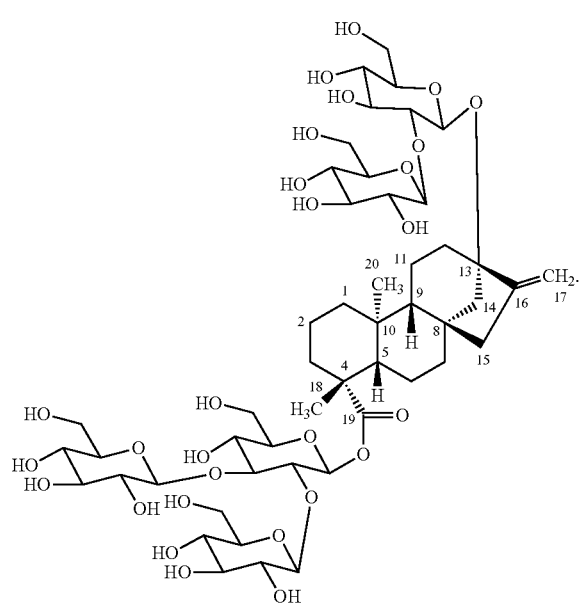

In some embodiments, the disclosure provides a composition comprising Reb D4, optionally wherein said Reb D4 content in the composition is at least 70% (e.g., at least 70%, at least 75%, at least 80%, at least 85%, at least 90%, at least 95%, at least 95%, at least 97%, at least 98%, at least 99% or 100%) pure. In some embodiments, the disclosure provides a consumable product comprising a sweetening amount of Reb D4. In some embodiments, the consumable product is selected from the group consisting of beverages, confectioneries, bakery products, cookies, and chewing gums.

In other aspects, the disclosure provides a composition comprising a mixture of Reb D4 and Reb M. In some embodiments, the disclosure provides a consumable product comprising a sweetening amount of a mixture of Reb D4 and Reb M. In some embodiments, the consumable product is selected from the group consisting of beverages, confectioneries, bakery products, cookies, and chewing gums.

In yet other aspects, the disclosure provides a steviol glycoside Reb WB1 having the structure:

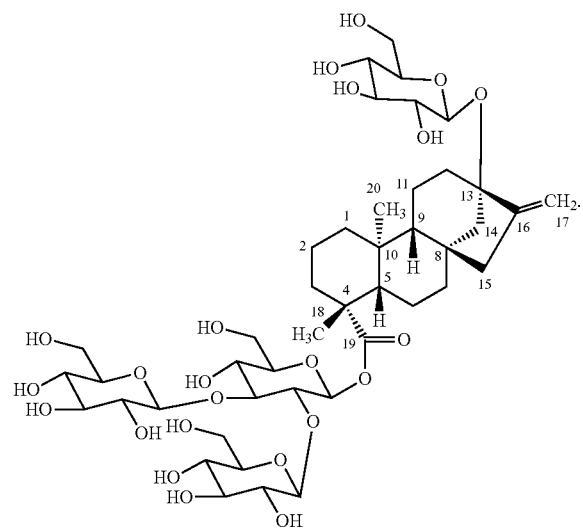

In some embodiments, the disclosure provides a composition comprising Reb WB1, optionally wherein said Reb WB1 content in the composition is at least 70% (e.g., at least 70%, at least 75%, at least 80%, at least 85%, at least 90%, at least 95%, at least 95%, at least 97%, at least 98%, at least 99% or 100%) pure. In some embodiments, the disclosure provides a consumable product comprising a sweetening amount of Reb WB1. In some embodiments, the consumable product is selected from the group consisting of beverages, confectioneries, bakery products, cookies, and chewing gums.

In yet other aspects, the disclosure provides a steviol glycoside Reb WB2 having the structure:

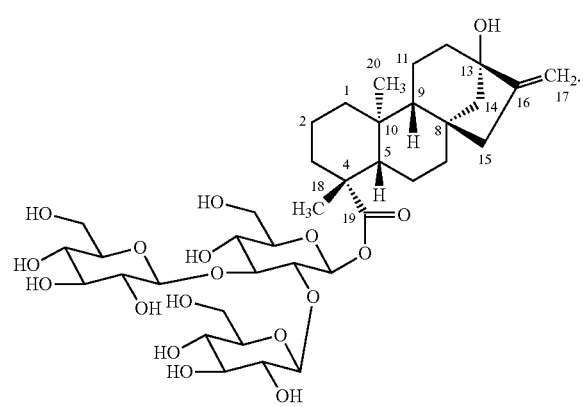

In some embodiments, the disclosure provides a composition comprising Reb WB2, optionally wherein said Reb WB2 content in the composition is at least 70% (e.g., at least 70%, at least 75%, at least 80%, at least 85%, at least 90%, at least 95%, at least 95%, at least 97%, at least 98%, at least 99% or 100%) pure. In some embodiments, the disclosure provides a consumable product comprising a sweetening amount of Reb WB2. In some embodiments, the consumable product is selected from the group consisting of beverages, confectioneries, bakery products, cookies, and chewing gums.

In some aspects, the disclosure provides a steviol glycoside of interest produced by a transformed cellular system growing within a medium. In some embodiments, said transformed cellular system is selected from the group consisting of: yeast, non-steviol glycoside producing plants, algae and bacteria. In some embodiments, said cellular system is a bacteria and is selected from the group consisting of *Escherichia; Salmonella; Bacillus; Acinetobacter; Streptomyces; Corynebacterium; Methylosinus; Methylomonas; Rhodococcus; Pseudomonas; Rhodobacter; Synechocystis; Saccharomyces; Zygosaccharomyces; Kluyveromyces; Candida; Hansenula; Debaryomyces; Mucor; Pichia; Torulopsis; Aspergillus; Arthrobotlys; Brevibacteria; Microbacterium; Arthrobacter; Citrobacter; Escherichia; Klebsiella; Pantoea; Salmonella Corynebacterium; Clostridium;* and *Clostridium acetobutylicum.* In some embodiments, said cellular system is *E. Coli.* In some embodiments, said steviol glycoside is Reb D4. In some embodiments, said steviol glycoside is Reb WB1. In some embodiments, said steviol glycoside is Reb WB2. In some embodiments, the source material is steviol. In some embodiments, said steviol glycoside content is at least 70% pure. In some embodiments, the method of production further comprises: i) purifying a crude product; and, ii) removing solvents under vacuum to provide a concentrated product. In some embodiments, said crude product is purified by column chromatography. In some embodiments, said crude product is purified by acid-base extraction. In some embodiments, said crude product is purified by vacuum distillation. In some embodiments, the method of production further comprises purifying said steviol glycoside using a semi-preparative HPLC. In other aspects, the disclosure provides a consumable product comprising a sweetening amount of the steviol glycoside. In some embodiments, the consumable product is selected from the group consisting of beverages, confectioneries, bakery products, cookies, and chewing gums.

In other aspects, the disclosure provides a CP1 recombinant polypeptide comprising a DNA sequence having at least 80% (e.g., at least 80%, at least 85%, at least 90%, at least 95%, at least 95%, at least 97%, at least 98%, at least 99% or 100%) identity to SEQ ID NO:3. In some embodiments, the amino acid sequence of the CP1 recombinant polypeptide has at least 80% (e.g., at least 80%, at least 85%, at least 90%, at least 95%, at least 95%, at least 97%, at least 98%, at least 99% or 100%) identity to SEQ ID NO:4. In some embodiments, the CP1 recombinant polypeptide has one or more mutations at one or more positions listed in Table 2.

In yet other aspects, the disclosure provides a biosynthetic method of making a steviol glycoside of interest comprising expressing an CP1 enzyme in a transformed cellular system; growing the cellular system in a medium containing a substrate; and producing the steviol glycoside of interest. In some embodiments, the method further comprises incubating a recombinant sucrose synthase with the substrate. In some embodiments, the method further comprises incubating a recombinant UDP glycosyltransferase UGT85C2 with the sucrose synthase, the substrate, and the CP1 recombinant polypeptide. In some embodiments, the method further comprises adding a beta glucosidase enzyme to the reaction mixture. In some embodiments, the sucrose synthase is selected from the group consisting of an *Arabidopsis* sucrose synthase 1, an *Arabidopsis* sucrose synthase 3 and a *Vigna radiate* sucrose synthase. In some embodiments, the sucrose synthase is an *Arabidopsis thaliana* sucrose synthase 1. In some embodiments, the steviol glycosides produced are a mixture of Reb D4 and Reb M. In some embodiments, the method further comprises: i) purifying a crude product; and, ii) removing solvents under vacuum to provide a concentrated product. In some embodiments, said crude product is purified by column chromatography. In some embodiments, said crude product is purified by acid-base extraction. In some embodiments, said crude product is purified by vacuum distillation. In some embodiments, the method further comprises purifying said steviol glycoside using a semi-preparative HPLC. In some embodiments, said steviol glycoside is Reb WB1. In some embodiments, said steviol glycoside is Reb WB2. In some embodiments, said steviol glycoside is Reb D4. In some embodiments, said steviol glycoside is Reb M. In some embodiments, the method further comprises the use of HV1 (SEQ ID NO:9). In some embodiments, the method further comprises the use of UGT76G1 (SEQ ID NO:1).

In other aspects, the disclosure provides a method of producing rebaudioside M, comprising cultivating a recombinant cell under suitable growth conditions where said recombinant cell exhibits the ability to produce steviol glycosides, the method comprising contacting said recombinant cell with a reaction composition containing stevioside, sucrose synthase and sucrose; wherein said recombinant cell expresses a first UDP-glycosyltransferase (UGT) or a catalytically active portion thereof capable of using said stevioside substrate to produce rebaudioside E; wherein said recombinant cell expresses a second UDP-glycosyltransferase (UGT) or a catalytically active portion thereof capable of using said Rebaudioside E to produce rebaudioside D4; and, wherein said recombinant cell expresses a third UDP-glycosyltransferase (UGT) or a catalytically active portion thereof capable of using said Rebaudioside D4 to produce rebaudioside M. In some embodiments, the method further comprises a sucrose synthase gene or a catalytically active portion thereof being expressed in said recombinant cell. In some embodiments, the method further comprises a sucrose synthase being added to the reaction composition.

In some aspects, the disclosure provides Reb M produced by a method described in the above paragraph or as otherwise disclosed herein.

In other aspects, the disclosure provides a recombinant cell that expresses a biosynthetic pathway for producing Reb M (e.g., through conversion of Reb D4 to Reb M or through conversion of Reb E to Reb D4 to Reb M). In some embodiments, the cell expresses one or more of a first UDP-glycosyltransferase (UGT) or a catalytically active portion thereof capable of using said stevioside substrate to produce rebaudioside E, a second UDP-glycosyltransferase (UGT) or a catalytically active portion thereof capable of using said Rebaudioside E to produce rebaudioside D4, and a third UDP-glycosyltransferase (UGT) or a catalytically active portion thereof capable of using said Rebaudioside D4 to produce rebaudioside M. In some embodiments, the cell is a yeast cell. In some embodiments, the cell is a bacterial cell. In some embodiments, the cell is a plant cell.

In other aspects, the disclosure provides a method of producing Reb M using the enzymes and substrates described in FIG. 14, or a subset thereof (e.g., starting with Reb W, Reb WB1, or Reb D4 and/or utilizing UGT76G1, CP1 or CR1). In some embodiments, the Reb M is produced using an in vitro reaction mixture containing the enzymes and substrates described in FIG. 14, or a subset thereof (e.g., starting with Reb W, Reb WB1, or Reb D4 and/or utilizing UGT76G1, CP1 or CR1). In some embodiments, the Reb M is produced in vivo in a cell that expresses the enzymes described in FIG. 14, or a subset thereof (e.g., UGT76G1, CP1 or CR1), wherein the cell is incubated with a substrate described in FIG. 14 (e.g., Reb W, Reb WB1, or Reb D4). In some embodiments, the cell is a yeast cell. In some embodiments, the cell is a bacterial cell. In some embodiments, the cell is a plant cell.

In terms of product/commercial utility there are several dozen products containing steviol glycosides on the market in the United States and can be used in everything from analgesics to pest repellents as well as in foods and as a dietary supplement. Products containing steviol glycosides can be aerosols, liquids, or granular formulations.

As for the cellular system in the embodiment, in some embodiments, it is selected from the group consisting of bacteria, yeast, and a combination thereof, or any cellular system that would allow the genetic transformation with the selected genes and thereafter the biosynthetic production of the desired steviol glycosides from steviol. In a most preferred microbial system, E. coli are used to produce the desired steviol glycoside compounds.

While the disclosure is susceptible to various modifications and alternative forms, specific embodiments thereof are shown by way of example in the drawing and will herein be described in detail. It should be understood, however, that the drawings and detailed description presented herein are not intended to limit the disclosure to the particular embodiment disclosed, but on the contrary, the intention is to cover all modifications, equivalents, and alternatives falling within the spirit and scope of the present disclosure as defined by the appended claims.

Other features and advantages of this invention will become apparent in the following detailed description of preferred embodiments of this invention, taken with reference to the accompanying drawings.

DETAILED DESCRIPTION OF CERTAIN EMBODIMENTS THE INVENTION

Explanation of Terms Used Herein

Figure 1:
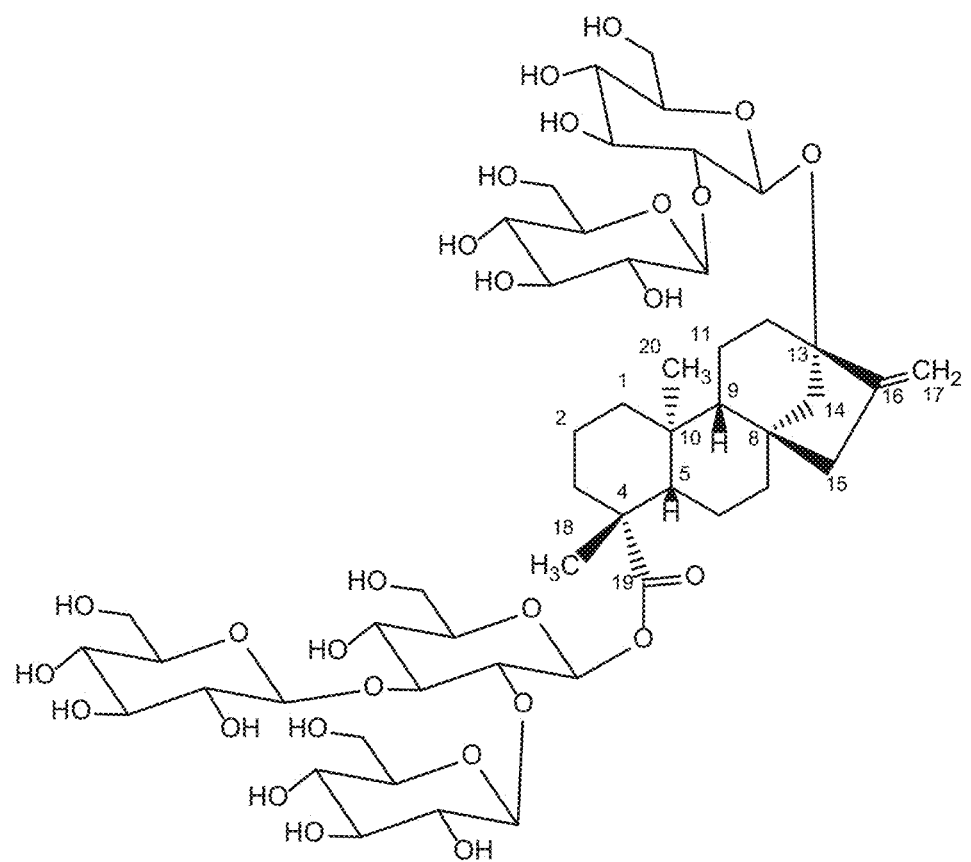
FIG. 1. Shows the structure of rebaudioside D4 (13-[(2-O-β-D-glucopyranosyl-β-D-glucopyranosyl)oxy] ent-kaur-16-en-19-oic acid-[(2-O-β-D-glucopyranosyl-3-O-β-D-glucopyranosyl-β-D-glucopyranosyl) ester]).

Steviol Glycosides are a class of chemical compounds responsible for the sweet taste of the leaves of the South American plant *Stevia rebaudiana* (Asteraceae), and can be used as sweeteners in food, feed and beverages.

Definitions

"Cellular system" is any cells that provide for the expression of ectopic proteins. It included bacteria, yeast, plant cells and animal cells. It includes both prokaryotic and eukaryotic cells. It also includes the in vitro expression of proteins based on cellular components, such as ribosomes.

"Coding sequence" is to be given its ordinary and customary meaning to a person of ordinary skill in the art, and is used without limitation to refer to a DNA sequence that encodes for a specific amino acid sequence.

"Growing the Cellular System". Growing includes providing an appropriate medium that would allow cells to multiply and divide. It also includes providing resources so that cells or cellular components can translate and make recombinant proteins.

"Protein Expression". Protein production can occur after gene expression. It consists of the stages after DNA has been transcribed to messenger RNA (mRNA). The mRNA is then translated into polypeptide chains, which are ultimately folded into proteins. DNA is present in the cells through transfection—a process of deliberately introducing nucleic acids into cells. The term is often used for non-viral methods in eukaryotic cells. It may also refer to other methods and cell types, although other terms are preferred: "transformation" is more often used to describe non-viral DNA transfer in bacteria, non-animal eukaryotic cells, including plant cells. In animal cells, transfection is the preferred term as transformation is also used to refer to progression to a cancerous state (carcinogenesis) in these cells. Transduction is often used to describe virus-mediated DNA transfer. Transformation, transduction, and viral infection are included under the definition of transfection for this application.

"Yeast". According to the current disclosure a yeast as claimed herein are eukaryotic, single-celled microorganisms classified as members of the fungus kingdom. Yeasts are unicellular organisms which evolved from multicellular ancestors but with some species useful for the current disclosure being those that have the ability to develop multicellular characteristics by forming strings of connected budding cells known as pseudo hyphae or false hyphae.

"UGT Enzymes". The names of the UGT enzymes used in the present disclosure are consistent with the nomenclature system adopted by the UGT Nomenclature Committee (Mackenzie et al., "*The UDP glycosyltransferase gene super family: recommended nomenclature updated based on evolutionary divergence*," PHARMACOGENETICS, 1997, vol. 7, pp. 255-269), which classifies the UGT genes by the combination of a family number, a letter denoting a subfamily, and a number for an individual gene. For example, the name "UGT76G1" refers to a UGT enzyme encoded by a gene belonging to UGT family number 76 (which is of plant origin), subfamily G, and gene number 1.

Structural Terms

As used herein, the singular forms "a, an" and "the" include plural references unless the content clearly dictates otherwise.

To the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

The term "complementary" is to be given its ordinary and customary meaning to a person of ordinary skill in the art, and is used without limitation to describe the relationship between nucleotide bases that are capable to hybridizing to one another. For example, with respect to DNA, adenosine is complementary to thymine and cytosine is complementary to guanine. Accordingly, the subjection technology also includes isolated nucleic acid fragments that are complementary to the complete sequences as reported in the accompanying Sequence Listing as well as those substantially similar nucleic acid sequences The terms "nucleic acid" and "nucleotide" are to be given their respective ordinary and customary meanings to a person of ordinary skill in the art, and are used without limitation to refer to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified or degenerate variants thereof (e.g., degenerate codon substitutions) and complementary sequences, as well as the sequence explicitly indicated.

The term "isolated" is to be given its ordinary and customary meaning to a person of ordinary skill in the art, and when used in the context of an isolated nucleic acid or an isolated polypeptide, is used without limitation to refer to a nucleic acid or polypeptide that, by the hand of man, exists apart from its native environment and is therefore not a product of nature. An isolated nucleic acid or polypeptide can exist in a purified form or can exist in a non-native environment such as, for example, in a transgenic host cell.

The terms "incubating" and "incubation" as used herein means a process of mixing two or more chemical or biological entities (such as a chemical compound and an enzyme) and allowing them to interact under conditions favorable for producing a steviol glycoside composition.

The term "degenerate variant" refers to a nucleic acid sequence having a residue sequence that differs from a reference nucleic acid sequence by one or more degenerate codon substitutions. Degenerate codon substitutions can be achieved by generating sequences in which the third position of one or more selected (or all) codons is substituted with mixed base and/or deoxyinosine residues. A nucleic acid sequence and all of its degenerate variants will express the same amino acid or polypeptide.

The terms "polypeptide," "protein," and "peptide" are to be given their respective ordinary and customary meanings to a person of ordinary skill in the art; the three terms are sometimes used interchangeably, and are used without limitation to refer to a polymer of amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein," "polypeptide," and "peptide" are used interchangeably herein when referring to a polynucleotide product. Thus, exemplary polypeptides include polynucleotide products, naturally occurring proteins, homologs, orthologs, paralogs, fragments and other equivalents, variants, and analogs of the foregoing.

The terms "polypeptide fragment" and "fragment," when used in reference to a reference polypeptide, are to be given their ordinary and customary meanings to a person of ordinary skill in the art, and are used without limitation to refer to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both.

The term "functional fragment" of a polypeptide or protein refers to a peptide fragment that is a portion of the full length polypeptide or protein, and has substantially the same biological activity, or carries out substantially the same function as the full length polypeptide or protein (e.g., carrying out the same enzymatic reaction).

The terms "variant polypeptide," "modified amino acid sequence" or "modified polypeptide," which are used interchangeably, refer to an amino acid sequence that is different from the reference polypeptide by one or more amino acids, e.g., by one or more amino acid substitutions, deletions, and/or additions. In an aspect, a variant is a "functional variant" which retains some or all of the ability of the reference polypeptide.

The term "functional variant" further includes conservatively substituted variants. The term "conservatively substituted variant" refers to a peptide having an amino acid sequence that differs from a reference peptide by one or more conservative amino acid substitutions, and maintains some or all of the activity of the reference peptide. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. Such substitutions are expected to have little or no effect on the apparent molecular weight or isoelectric point of the protein or polypeptide. The phrase "conservatively substituted variant" also includes peptides wherein a residue is replaced with a chemically-derivatized residue, provided that the resulting peptide maintains some or all of the activity of the reference peptide as described herein.

The term "variant," in connection with the polypeptides of the subject technology, further includes a functionally active polypeptide having an amino acid sequence at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, and even 100% identical to the amino acid sequence of a reference polypeptide.

The term "homologous" in all its grammatical forms and spelling variations refers to the relationship between polynucleotides or polypeptides that possess a "common evolutionary origin," including polynucleotides or polypeptides from super families and homologous polynucleotides or proteins from different species (Reeck et al., CELL 50:667, 1987). Such polynucleotides or polypeptides have sequence homology, as reflected by their sequence similarity, whether in terms of percent identity or the presence of specific amino acids or motifs at conserved positions. For example, two homologous polypeptides can have amino acid sequences that are at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 900 at least 91%, at least 92%, at least 93%, at least 94%, at least 95%, at least 96%, at least 97%, at least 98%, at least 99%, and even 100% identical.

"Suitable regulatory sequences" is to be given its ordinary and customary meaning to a person of ordinary skill in the art, and is used without limitation to refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" is to be given its ordinary and customary meaning to a person of ordinary skill in the art, and is used without limitation to refer to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters, which cause a gene to be expressed in most cell types at most times, are commonly referred to as "constitutive promoters." It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression" as used herein, is to be given its ordinary and customary meaning to a person of ordinary skill in the art, and is used without limitation to refer to the transcription and stable accumulation of sense (mRNA) or antisense RNA derived from the nucleic acid fragment of the subject technology. "Over-expression" refers to the production of a gene product in transgenic or recombinant organisms that exceeds levels of production in normal or non-transformed organisms.

"Transformation" is to be given its ordinary and customary meaning to a person of reasonable skill in the field, and is used without limitation to refer to the transfer of a polynucleotide into a target cell for further expression by that cell. The transferred polynucleotide can be incorporated into the genome or chromosomal DNA of a target cell, resulting in genetically stable inheritance, or it can replicate independent of the host chromosomal. Host organisms containing the transformed nucleic acid fragments are referred to as "transgenic" or "recombinant" or "transformed" organisms.

The terms "transformed," "transgenic," and "recombinant," when used herein in connection with host cells, are to be given their respective ordinary and customary meanings to a person of ordinary skill in the art, and are used without limitation to refer to a cell of a host organism, such as a plant or microbial cell, into which a heterologous nucleic acid molecule has been introduced. The nucleic acid molecule can be stably integrated into the genome of the host cell, or the nucleic acid molecule can be present as an extrachromosomal molecule. Such an extrachromosomal molecule can be auto-replicating. Transformed cells, tissues, or subjects are understood to encompass not only the end product of a transformation process, but also transgenic progeny thereof.

The terms "recombinant," "heterologous," and "exogenous," when used herein in connection with polynucleotides, are to be given their ordinary and customary meanings to a person of ordinary skill in the art, and are used without limitation to refer to a polynucleotide (e.g., a DNA sequence or a gene) that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found.

Similarly, the terms "recombinant," "heterologous," and "exogenous," when used herein in connection with a polypeptide or amino acid sequence, means a polypeptide or amino acid sequence that originates from a source foreign to the particular host cell or, if from the same source, is modified from its original form. Thus, recombinant DNA segments can be expressed in a host cell to produce a recombinant polypeptide.

The terms "plasmid," "vector," and "cassette" are to be given their respective ordinary and customary meanings to a person of ordinary skill in the art, and are used without limitation to refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

DETAILED DESCRIPTION

Figure 14:
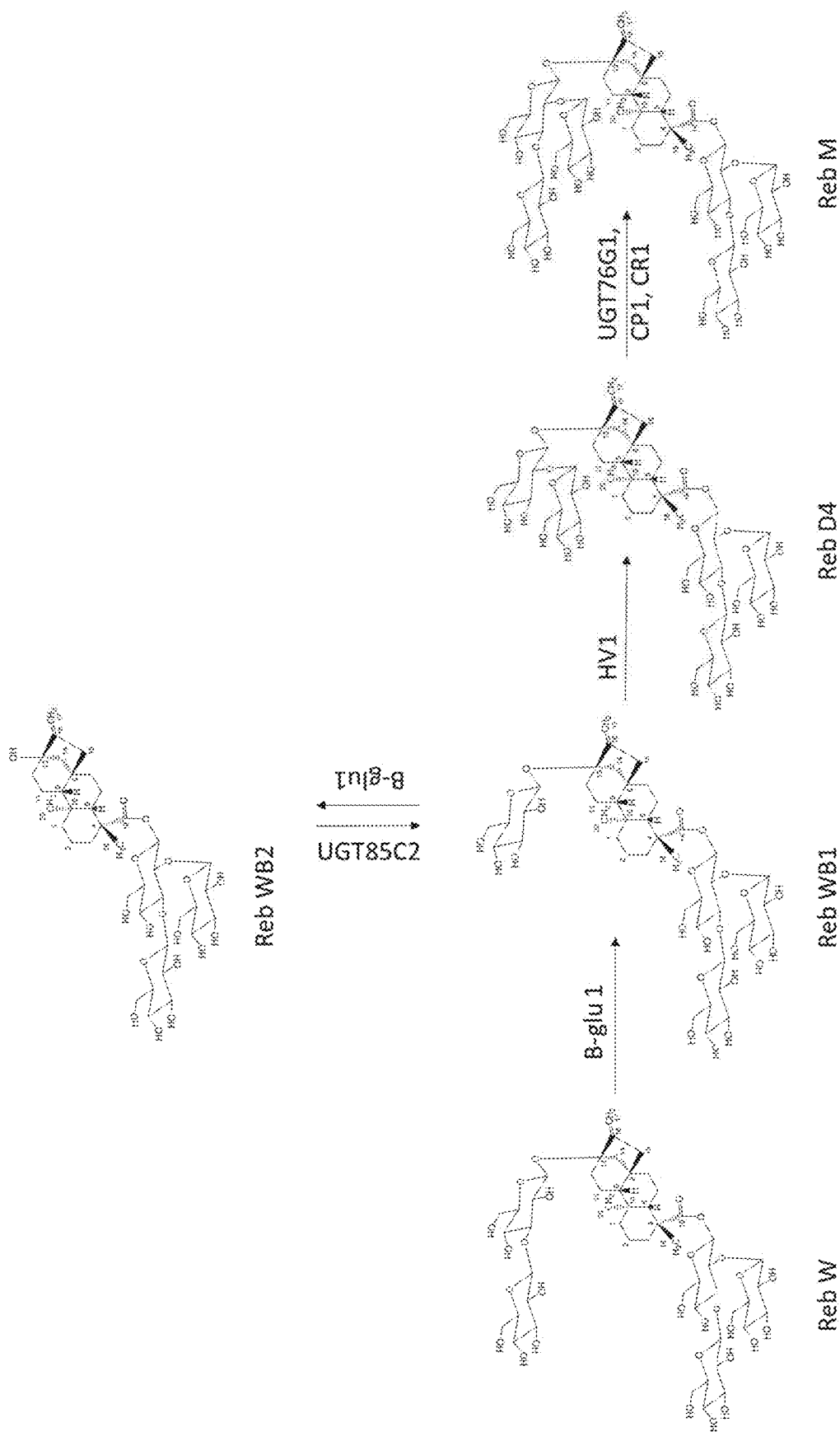
FIG. 14. Shows the Synthetic Pathway for Rebaudioside M biosynthesis pathway from Rebaudioside W.

The present disclosure relates to the production of a steviol glycoside of interest, Reb D4 and then using UGT enzymes to allow Reb D4 glycoside to convert to Reb M. The present disclosure also relates to the production of other steviol glycosides of interest, Reb WB1 and Reb WB2. The subject technology provides recombinant polypeptides with UDP glycosyltransferase activities, such as 1,2-13-O-glucose glycosylation activity and 1,3-13-O-glucose glycosylation activity for synthesizing steviol glycosides. The recombinant polypeptide of the subject technology is useful for the biosynthesis of steviol glycoside compounds. In the present disclosure, UDP-glycosyltransferase (UGT) refers to an enzyme that transfers a sugar residue from an activated donor molecule (typically UDP-glucose) to an acceptor molecule. The 1,3-13-O-glucose glycosylation activity refers to an enzymatic activity that transfers a sugar moiety to the C-3' of the 13-0 glucose moiety of rebaudioside D4 to produce Reb M (FIG. 14). The subject technology also provides recombinant polypeptides with beta-glucosidase activity for synthesizing steviol glycosides.

Synthetic Biology

Standard recombinant DNA and molecular cloning techniques used here are well known in the art and are described, for example, by Sambrook, J., Fritsch, E. F. and Maniatis, T. MOLECULAR CLONING: A LABORATORY MANUAL, 2nd ed.; Cold Spring Harbor Laboratory: Cold Spring Harbor, N.Y., 1989 (hereinafter "Maniatis"); and by Silhavy, T. J., Bennan, M. L. and Enquist, L. W. EXPERIMENTS WITH GENE FUSIONS; Cold Spring Harbor Laboratory: Cold Spring Harbor, N.Y., 1984; and by Ausubel, F. M. et al., IN CURRENT PROTOCOLS IN MOLECULAR BIOLOGY, published by GREENE PUBLISHING AND WILEY-INTERSCIENCE, 1987; (the entirety of each of which is hereby incorporated herein by reference).

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred materials and methods are described below.

The disclosure will be more fully understood upon consideration of the following non-limiting Examples. It should be understood that these Examples, while indicating preferred embodiments of the subject technology, are given by way of illustration only. From the above discussion and these Examples, one skilled in the art can ascertain the essential characteristics of the subject technology, and without departing from the spirit and scope thereof, can make various changes and modifications of the subject technology to adapt it to various uses and conditions.

Glycosylation is often considered a ubiquitous reaction controlling the bioactivity and storage of plant natural products. Glycosylation of small molecules is catalyzed by a superfamily of transferases in most plant species that have been studied to date. These glycosyltransferases (GTs) have been classified into over 60 families. Of these, the family 1 GT enzymes, also known as the UDP glycosyltransferases (UGTs), transfer UDP-activated sugar moieties to specific acceptor molecules. These are the molecules that transfer such sugar moieties in the steviol glycosides to create various rebaudiosides. Each of these UGTs have their own activity profile and preferred structure locations where they transfer their activated sugar moieties.

Production Systems

Expression of proteins in prokaryotes is most often carried out in a bacterial host cell with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such vectors are within the scope of the present disclosure.

In an embodiment, the expression vector includes those genetic elements for expression of the recombinant polypeptide in bacterial cells. The elements for transcription and translation in the bacterial cell can include a promoter, a coding region for the protein complex, and a transcriptional terminator.

A person of ordinary skill in the art will be aware of the molecular biology techniques available for the preparation of expression vectors. The polynucleotide used for incorporation into the expression vector of the subject technology, as described above, can be prepared by routine techniques such as polymerase chain reaction (PCR).

A number of molecular biology techniques have been developed to operably link DNA to vectors via complementary cohesive termini. In one embodiment, complementary homopolymer tracts can be added to the nucleic acid molecule to be inserted into the vector DNA. The vector and nucleic acid molecule are then joined by hydrogen bonding between the complementary homopolymeric tails to form recombinant DNA molecules.

In an alternative embodiment, synthetic linkers containing one or more restriction sites provide are used to operably link the polynucleotide of the subject technology to the expression vector. In an embodiment, the polynucleotide is generated by restriction endonuclease digestion. In an embodiment, the nucleic acid molecule is treated with bacteriophage T4 DNA polymerase or $E.\ coli$ DNA polymerase I, enzymes that remove protruding, 3'-single-stranded termini with their 3'-5'-exonucleolytic activities, and fill in recessed 3'-ends with their polymerizing activities, thereby generating blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the product of the reaction is a polynucleotide carrying polymeric linker sequences at its ends. These polynucleotides are then cleaved with the appropriate restriction enzyme and ligated to an expression vector that has been cleaved with an enzyme that produces termini compatible with those of the polynucleotide.

Alternatively, a vector having ligation-independent cloning (LIC) sites can be employed. The required PCR amplified polynucleotide can then be cloned into the LIC vector without restriction digest or ligation (Aslanidis and de Jong, NUCL. ACID. RES. 18 6069-74, (1990), Haun, et al, BIOTECHNIQUES 13, 515-18 (1992), which is incorporated herein by reference to the extent it is consistent herewith).

In an embodiment, in order to isolate and/or modify the polynucleotide of interest for insertion into the chosen plasmid, it is suitable to use PCR. Appropriate primers for use in PCR preparation of the sequence can be designed to isolate the required coding region of the nucleic acid molecule, add restriction endonuclease or LIC sites, place the coding region in the desired reading frame.

In an embodiment, a polynucleotide for incorporation into an expression vector of the subject technology is prepared by the use of PCR using appropriate oligonucleotide primers. The coding region is amplified, whilst the primers themselves become incorporated into the amplified sequence product. In an embodiment, the amplification primers contain restriction endonuclease recognition sites, which allow the amplified sequence product to be cloned into an appropriate vector.

The expression vectors can be introduced into plant or microbial host cells by conventional transformation or transfection techniques. Transformation of appropriate cells with an expression vector of the subject technology is accomplished by methods known in the art and typically depends on both the type of vector and cell. Suitable techniques include calcium phosphate or calcium chloride co-precipitation, DEAE-dextran mediated transfection, lipofection, chemoporation or electroporation.

Successfully transformed cells, that is, those cells containing the expression vector, can be identified by techniques well known in the art. For example, cells transfected with an expression vector of the subject technology can be cultured to produce polypeptides described herein. Cells can be examined for the presence of the expression vector DNA by techniques well known in the art.

The host cells can contain a single copy of the expression vector described previously, or alternatively, multiple copies of the expression vector.

In some embodiments, the transformed cell is an animal cell, an insect cell, a plant cell, an algal cell, a fungal cell, or a yeast cell. In some embodiments, the cell is a plant cell selected from the group consisting of: canola plant cell, a rapeseed plant cell, a palm plant cell, a sunflower plant cell, a cotton plant cell, a corn plant cell, a peanut plant cell, a flax plant cell, a sesame plant cell, a soybean plant cell, and a *petunia* plant cell.

Microbial host cell expression systems and expression vectors containing regulatory sequences that direct high level expression of foreign proteins are well known to those skilled in the art. Any of these could be used to construct vectors for expression of the recombinant polypeptide of the subjection technology in a microbial host cell. These vectors could then be introduced into appropriate microorganisms via transformation to allow for high level expression of the recombinant polypeptide of the subject technology.

Vectors or cassettes useful for the transformation of suitable microbial host cells are well known in the art. Typically the vector or cassette contains sequences directing transcription and translation of the relevant polynucleotide, a selectable marker, and sequences allowing autonomous replication or chromosomal integration. Suitable vectors comprise a region 5' of the polynucleotide which harbors transcriptional initiation controls and a region 3' of the DNA fragment which controls transcriptional termination. It is preferred for both control regions to be derived from genes homologous to the transformed host cell, although it is to be understood that such control regions need not be derived from the genes native to the specific species chosen as a host.

Initiation control regions or promoters, which are useful to drive expression of the recombinant polypeptide in the desired microbial host cell are numerous and familiar to those skilled in the art. Virtually any promoter capable of driving these genes is suitable for the subject technology including but not limited to CYCI, HIS3, GALI, GALIO, ADHI, PGK, PH05, GAPDH, ADCI, TRPI, URA3, LEU2, ENO, TPI (useful for expression in *Saccharomyces*); AOXI (useful for expression in *Pichia*); and lac, tip, JPL, IPR, T7, tac, and trc (useful for expression in *Escherichia coli*).

Termination control regions may also be derived from various genes native to the microbial hosts. A termination site optionally may be included for the microbial hosts described herein.

In plant cells, the expression vectors of the subject technology can include a coding region operably linked to promoters capable of directing expression of the recombinant polypeptide of the subject technology in the desired tissues at the desired stage of development. For reasons of convenience, the polynucleotides to be expressed may comprise promoter sequences and translation leader sequences derived from the same polynucleotide. 3' non-coding sequences encoding transcription termination signals should also be present. The expression vectors may also comprise one or more introns in order to facilitate polynucleotide expression.

For plant host cells, any combination of any promoter and any terminator capable of inducing expression of a coding region may be used in the vector sequences of the subject technology. Some suitable examples of promoters and terminators include those from nopaline synthase (nos), octopine synthase (ocs) and cauliflower mosaic virus (CaMV) genes. One type of efficient plant promoter that may be used is a high level plant promoter. Such promoters, in operable linkage with an expression vector of the subject technology should be capable of promoting the expression of the vector. High level plant promoters that may be used in the subject technology include the promoter of the small subunit (s) of the ribulose-1,5-bisphosphate carboxylase for example from soybean (Berry-Lowe et al., J. MOLECULAR AND APP. GEN., 1:483 498 (1982), the entirety of which is hereby incorporated herein to the extent it is consistent herewith), and the promoter of the chlorophyll binding protein. These two promoters are known to be light-induced in plant cells (see, for example, GENETIC ENGINEERING OF PLANTS, AN AGRICULTURAL PERSPECTIVE, A. Cashmore, Plenum, N.Y. (1983), pages 29 38; Coruzzi, G. et al., The Journal of Biological CHEMISTRY, 258: 1399 (1983), and Dunsmuir, P. et al., JOURNAL OF MOLECULAR AND APPLIED GENETICS, 2:285 (1983), each of which is hereby incorporated herein by reference to the extent they are consistent herewith).

Precursor Synthesis to Reb D4

As previously stated steviol glycosides are the chemical compounds responsible for the sweet taste of the leaves of the South American plant *Stevia rebaudiana* (Asteraceae) and in the plant *Rubus chingii* (Rosaceae). These compounds are glycosylated diterpenes. Specifically, their molecules can be viewed as a steviol molecule, with its hydroxyl hydrogen atom replaced by a glucose molecule to form an ester, and a hydroxyl hydrogen with combinations of glucose and rhamnose to form an acetal.

One method of making the compounds of interest in the current disclosure is to take common or inexpensive precursors such as steviol or rubosuside derived chemically or produced via biosynthesis in engineered microbes such as bacteria and/or yeast and to synthesize targeted steviol glycosides through known or inexpensive methods, such as Reb D4.

Aspects of the present disclosure relate to methods involving recombinantly expressing enzymes in a microbial system capable of producing steviol. In general, such enzymes may include: a copalyl diphosphate synthase (CPS), a kaurene synthase (KS) and a geranylgeranyl diphosphate to synthase (GGPPS) enzyme. This should occur in a microbial strain that expresses an endogenous isoprenoid synthesis pathway, such as the non-mevalonate (MEP) pathway or the mevalonic acid pathway (MVA). In some embodiments the cell is a bacterial cell, including *E. coli*, or yeast cell such as a *Saccharomyces* cell, *Pichia* cell, or a *Yarrowia* cell. In some embodiments, the cell is an algal cell or a plant cell.

Thereafter, the precursor is recovered from the fermentation culture for use in chemical synthesis. Typically, this is steviol though it can be kaurene, or a steviol glycoside from the cell culture. In some embodiments, the steviol, kaurene and/or steviol glycosides is recovered from the gas phase while in other embodiments, an organic layer or polymeric resin is added to the cell culture, and the kaurene, steviol and/or steviol glycosides is recovered from the organic layer or polymeric resin. In some embodiments, the steviol glycoside is selected from rebaudioside A, rebaudioside B, rebaudioside C, rebaudioside D, rebaudioside E, rebaudioside F or dulcoside A. In some embodiments, the terpenoid produced is steviolbioside or stevioside. It should also be appreciated that in some embodiments, at least one enzymatic step, such as one or more glycosylation steps, are performed ex vivo.

Part of the invention is the production of the Reb D4 steviol glycoside that is then subject to further enzymatic conversion to Reb M. According to the current disclosure the biosynthesis for the conversion of microbially produced steviol to a desired steviol glycosides (here Reb D4) occurs when the diterpenoid steviol is converted to stevioside and rebaudioside A using multi-step chemical assembly of sugar moiety into the steviol backbone. More specifically the chemical synthesis consists of following steps: 1) A trimethylsilyl (TMS) protected at C19 COOH group of the steviol is synthesized from the starting precursor steviol. Tri-glycosylation at the C13-OH position of the steviol is performed using protected β-Glc-β-Glc(2→1)-β-Glc(3→1) group. This is followed by a deprotection of the TMS and coupling of a protected mono β-Glc-Br moiety. The final deprotection removes all of the protecting groups to produce rebaudioside D4.

Biosynthesis of Steviol Glycosides

As described herein, the recombinant polypeptides of the present technology have UDP-glycosyltransferase activities and are useful for developing biosynthetic methods for preparing steviol glycosides that are not present or typically of low abundance in natural sources, such as rebaudioside D4 and rebaudioside M respectively. The recombinant polypeptides of the present technology have beta-glucosidase or UDP-glycosyltransferase activities, are useful for developing biosynthetic methods for preparing novel steviol glycosides, such as rebaudioside D4 and useful in the production of rebaudioside M.

The substrate can be any natural or synthetic compound capable of being converted into a steviol glycoside compound in a reaction catalyzed by one or more UDP glycosyltransferases. For example, the substrate can be natural *stevia* extract, steviol, steviol-13-O-glucoside, steviol-19-O-glucoside, steviol-1,2-bioside, rubusoside, stevioside, rebaudioside A, rebaudioside G or rebaudioside E. The substrate can be a pure compound or a mixture of different compounds. Preferably, the substrate includes a compound selected from the group consisting of rubusoside, stevioside, steviol, rebaudioside A, rebaudioside E and combinations thereof.

The method described herein also provides a coupling reaction system in which the recombinant peptides described herein is allowed to function in combination with one or more additional enzymes to improve the efficiency or modify the outcome of the overall biosynthesis of steviol glycoside compounds. For example, the additional enzyme may regenerate the UDP-glucose needed for the glycosylation reaction by converting the UDP produced from the glycosylation reaction back to UDP-glucose (using, for example, sucrose as a donor of the glucose residue), thus improving the efficiency of the glycosylation reaction.

In another embodiment, the method of the subject technology further includes incubating a recombinant UDP-glycosyltransferase with the recombinant sucrose synthase, the substrate, and the recombinant polypeptide described herein. The recombinant UDP-glycosyltransferase can catalyze a different glycosylation reaction than the one catalyzed by the recombinant polypeptide of the subject technology.

Suitable UDP-glycosyltransferase includes any UGT known in the art as capable of catalyzing one or more reactions in the biosynthesis of steviol glycoside compounds, such as UGT85C2, UGT74G1, UGT76G1, or the functional homologs thereof.

Typically, in the in vitro method of the subject technology, UDP-Glucose is included in the buffer at a concentration of from about 0.2 mM to about 5 mM, preferably from about 0.5 mM to about 2 mM, more preferably from about 0.7 mM to about 1.5 mM. In an embodiment, when a recombinant sucrose synthase is included in the reaction, sucrose is also included in the buffer at a concentration of from about 100 mM to about 500 mM, preferably from about 200 mM to about 400 mM, more preferably from about 250 mM to about 350 mM.

Typically, in the in vitro method of the subject technology, the weight ratio of the recombinant polypeptide to the substrate, on a dry weight basis, is from about 1:100 to about 1:5, preferably from about 1:50 to about 1:10, more preferably from about 1:25 to about 1:15.

Typically, the reaction temperature of the in vitro method is from about 20° C. to about 40° C., suitably from 25° C. to about 37° C., more suitably from 28° C. to about 32° C.

One with skill in the art will recognize that the steviol glycoside composition produced by the method described herein can be further purified and mixed with other steviol glycosides, flavors, or sweeteners to obtain a desired flavor or sweetener composition. For example, a composition enriched with rebaudioside D4 produced as described herein can be mixed with a natural *stevia* extract containing rebaudioside A as the predominant steviol glycoside, or with other synthetic or natural steviol glycoside products to make a desired sweetener composition. Alternatively, a substantially purified steviol glycoside (e.g., rebaudioside D4) obtained from the steviol glycoside composition described herein can be combined with other sweeteners, such as sucrose, maltodextrin, aspartame, sucralose, neotame, acesulfame potassium, and saccharin. The amount of steviol glycoside relative to other sweeteners can be adjusted to obtain a desired taste, as known in the art. The steviol glycoside composition described herein (including rebaudioside D, rebaudioside E, rebaudioside D4, rebaudioside M or a combination thereof) can be included in food products (such as beverages, soft drinks, ice cream, dairy products, confectioneries, cereals, chewing gum, baked goods, etc.), dietary supplements, medical nutrition, as well as pharmaceutical products.

One with skill in the art will recognize that the steviol glycoside composition produced by the method described herein can be further purified and mixed with other steviol glycosides, flavors, or sweeteners to obtain a desired flavor or sweetener composition. For example, a composition enriched with rebaudioside D4 produced as described herein can be mixed with a natural *stevia* extract containing rebaudioside A as the predominant steviol glycoside, or with other synthetic or natural steviol glycoside products to make a desired sweetener composition. Alternatively, a substantially purified steviol glycoside (e.g., rebaudioside D4) obtained from the steviol glycoside composition described herein can be combined with other sweeteners, such as sucrose, maltodextrin, aspartame, sucralose, neotame, acesulfame potassium, and saccharin. The amount of steviol glycoside relative to other sweeteners can be adjusted to obtain a desired taste, as known in the art. The steviol glycoside composition described herein (including rebaudioside D, rebaudioside E, rebaudioside D4, rebaudioside WB1, rebaudioside WB2, rebaudioside M or a combination thereof) can be included in food products (such as beverages, soft drinks, ice cream, dairy products, confectioneries, cereals, chewing gum, baked goods, etc.), dietary supplements, medical nutrition, as well as pharmaceutical products.

Analysis of Sequence Similarity Using Identity Scoring

As used herein "sequence identity" refers to the extent to which two optimally aligned polynucleotide or peptide sequences are invariant throughout a window of alignment of components, e.g., nucleotides or amino acids. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this disclosure "percent identity" may also be determined using BLASTX version 2.0 for translated nucleotide sequences and BLASTN version 2.0 for polynucleotide sequences.

The percent of sequence identity is preferably determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, JOURNAL OF MOLECULAR BIOLOGY 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, ADVANCES IN APPLIED MATHEMATICS, 2:482-489, 1981, Smith et al., NUCLEIC ACIDS RESEARCH 11:2205-2220, 1983). The percent identity is most preferably determined using the "Best Fit" program.

Useful methods for determining sequence identity are also disclosed in the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; Altschul et al., J. MOL. BIOL. 215:403-410 (1990); version 2.0 or higher of BLAST programs allows the introduction of gaps (deletions and insertions) into alignments; for peptide sequence BLASTX can be used to determine sequence identity; and, for polynucleotide sequence BLASTN can be used to determine sequence identity.

As used herein, the term "substantial percent sequence identity" refers to a percent sequence identity of at least about 70% sequence identity, at least about 80% sequence identity, at least about 85% identity, at least about 90% sequence identity, or even greater sequence identity, such as about 98% or about 99% sequence identity. Thus, one embodiment of the disclosure is a polynucleotide molecule that has at least about 70% sequence identity, at least about 80% sequence identity, at least about 85% identity, at least about 90% sequence identity, or even greater sequence identity, such as about 98% or about 99% sequence identity with a polynucleotide sequence described herein. Polynucleotide molecules that have the activity of the Blu1 and CP1 genes of the current disclosure are capable of directing the production of a variety of steviol glycosides and have a substantial percent sequence identity to the polynucleotide sequences provided herein and are encompassed within the scope of this disclosure.

Identity and Similarity

Identity is the fraction of amino acids that are the same between a pair of sequences after an alignment of the sequences (which can be done using only sequence information or structural information or some other information, but usually it is based on sequence information alone), and similarity is the score assigned based on an alignment using some similarity matrix. The similarity index can be any one of the following BLOSUM62, PAM250, or GONNET, or any matrix used by one skilled in the art for the sequence alignment of proteins.

Identity is the degree of correspondence between two sub-sequences (no gaps between the sequences). An identity of 25% or higher implies similarity of function, while 18-25% implies similarity of structure or function. Keep in mind that two completely unrelated or random sequences (that are greater than 100 residues) can have higher than 20% identity. Similarity is the degree of resemblance between two sequences when they are compared. This is dependent on their identity.

Consumable Products

In another aspect, the present disclosure is directed to a consumable product comprising a rebaudioside as described herein, e.g., Reb W1, Reb W2, Reb D4, Reb M, or a combination thereof such as Reb D4 and Reb M. In some embodiments, the consumable product comprises a sweetening amount of a rebaudioside as described herein, e.g., Reb W1, Reb W2, Reb D4, and/or Reb M. In some embodiments, the consumable product is selected from the group consisting of a beverage product, a food product, a nutraceutical, a pharmaceutical, a dietary supplement, a dental hygienic composition, an edible gel composition, a cosmetic product and a tabletop flavoring.

In some embodiments, the consumable product can have a sweetness intensity equivalent to about 1% (w/v-%) to about 4% (w/v-%) sucrose solution.

In some embodiments, the rebaudioside as described herein, e.g., Reb W1, Reb W2, Reb D4, Reb M, or a combination thereof such as Reb D4 and Reb M, is the only sweetener in the orally consumable product.

In some embodiments, the consumable product can also have at least one additional sweetener. The at least one additional sweetener can be a natural high intensity sweetener, for example. The additional sweetener can be selected from a stevia extract, a steviol glycoside, stevioside, rebaudioside A, rebaudioside B, rebaudioside C, rebaudioside D, rebaudioside D2, rebaudioside E, rebaudioside F, dulcoside A, rubusoside, steviolbioside, sucrose, high fructose corn syrup, fructose, glucose, xylose, arabinose, rhamnose, erythritol, xylitol, mannitol, sorbitol, inositol, AceK, aspartame, neotame, sucralose, saccharine, naringin dihydrochalcone (NarDHC), neohesperidin dihydrochalcone (NDHC), rubusoside, mogroside IV, siamenoside I, mogroside V, monatin, thaumatin, monellin, brazzein, L-alanine, glycine, Lo Han Guo, hernandulcin, phyllodulcin, trilobtain, and combinations thereof.

In some embodiments, the consumable product can also have at least one additive. The additive can be, for example, a carbohydrate, a polyol, an amino acid or salt thereof, a polyamino acid or salt thereof, a sugar acid or salt thereof, a nucleotide, an organic acid, an inorganic acid, an organic salt, an organic acid salt, an organic base salt, an inorganic salt, a bitter compound, a flavorant, a flavoring ingredient, an astringent compound, a protein, a protein hydrolysate, a surfactant, an emulsifier, a flavonoid, an alcohol, a polymer, and combinations thereof.

In one aspect, the present disclosure is directed to a beverage product comprising a sweetening amount of a rebaudioside as described herein, e.g., Reb W1, Reb W2, Reb D4, Reb M, or a combination thereof such as Reb D4 and Reb M.

The beverage product can be, for example, a carbonated beverage product or a non-carbonated beverage product. The beverage product can also be, for example, a soft drink, a fountain beverage, a frozen beverage, a ready-to-drink beverage, a frozen and ready-to-drink beverage, coffee, tea, a dairy beverage, a powdered soft drink, a liquid concentrate, flavored water, enhanced water, fruit juice, a fruit juice flavored drink, a sport drink, or an energy drink.

In some embodiments, a beverage product of the present disclosure can include one or more beverage ingredients such as, for example, acidulants, fruit juices and/or vegetable juices, pulp, etc., flavorings, coloring, preservatives, vitamins, minerals, electrolytes, erythritol, tagatose, glycerine, and carbon dioxide. Such beverage products may be provided in any suitable form, such as a beverage concentrate or a carbonated, ready-to-drink beverage.

In certain embodiments, beverage products of the present disclosure can have any of numerous different specific formulations or constitutions. The formulation of a beverage product of the present disclosure can vary to a certain extent, depending upon such factors as the product's intended market segment, its desired nutritional characteristics, flavor profile, and the like. For example, in certain embodiments, it can generally be an option to add further ingredients to the formulation of a particular beverage product. For example, additional sweeteners can be added, flavorings, electrolytes, vitamins, fruit juices or other fruit products, tastents, masking agents and the like, flavor enhancers, and/or carbonation typically may be added to any such formulations to vary the taste, mouthfeel, nutritional characteristics, etc. In embodiments, the beverage product can be a cola beverage that contains water, a rebaudioside as described herein (e.g., Reb W1, Reb W2, Reb D4, Reb M, or a combination thereof such as Reb D4 and Reb M), an acidulant, and flavoring. Exemplary flavorings can be, for example, cola flavoring, citrus flavoring, and spice flavorings. In some embodiments, carbonation in the form of carbon dioxide can be added for effervescence. In other embodiments, preservatives can be added, depending upon the other ingredients, production technique, desired shelf life, etc. In certain embodiments, caffeine can be added. In some embodiments, the beverage product can be a cola-flavored carbonated beverage, characteristically containing carbonated water, sweetener, kola nut extract and/or other flavoring, caramel coloring, one or more acids, and optionally other ingredients.

In another aspect, the present disclosure is directed to a consumable product comprising a rebaudioside as described herein (e.g., Reb W1, Reb W2, Reb D4, Reb M, or a combination thereof such as Reb D4 and Reb M), wherein the consumable product is a food product, a nutraceutical, a pharmaceutical, a dietary supplement, a dental hygienic composition, an edible gel composition, a cosmetic product or a tabletop flavoring. In some embodiments, the rebaudioside is present in a sweetening amount.

As used herein, "dietary supplement(s)" refers to compounds intended to supplement the diet and provide nutrients, such as vitamins, minerals, fiber, fatty acids, amino acids, etc. that may be missing or may not be consumed in sufficient quantities in a diet. Any suitable dietary supplement known in the art may be used. Examples of suitable dietary supplements can be, for example, nutrients, vitamins, minerals, fiber, fatty acids, herbs, botanicals, amino acids, and metabolites.

As used herein, "nutraceutical(s)" refers to compounds, which includes any food or part of a food that may provide medicinal or health benefits, including the prevention and/or treatment of disease or disorder (e.g., fatigue, insomnia, effects of aging, memory loss, mood disorders, cardiovascular disease and high levels of cholesterol in the blood, diabetes, osteoporosis, inflammation, autoimmune disorders, etc.). Any suitable nutraceutical known in the art may be used. In some embodiments, nutraceuticals can be used as supplements to food and beverages and as pharmaceutical formulations for enteral or parenteral applications which may be solid formulations, such as capsules or tablets, or liquid formulations, such as solutions or suspensions.

In some embodiments, dietary supplements and nutraceuticals can further contain protective hydrocolloids (such as gums, proteins, modified starches), binders, film-forming agents, encapsulating agents/materials, wall/shell materials, matrix compounds, coatings, emulsifiers, surface active agents, solubilizing agents (oils, fats, waxes, lecithins, etc.), adsorbents, carriers, fillers, co-compounds, dispersing agents, wetting agents, processing aids (solvents), flowing agents, taste-masking agents, weighting agents, jellyfying agents, gel-forming agents, antioxidants and antimicrobials.

As used herein, a "gel" refers to a colloidal system in which a network of particles spans the volume of a liquid medium. Although gels mainly are composed of liquids, and thus exhibit densities similar to liquids, gels have the structural coherence of solids due to the network of particles that spans the liquid medium. For this reason, gels generally appear to be solid, jelly-like materials. Gels can be used in a number of applications. For example, gels can be used in foods, paints, and adhesives. Gels that can be eaten are referred to as "edible gel compositions." Edible gel compositions typically are eaten as snacks, as desserts, as a part of staple foods, or along with staple foods. Examples of suitable edible gel compositions can be, for example, gel desserts, puddings, jams, jellies, pastes, trifles, aspics, marshmallows, gummy candies, and the like. In some embodiments, edible gel mixes generally are powdered or granular solids to which a fluid may be added to form an edible gel composition. Examples of suitable fluids can be, for example, water, dairy fluids, dairy analogue fluids, juices, alcohol, alcoholic beverages, and combinations thereof. Examples of suitable dairy fluids can be, for example, milk, cultured milk, cream, fluid whey, and mixtures thereof. Examples of suitable dairy analogue fluids can be, for example, soy milk and non-dairy coffee whitener.

As used herein, the term "gelling ingredient" refers to any material that can form a colloidal system within a liquid medium. Examples of suitable gelling ingredients can be, for example, gelatin, alginate, carageenan, gum, pectin, konjac, agar, food acid, rennet, starch, starch derivatives, and combinations thereof. It is well known to those in the art that the amount of gelling ingredient used in an edible gel mix or an edible gel composition can vary considerably depending on a number of factors such as, for example, the particular gelling ingredient used, the particular fluid base used, and the desired properties of the gel.

Gel mixes and gel compositions of the present disclosure can be prepared by any suitable method known in the art. In some embodiments, edible gel mixes and edible gel compositions of the present disclosure can be prepared using other ingredients in addition to the gelling agent. Examples of other suitable ingredients can be, for example, a food acid, a salt of a food acid, a buffering system, a bulking agent, a sequestrant, a cross-linking agent, one or more flavors, one or more colors, and combinations thereof.

Any suitable pharmaceutical composition known in the art may be used. In some embodiments, pharmaceutical compositions of the present disclosure can be used to formulate pharmaceutical drugs containing one or more active agents that exert a biological effect. Accordingly, in some embodiments, pharmaceutical compositions of the present disclosure can contain one or more active agents that exert a biological effect. Suitable active agents are well known in the art (e.g., The Physician's Desk Reference). Such compositions can be prepared according to procedures well known in the art, for example, as described in Remington's Pharmaceutical Sciences, Mack Publishing Co., Easton, Pa., USA.

A rebaudioside as described herein (e.g., Reb W1, Reb W2, Reb D4, Reb M, or a combination thereof such as Reb D4 and Reb M) can be used with any suitable dental and oral hygiene compositions known in the art. Examples of suitable dental and oral hygiene compositions can be, for example, toothpastes, tooth polishes, dental floss, mouthwashes, mouth rinses, denitrifies, mouth sprays, mouth refreshers, plaque rinses, dental pain relievers, and the like.

As used herein, "food product" refers to any solid or liquid ingestible material that can, but need not, have a nutritional value and be intended for consumption by humans and animals.

Examples of suitable food products can be, for example, confectionery compositions, such as candies, mints, fruit flavored drops, cocoa products, chocolates, and the like; condiments, such as ketchup, mustard, mayonnaise, and the like; chewing gums; cereal compositions; baked goods, such as breads, cakes, pies, cookies, and the like; dairy products, such as milk, cheese, cream, ice cream, sour cream, yogurt, sherbet, and the like; tabletop sweetener compositions; soups; stews; convenience foods; meats, such as ham, bacon, sausages, jerky, and the like; gelatins and gelatin-like products such as jams, jellies, preserves, and the like; fruits; vegetables; egg products; icings; syrups including molasses; snacks; nut meats and nut products; and animal feed.

Food products can also be herbs, spices and seasonings, natural and synthetic flavors, and flavor enhancers, such as monosodium glutamate. In some embodiments, food products can be, for example, prepared packaged products, such as dietetic sweeteners, liquid sweeteners, granulated flavor mixes, pet foods, livestock feed, tobacco, and materials for baking applications, such as powdered baking mixes for the preparation of breads, cookies, cakes, pancakes, donuts and the like. In other embodiments, food products can also be diet and low-calorie food and beverages containing little or no sucrose.

In certain embodiments that may be combined with any of the preceding embodiments, the rebaudioside as described herein (e.g., Reb W1, Reb W2, Reb D4, Reb M, or a combination thereof such as Reb D4 and Reb M) is the only sweetener, optionally wherein the product has a sweetness intensity equivalent to about 1% to about 4% (w/v-%) sucrose solution. In certain embodiments that can be combined with any of the preceding embodiments, the consumable products and beverage products can further include an additional sweetener, optionally wherein the product has a sweetness intensity equivalent to about 1% to about 10% (w/v-%) sucrose solution. In certain embodiments that can be combined with any of the preceding embodiments, every sweetening ingredient in the product is a high intensity sweetener. In certain embodiments that can be combined with any of the preceding embodiments, every sweetening ingredient in the product can a natural high intensity sweetener. In certain embodiments that can be combined with any of the preceding embodiments, the additional sweetener contains one or more sweeteners selected from a stevia extract, a steviol glycoside, stevioside, rebaudioside A, rebaudioside B, rebaudioside C, rebaudioside D, rebaudioside D2, rebaudioside F, dulcoside A, rubusoside, steviolbioside, sucrose, high fructose corn syrup, fructose, glucose, xylose, arabinose, rhamnose, erythritol, xylitol, mannitol, sorbitol, inositol, AceK, aspartame, neotame, sucralose, saccharine, naringin dihydrochalcone (NarDHC), neohesperidin dihydrochalcone (NDHC), rubusoside mogroside IV, siamenoside I, mogroside V, monatin, thaumatin, monellin, brazzein, L-alanine, glycine, Lo Han Guo, hernandulcin, phyllodulcin, trilobtain, and combinations thereof. In certain embodiments that can be combined with any of the preceding embodiments, the consumable products and beverage products can further include one or more additives selected from a carbohydrate, a polyol, an amino acid or salt thereof, a poly-amino acid or salt thereof, a sugar acid or salt thereof, a nucleotide, an organic acid, an inorganic acid, an organic salt, an organic acid salt, an organic base salt, an inorganic salt, a bitter compound, a flavorant, a flavoring ingredient, an astringent compound, a protein, a protein hydrolysate, a surfactant, an emulsifier, a flavonoid, an alcohol, a polymer, and combinations thereof. In certain embodiments that can be combined with any of the preceding embodiments, the rebaudioside as described herein (e.g., Reb W1, Reb W2, Reb D4, Reb M, or a combination thereof such as Reb D4 and Reb M) has a purity of about 50% to about 100% by weight before it is added into the product.

In some embodiments, a rebaudioside as described herein (e.g., Reb W1, Reb W2, Reb D4, Reb M, or a combination thereof such as Reb D4 and Reb M) is provided in a composition further comprising one or more of a filler, a bulking agent and an anticaking agent. Suitable fillers, bulking agents and anticaking agents are known in the art.

In certain embodiments, a rebaudioside as described herein (e.g., Reb W1, Reb W2, Reb D4, Reb M, or a combination thereof such as Reb D4 and Reb M) can be included and/or added at a final concentration that is sufficient to sweeten and/or enhance the sweetness of the consumable products and beverage products. The "final concentration" of the rebaudioside as described herein (e.g., Reb W1, Reb W2, Reb D4, Reb M, or a combination thereof such as Reb D4 and Reb M) present in the final consumable products and beverage products (i.e., after all ingredients and/or compounds have been added to produce the consumable products and beverage products). Accordingly, in certain embodiments, a rebaudioside as described herein (e.g., Reb W1, Reb W2, Reb D4, Reb M, or a combination thereof such as Reb D4 and Reb M) is included and/or added to a compound or ingredient used to prepare the consumable products and beverage products. The rebaudioside as described herein (e.g., Reb W1, Reb W2, Reb D4, Reb M, or a combination thereof such as Reb D4 and Reb M) may be present in a single compound or ingredient, or multiple compounds and ingredients. In some embodiments, a rebaudioside as described herein (e.g., Reb W1, Reb W2, Reb D4, Reb M, or a combination thereof such as Reb D4 and Reb M) included and/or added to the consumable products and beverage products.

In certain embodiments, a rebaudioside as described herein (e.g., Reb W1, Reb W2, Reb D4, Reb M, or a combination thereof such as Reb D4 and Reb M) is the only sweetener included and/or added to the consumable products and the beverage products. In some embodiments, the consumable products and the beverage products comprising the rebaudiosides have a sweetness intensity equivalent to about 1% to about 4% (w/v-%) sucrose solution, about 1% to about 3% (w/v-%) sucrose solution, or about 1% to about 2% (w/v-%) sucrose solution. Alternatively, the consumable products and the beverage products have a sweetness intensity equivalent to about 1% to about 4% (w/v-%) sucrose solution, about 2% to about 4% (w/v-%) sucrose solution, about 3% to about 4% (w/v-%) sucrose solution, or about 4%. For example, the consumable products and the beverage products may have a sweetness intensity equivalent to about 1%, about 2%, about 3%, or about 4% (w/v-%) sucrose solution, including any range in between these values.

The consumable products and beverage products of the present disclosure can include a mixture of a rebaudioside as described herein (e.g., Reb W1, Reb W2, Reb D4, Reb M, or a combination thereof such as Reb D4 and Reb M) and one or more sweeteners of the present disclosure in a ratio sufficient to achieve a desirable sweetness intensity, nutritional characteristic, taste profile, mouthfeel, or other organoleptic factor.

As is evident from the foregoing description, certain aspects of the present disclosure are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present disclosure.

Moreover, unless defined otherwise, all technical and scientific terms used herein have the same meaning as commonly understood by one of ordinary skill in the art to which the disclosure belongs. Although any methods and materials similar to or equivalent to or those described herein can be used in the practice or testing of the present disclosure, the preferred methods and materials are described above.

Although the foregoing invention has been described in some detail by way of illustration and example for purposes of understanding, it will be apparent to those skilled in the art that certain changes and modifications may be practiced. Therefore, the description and examples should not be construed as limiting the scope of the invention, which is delineated by the appended claims.

Example 1: Enzymatic Synthesis of Reb D4

There are several enzymatic methods of making Reb D4. One of the method starting from Reb W is presented here.

Previously, we demonstrated the production of Reb W from Reb V (WO2016054540). Here, we found Reb W can be hydrolyzed by beta-glucosidase (B-glu1, SEQ: 5) from *Pichia pastoris* to produce a novel steviol glycoside we called it "Rebaudioside WB1". The produced Rebaudioside WB1 can be hydrolyzed in turn by B-glu1 to produce Rebaudioside WB2. (see, FIG. 14).

More specifically, the full-length DNA fragments of B-glu1 (SEQ ID NO: 6) gene was synthesized. Specifically, the cDNA was codon optimized for *E. coli* expression (Genscript, Piscataway, N.J.). The synthesized DNA was cloned into a bacterial expression vector pETite N-His SUMO Kan Vector (Lucigen). The nucleotide sequence (SEQ ID NO: 6) encoding the B-glu1 (see, SEQ ID NO:5) was inserted in frame.

The expression construct was transformed into *E. coli* BL21 (DE3), which was subsequently grown in LB media containing 50 µg/mL kanamycin at 37° C. until reaching an OD600 of 0.8-1.0. Protein expression was induced by addition of 1 mM isopropyl β-D-1-thiogalactopyranoside (IPTG) and the culture was further grown at 16° C. for 22 hr. Cells were harvested by centrifugation (3,000×g; 10 min; 4° C.). The cell pellets were collected and were either used immediately or stored at −80° C.

The cell pellets were re-suspended in lysis buffer (50 mM potassium phosphate buffer, pH 7.2, 25 µg/ml lysozyme, 5 µg/ml DNase I, 20 mM imidazole, 500 mM NaCl, 10% glycerol, and 0.4% TRITON X-100). The cells were disrupted by sonication at 4° C., and the cell debris was clarified by centrifugation (18,000×g; 30 min). The supernatant was loaded to an equilibrated (equilibration buffer: 50 mM potassium phosphate buffer, pH 7.2, 20 mM imidazole, 500 mM NaCl, 10% glycerol) Ni-NTA (Qiagen) affinity column. After loading of protein sample, the column was washed with equilibration buffer to remove unbound contaminant proteins. The His-tagged B-glu1 recombinant polypeptide was eluted by equilibration buffer containing 250 mM imidazole.

The recombinant B-glu1 (10 µg) was added in a 200 µL in vitro reaction system. The reaction system contained 50 mM potassium phosphate buffer, pH 7.2, and 1 mg/ml Rebaudioside W as the substrate. The reaction was performed at 37° C. and terminated by adding 200 µL of 1-butanol. The samples were extracted three times with 200 µL of 1-butanol. The pooled fraction was dried and dissolved in 70 µL of 80% methanol for high-performance liquid chromatography (HPLC) analysis.

HPLC analysis was performed using a Dionex UPLC ultimate 3000 system (Sunnyvale, Calif.), including a quaternary pump, a temperature controlled column compartment, an auto sampler and a UV absorbance detector. Synergi Hydro-RP column with guard column was used for the characterization of steviol glycosides. Acetonitrile in water was used for elution in HPLC analysis. The detection wavelength was 210 nm.

Figure 3:
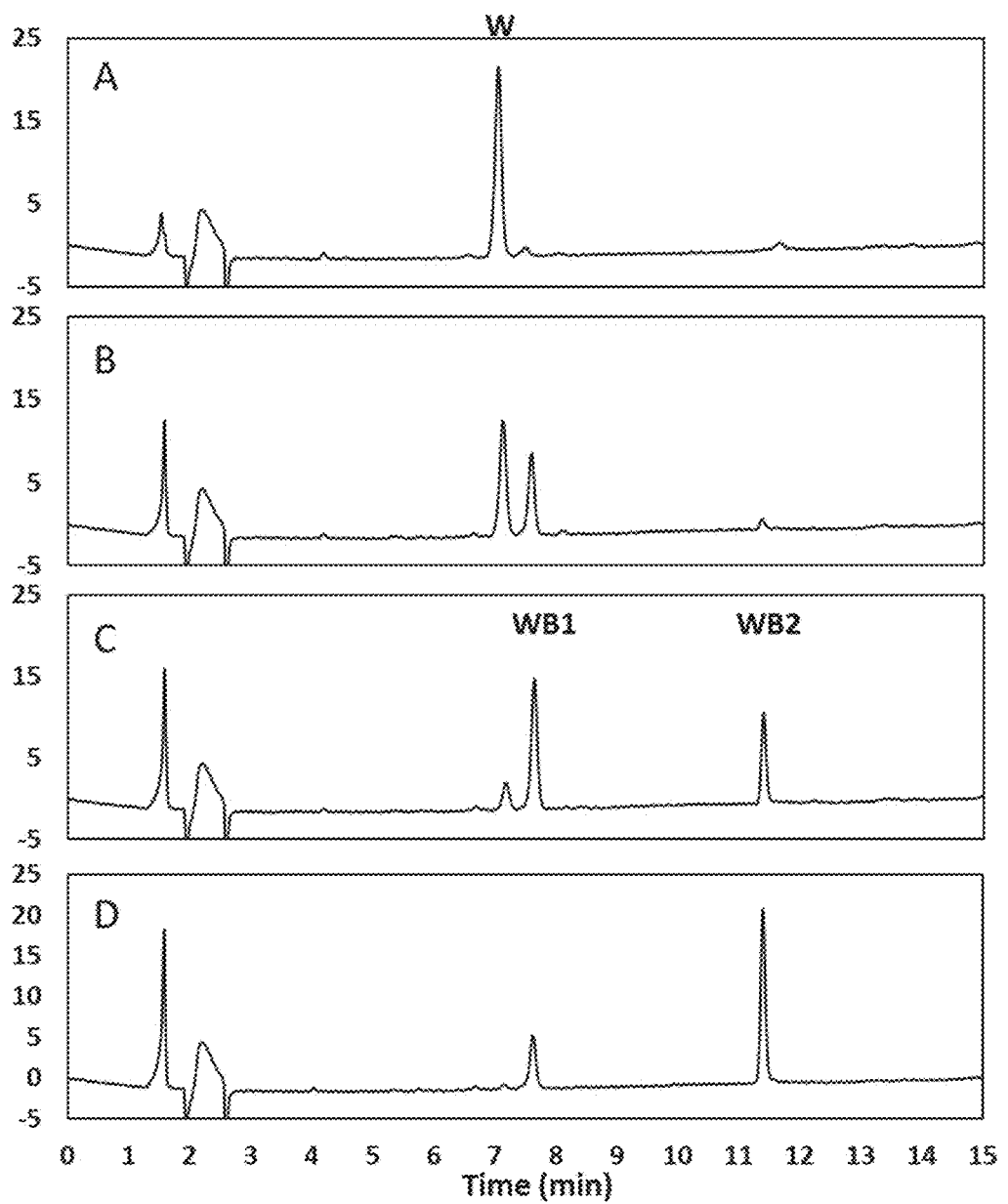
FIG. 3. Shows the HPLC profiles of the rebaudioside W hydrolysis products. Rebaudioside W is hydrolyzed by B-glu1 enzyme. A: Standard of rebaudioside W ("W"); B-D: Rebaudioside W was hydrolyzed by recombinant B-glu1 enzyme at 1 hour (B), 6 hours (C) and 24 hours (D).

As shown in FIG. 3, B-glu1 hydrolyzed rebaudioside W substrate to produce rebaudioside WB1 at 1 hour (FIG. 3B). The produced rebaudioside WB1 can be further converted to rebaudioside WB2 at later reaction time points (FIGS. 3C and 3D).

In conclusion, Rebaudioside W was hydrolyzed by B-glu1 to produce WB1, the produced WB1 was further hydrolyzed by B-glu1 to produce WB2.

Figure 2:
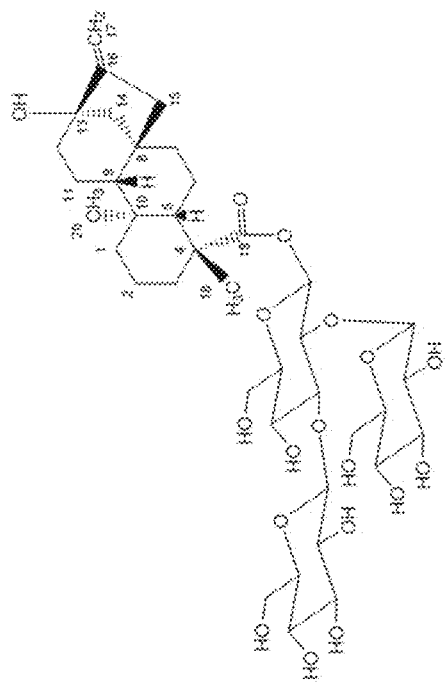
FIG. 2. Shows the structures of rebaudioside WB1 and WB2.
Figure 2:
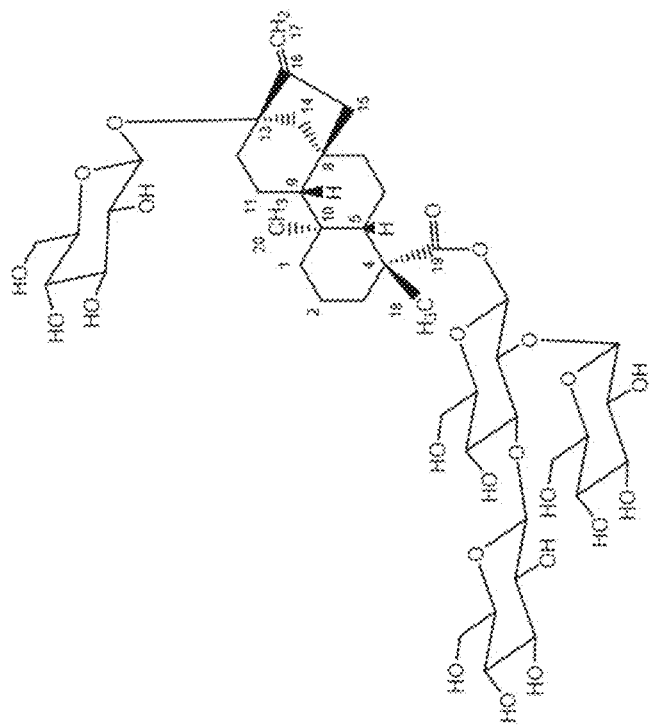
Figure 4:
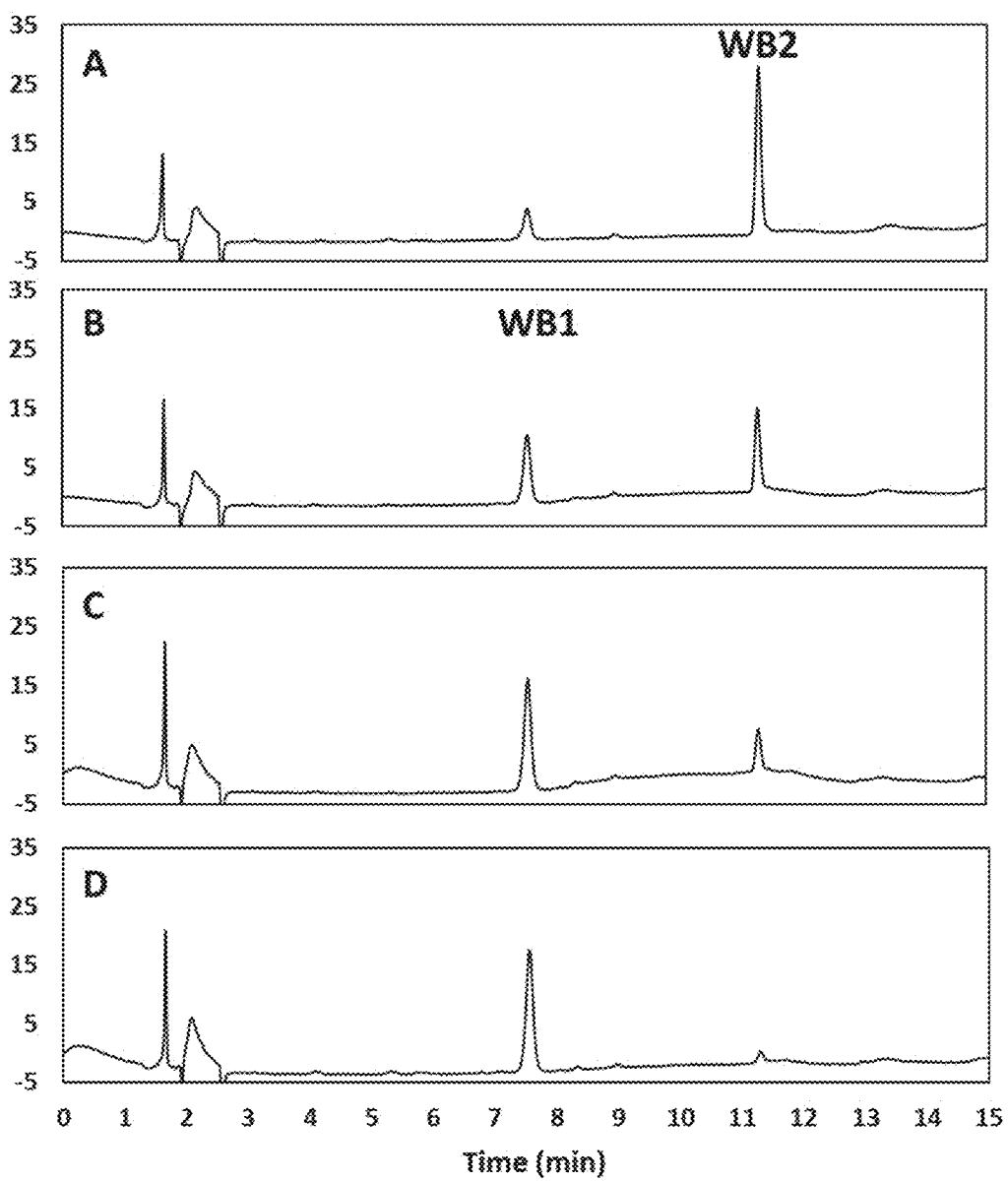
FIG. 4. Shows the HPLC profile of the bioconversion of rebaudioside WB2 ("WB2") to rebaudioside WB1 ("WB1") by UGT85C2. Rebaudioside WB2 was incubated with UGT85C2 enzyme at 0 hour (A), 2 hours (B), 6 hours (C) and 18 hours (D).
Figure 5A:
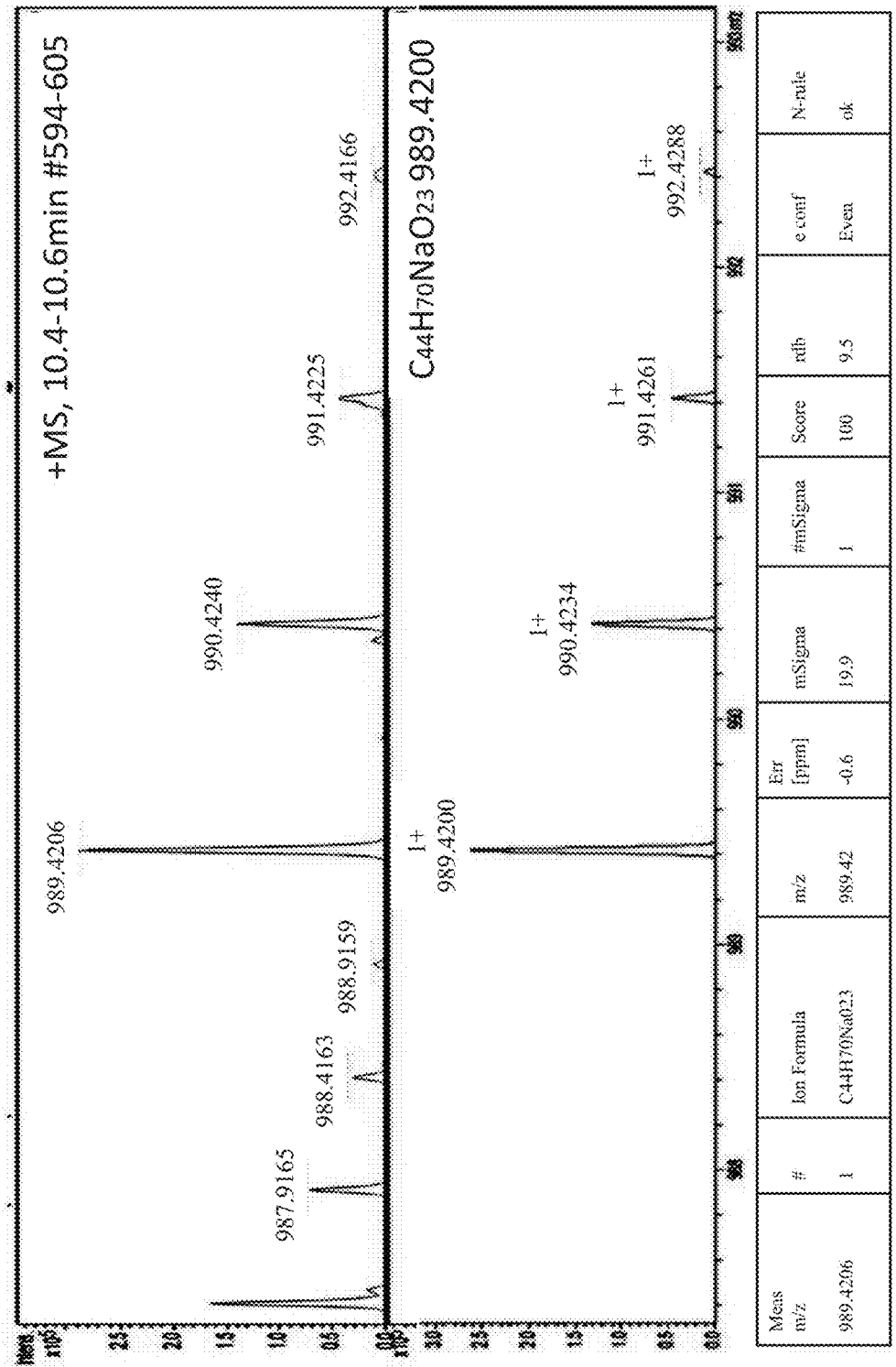
FIG. 5A. Shows the LC-MS analysis of rebaudioside WB1 and WB2.
Figure 5B:
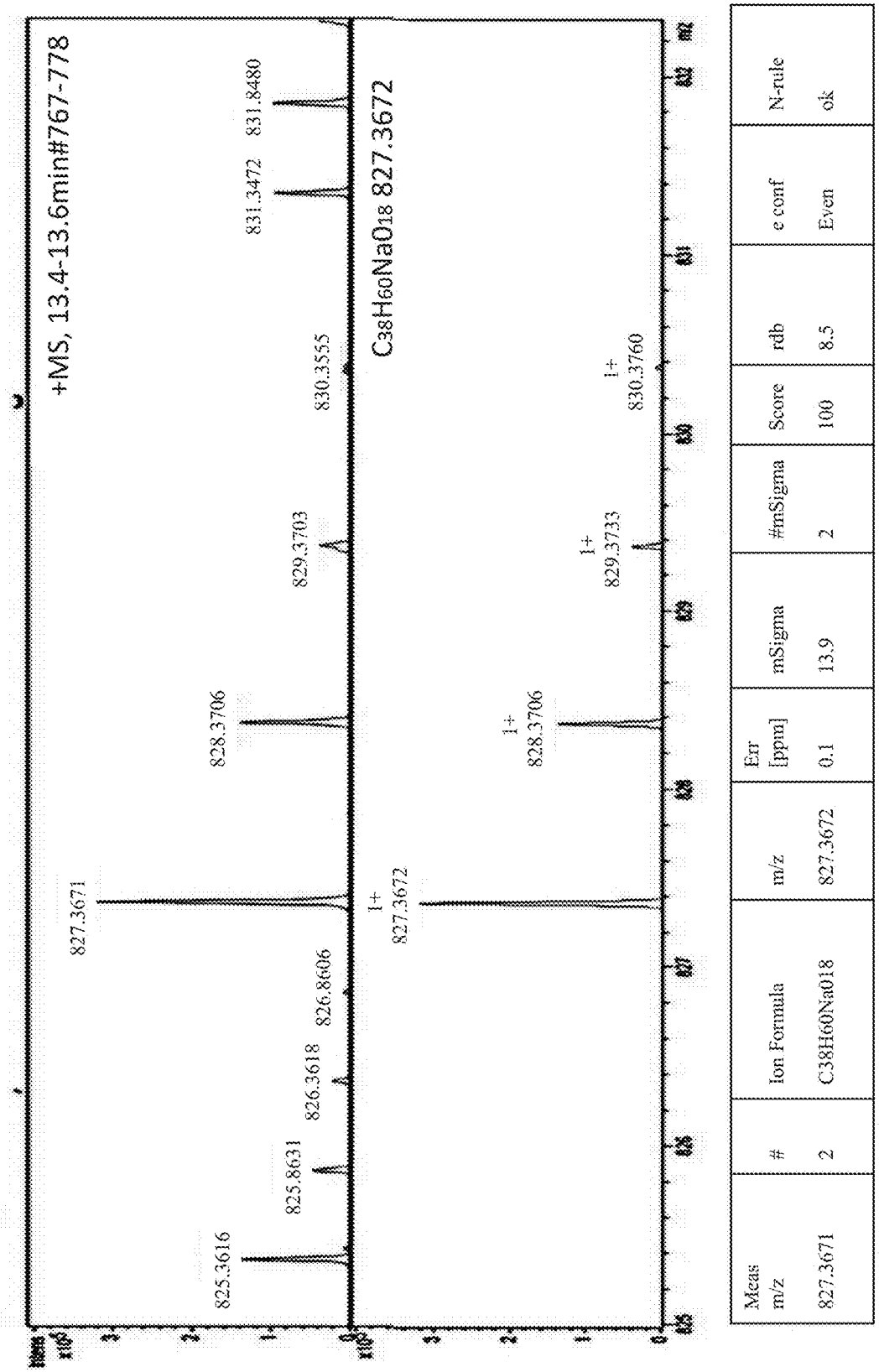
FIG. 5B. Shows the LC-MS analysis of rebaudioside WB1 and WB2.

The above intermediate rebaudioside WB2 can be converted back to rebaudioside WB1 by incubating with UGT85C2 enzyme (FIG. 4). The recombinant UGT85C2 enzyme (10 µg) was tested in a 200 µL in vitro reaction system. The reaction system contained 50 mM potassium phosphate buffer, pH 7.2, 3 mM MgCl2, 0.5 mg/ml rebaudioside WB2 substrate, and 3 mM UDP-glucose. As shown in FIG. 3, rebaudioside WB2 can be converted to rebaudioside WB1 by UGT85C2 (SEQ ID NO: 7, FIG. 4). UGT85C2 enzyme has activity to form steviol-13-monoside from steviol adding a glucose to C-13 of C4 carboxyl. These results indicated that B-glu1 hydrolyzed a glucose from C13 position of rebaudioside WB1 to produce rebaudioside WB2. The predicted structures of rebaudioside WB1 and rebaudioside WB2 are shown in FIG. 2. The structures were confirmed by LC-MS analysis (FIG. 5).

Figure 6:
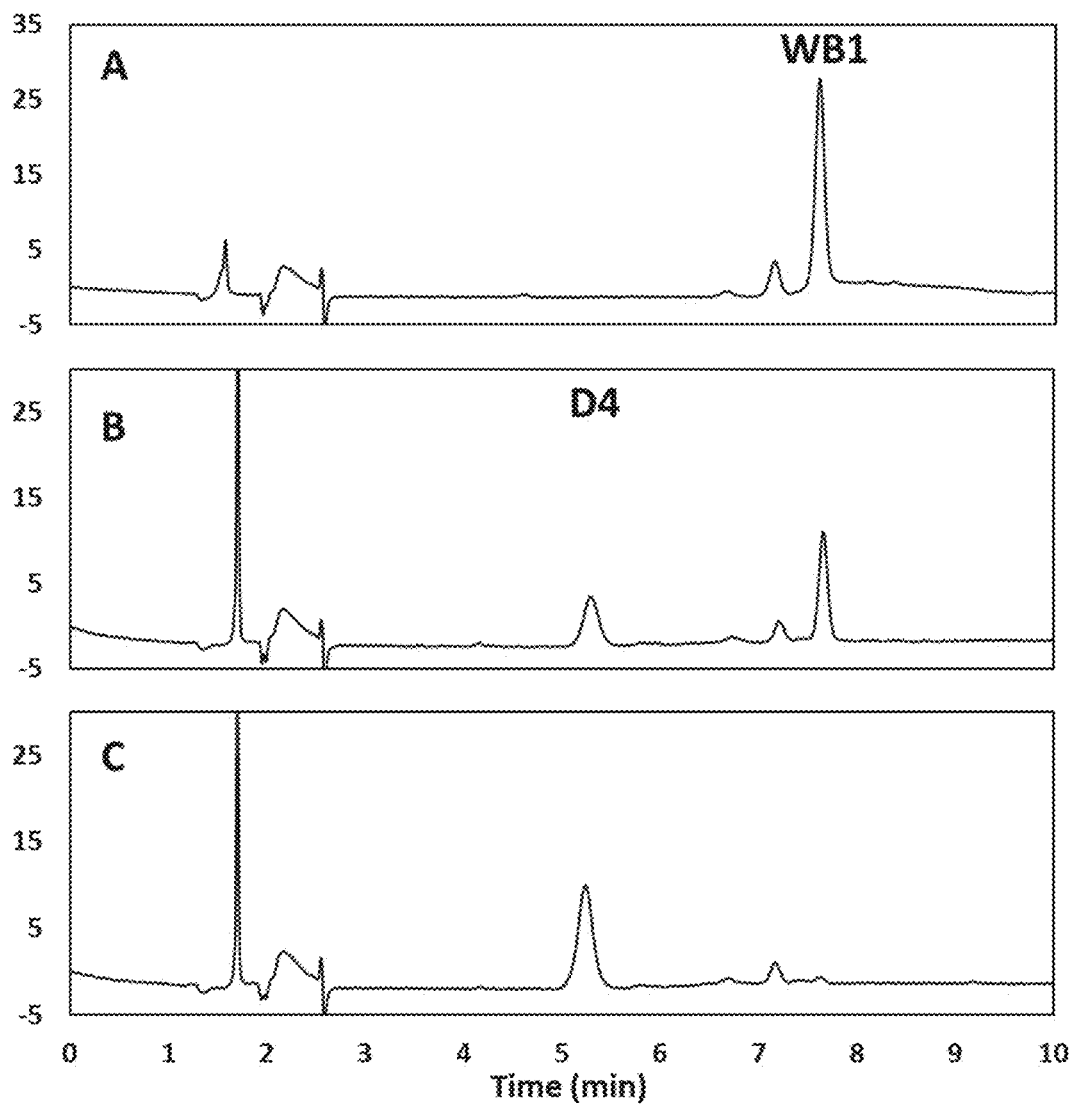
FIG. 6. Shows the HPLC profiles of the bioconversion of rebaudioside WB1 to rebaudioside D4 by HV1 enzyme. A: Standard of rebaudioside WB1 ("WB1"); B-C: Rebaudioside WB1 was converted by HV1 enzyme at 2 hours (B) and 6 hours (C).

The above intermediate Reb WB1 can be converted to Reb D4 by incubating with HV1 UGT enzyme (WO/2015/065650). The recombinant HV1 (10 µg) was tested in a 200 µL in vitro reaction system. The reaction system contained 50 mM potassium phosphate buffer, pH 7.2, 3 mM MgCl2, 0.5 mg/ml rebaudioside WB1 substrate, and 3 mM UDP-glucose. As shown in FIG. 4, rebaudioside WB1 can be converted to rebaudioside D4 by HV1 completely at 6 hours (FIG. 6 C).

Figure 7A:
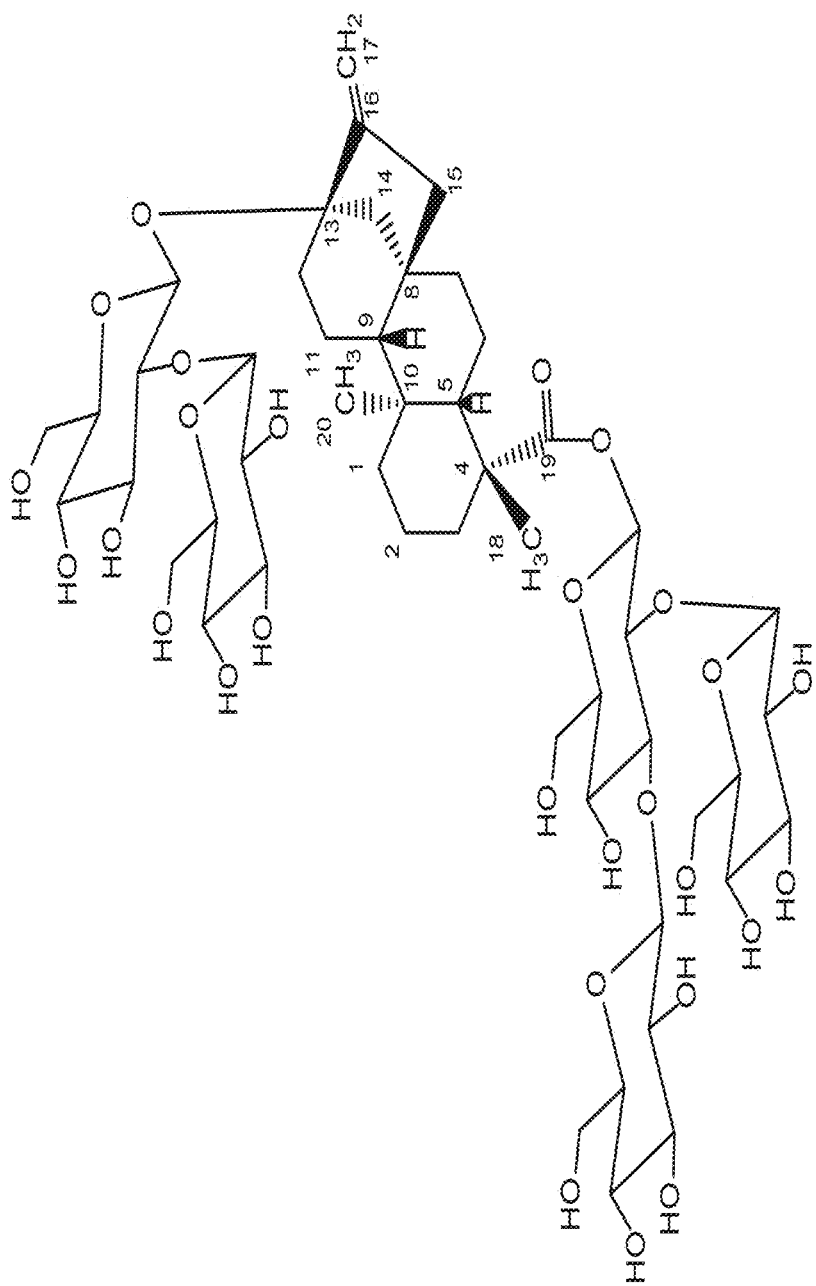
FIGS. 7A and 7B. Shows the structure and LC-MS data around the Reb D4 molecule.
Figure 7B:
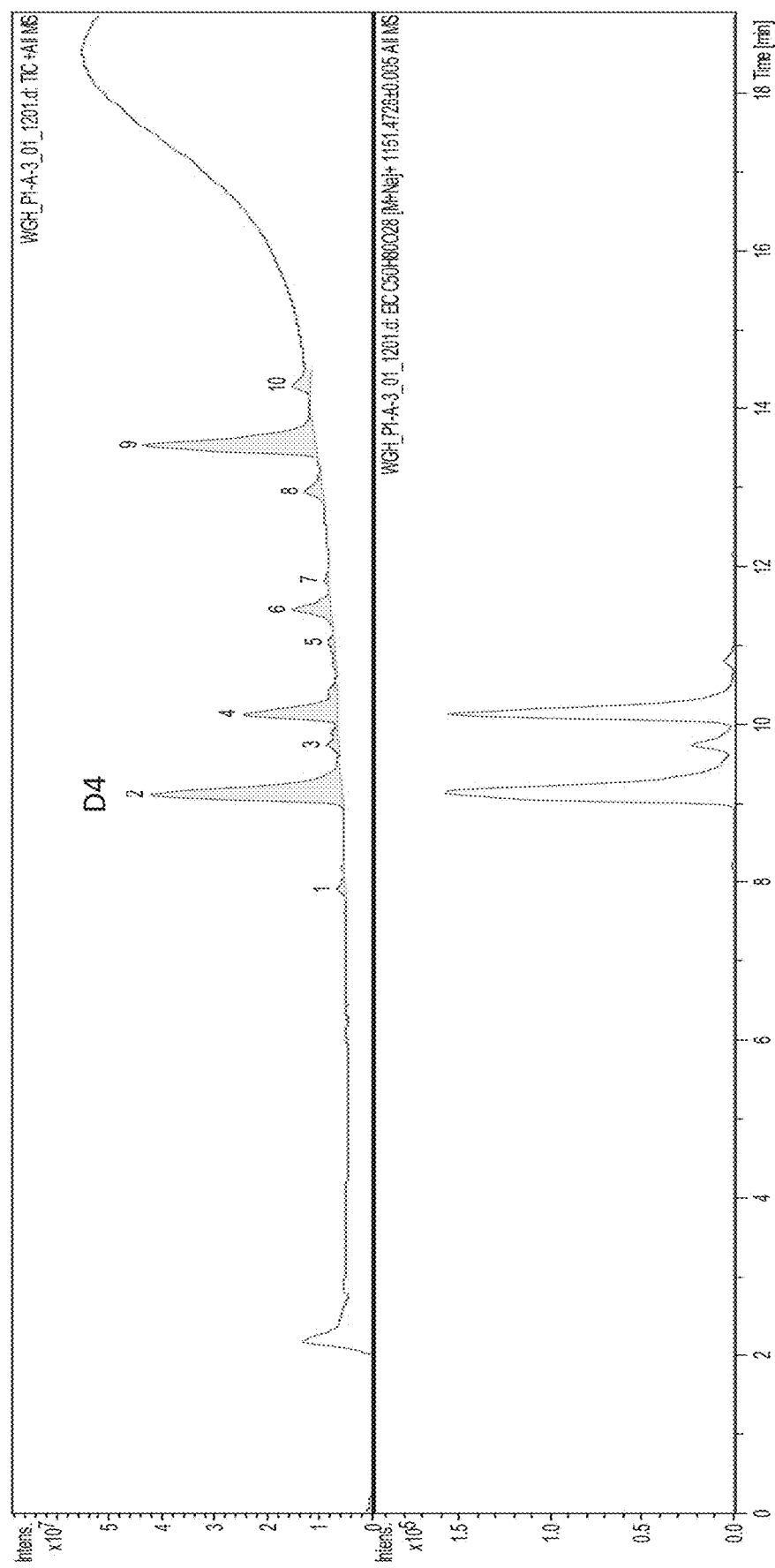
Figure 7B:
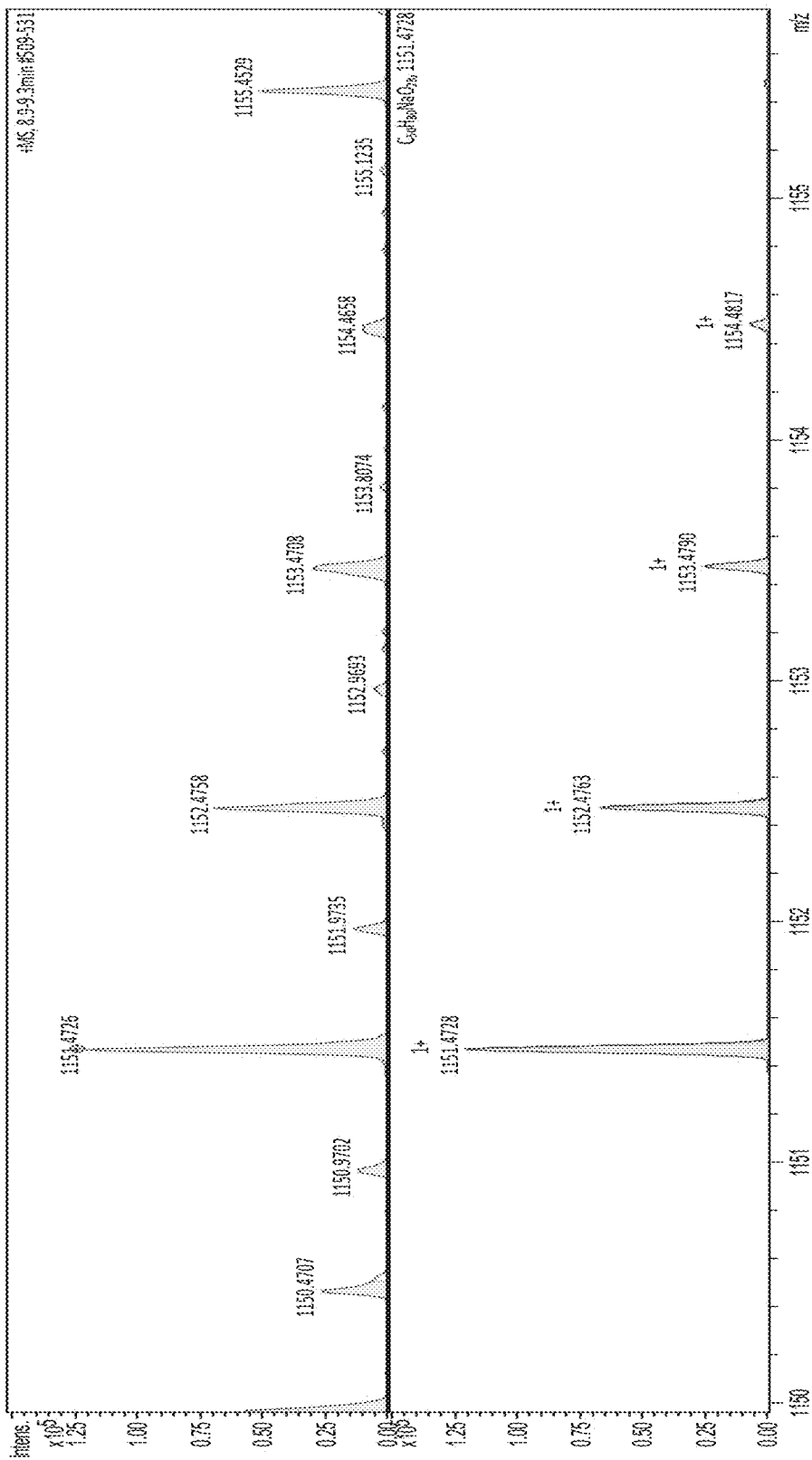

According to above enzymatic reactions, the structure of D4 was predicted as (13-[(2-O-β-D-glucopyranosyl-β-D-glucopyranosyl)oxy] ent-kaur-16-en-19-oic acid-[(2-O-β-D-glucopyranosyl-3-O-β-D-glucopyranosyl-β-D-glucopyranosyl) ester] (FIG. 7 A). The structure of Reb D4 was confirmed by LC-MS (FIG. 7 B). Mass spectral analysis showed the same mass [(M+Na) 1151.47 m/z] as the predicated structure.

Example 2: Converting Reb D4 to Reb M by Wild Type Enzyme

We discovered that the Reb D4 can be further converted to Reb M by UGT76G1. The full-length DNA fragments of UGT76G1 (SEQ ID NO: 2) was synthesized. The cDNA was codon optimized for E. coli expression (Genscript). The synthesized DNA was cloned into a bacterial expression vector pETite N-His SUMO Kan Vector (Lucigen). The nucleotide sequence encoding the 76G1 was inserted in frame.

The expression construct was transformed into E. coli BL21 (DE3), which was subsequently grown in LB media containing 50 µg/mL kanamycin at 37° C. until reaching an OD600 of 0.8-1.0. Protein expression was induced by addition of 0.5 mM IPTG and the culture was further grown at 16° C. for 22 hr. Cells were harvested by centrifugation (3,000×g; 10 min; 4° C.). The cell pellets were collected and were either used immediately or stored at −80° C.

The cell pellets were re-suspended in lysis buffer as described above. The cells were disrupted by sonication at 4° C., and the cell debris was clarified by centrifugation (18,000×g; 30 min). The supernatant was loaded to an equilibrated Ni-NTA (Qiagen) affinity column as described above. After loading of protein sample, the column was washed with equilibration buffer to remove unbound contaminant proteins. The His-tagged 76G1 recombinant polypeptide was eluted by equilibration buffer containing 250 mM imidazole.

The recombinant UGT76G1 (10 µg) was added in a 200 µL in vitro reaction system. The reaction system contained 50 mM potassium phosphate buffer, pH 7.2, 1 mM UDPG as co-factor, and 1 mg/ml Reb D4 as the substrate. The reaction was performed at 37° C. and terminated by adding 200 µL of 1-butanol. The samples were extracted three times with 200 µL of 1-butanol. The pooled fraction was dried and dissolved in 70 µL of 80% methanol for high-performance liquid chromatography (HPLC) analysis.

HPLC analysis was performed using a Dionex UPLC ultimate 3000 system, including a quaternary pump, a temperature controlled column compartment, an auto sampler and a UV absorbance detector. Synergi Hydro-RP column with guard column was used for the characterization of steviol glycosides. Acetonitrile in water was used for elution in HPLC analysis. The detection wavelength was 210 nm.

Figure 13:
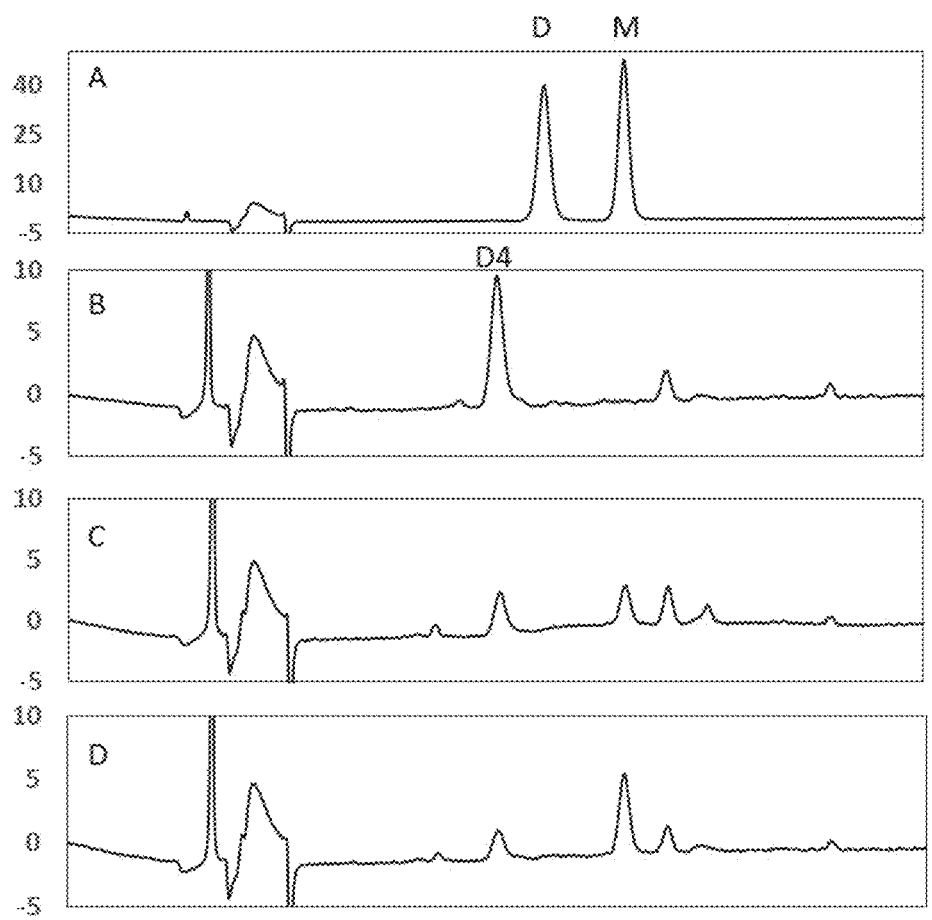
FIG. 13. Shows the in vitro production of Reb M from Reb D4 catalyzed by a combination of a recombinant UGT76G1 polypeptide, a recombinant CP1, and a mutant (CR1). A: show the standards of rebaudioside D ("D") and rebaudioside M ("M"). B: show the standard of rebaudioside D4 ("D4"). Reb M enzymatically produced by UGT76G1 at 30 min (C) and 1 hr (F), Reb M enzymatically produced by CP1 at 30 min (D) and 1 hr (G). Reb M enzymatically produced by CR1 at 30 min (E) and 1 hr (H).
Figure 13:
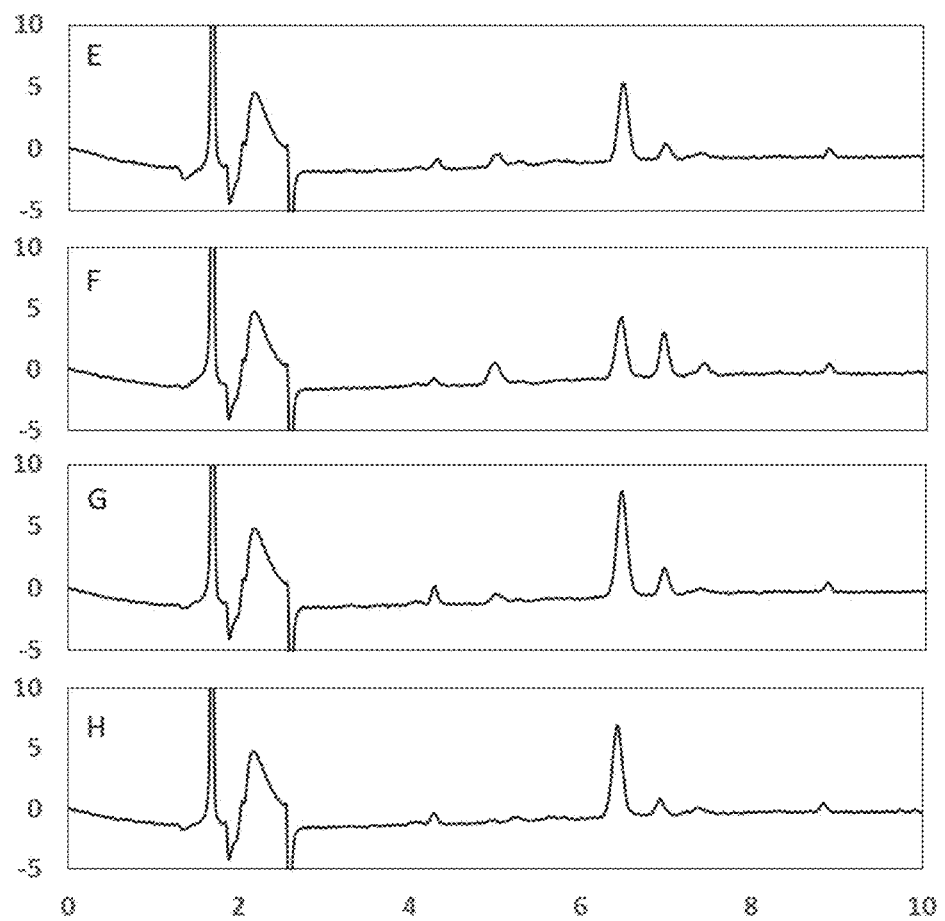

As shown in FIG. 13, UGT76G1 can convert Reb D4 to Reb M (FIGS. 13 C; and F).

Example 3: Resolving the Reaction Centers of UGT Enzymes Catalyzing Reb D4 to Reb M To more efficiently determine the chemical processes of the UDP-glucosyl transferase we obtained the crystal structure of a wild type steviol UDP-glucosyl transferase UGT76G1. This enzyme is the first reported enzyme that carry out steviol glycoside bio-conversions. We want to acquire the structural information of the reaction center and substrate binding sites to design enzymes for Reb D4 to Reb M conversion to understand it more completely and thereafter use this knowledge to find more efficiently find or design enzymes that can be useful in the Reb D4 to Reb M bioconversion.

For production of selenomethionine (SeMet)-substituted protein, Escherichia coli BL21 (DE3) cells were transformed with the pET-28a-UGT76G1 vector and grown in M9 minimal media supplemented with SeMet (Doublie, 2007) containing 50 ug mL-1 kanamycin at 37° C. (250 rpm) until A600 nm~0.8. Addition of isopropyl 1-thio-β-D-galactopyranoside (0.8 mM final) induced protein expression with cells grown overnight (16° C.). Cell pellets were harvested by centrifugation (10,000×g; 10 min) and suspended in lysis buffer (50 mM Tris, pH 8.0, 500 mM NaCl, 20 mM imidazole, 1 mM β-mercaptoethanol (β-ME), 10% (v/v) glycerol, and 1% (v/v) Tween-20). Following lysis by sonication, cell debris was removed by centrifugation (30,000× g; 45 min) and the supernatant passed over a Ni2+-nitriloacetic acid (NTA; Qiagen) column equilibrated with wash buffer (lysis buffer minus Tween-20). After loading, the column was washed with 10 column volumes of wash buffer. Bound fusion protein was eluted with elution buffer (wash buffer with 250 mM imidazole) and collected. For further purification, size-exclusion chromatography was performed on a Superdex-200 26/60 HiLoad FPLC column equilibrated with 50 mM Tris, pH 8.0, 25 mM NaCl, 1 mM tris(2-carboxyethyl) phosphine (TCEP). Peak fractions were collected and concentrated using centrifugal concentrators (Amicon) with protein concentration determined using the Bradford assay with bovine serum albumin as the standard. Purified protein was flash-frozen in liquid nitrogen and stored at −80° C.

Purified UGT761 was concentrated to 10 mg mL-1 and crystallized using the hanging-drop vapor-diffusion method with a 2 µl drop (1:1 concentrated protein and crystallization condition). Diffraction quality crystals were obtained at 4° C. with 20% (w/v) PEG-4000, 20% 2-propanol (v/v), and 100 mM sodium citrate tribasic dihydrate buffer (pH 5.6). Individual crystals were flash-frozen in liquid nitrogen with the mother liquor containing 25% glycerol as a cryoprotectant. Diffraction data (100 K) was collected at the Argonne National Laboratory Advanced Photon Source 19-ID beamline ($\lambda$=0.98 Å). HKL3000 (Otwinowski & Minor, 1997) was used to index, integrate, and scale diffraction data. The structure of SeMet-substituted UGT76G1 was determined by single-wavelength anomalous diffraction (SAD) phasing. SHELX (Sheldrick, 2008) was used to determine SeMet positions and to estimate initial phases from the peak wavelength data set. Refinement of SeMet positions and parameters was performed with MLPHARE (Terwilliger, 2000). Solvent flattening using density modification implemented with ARP/wARP (Morris et al., 2003) was employed to build an initial model. Subsequent iterative rounds of manual model building and refinement, which included translation-libration-screen parameter refinement, used COOT (Emsley et al., 2010) and PHENIX (Adams et al., 2007), respectively. Data collection and refinement data are summarized in Table 1.

TABLE 1

Summary of crystallographic statistics

| Data Collection | AtGH3.5•AMP•IAA |
|---|---|
| Space group | $P2_1$ |
| Cell dimensions | a = 91.61 Å, b = 143.5 Å, c = 102.3 Å; β = 114.7° |
| Wavelength (Å) | 0.979 |
| Resolution (Å) (highest shell) | 43.2-2.20 (2.25-2.20) |
| Reflections (total/unique) | 254,788/108,566 |
| Completeness (highest shell) | 89.5% (77.3%) |
| <I/σ> (highest shell) | 11.2 (2.0) |
| $R_{sym}$ (highest shell) | 9.3% (51.8%) |
| Refinement | |
| $R_{cryst}/R_{free}$ | 20.5%/24.5% |
| No. of protein atoms | 18,186 |
| No. of waters | 1,002 |
| No. of ligand atoms | 154 |
| R.m.s.d., bond lengths | 0.008 |
| R.m.s.d., bond angles (°) | 1.167 |
| Avg. B-factor (Å$^2$): protein, water ligand | 30.7, 28.3, 26.4 |
| Stereochemistry; most favored, allowed, disallowed | 97.3, 2.5, 0.2% |

Figure 8:
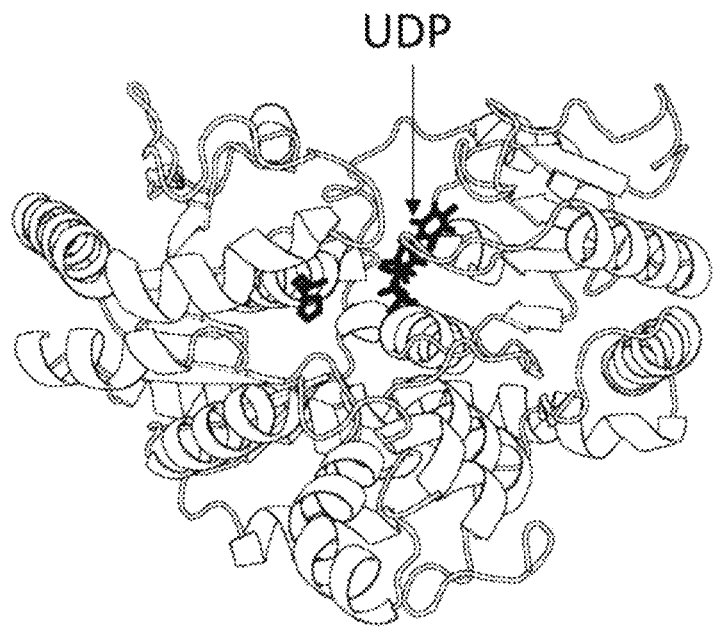
FIG. 8. Shows the structure of the UDP enzyme UGT71G1. The standard orientation with Histidine located on the left and UDP on the right is shown.
Figure 9:
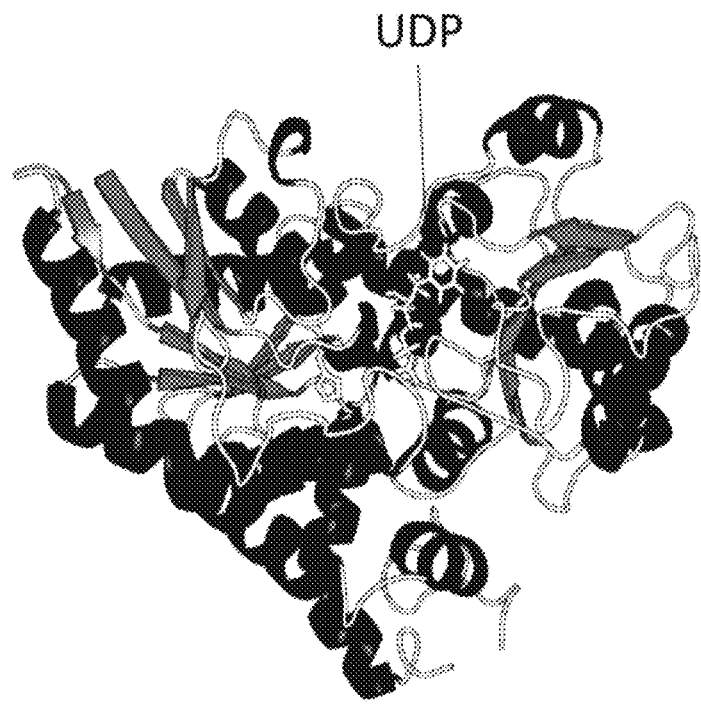
FIG. 9. Shows the structure of the UGT76G1 enzyme, highlighting the alpha helices and beta sheets in the UGT76G1 structure.

The structure of UGT71G1 consists of a N-terminal domain and C-terminal domain with similar Rossmann-type folds and, as predicted, belongs to the GT-B fold (FIG. 8). The standard orientation of the UGT76G1 crystal structure is shown in FIG. 8. The N-terminal domain contains a central seven-stranded parallel 13 sheet flanked by eight a helices. The domain also contains the catalytic histidine. The C-terminal domain contains a six-stranded 13 sheet flanked by seven a helices (FIG. 9). The two domains pack very tightly and form a deep cleft with a UDP molecule is bound.

Example 4: Rational Design of Mutants

Based on UGT76G1 structure, we were able to design the circular permutations (PLoS computational Biology, 2012, 8(3) e1002445; BIOINFORMATICS, 2015, (3) and a set of mutations. Circular permutation analysis is a powerful tool to develop useful or valuable enzymes. After test several version of circular permutations, we found one version of circular mutation with very high activity "circular permutation 1" ("CP1") has the highest activity. According to the current disclosure, we studied the activity of CP1 (SEQ ID NO: 3) enzyme and its ability to assist the conversions of Reb D4 to Reb M.

Figure 10:
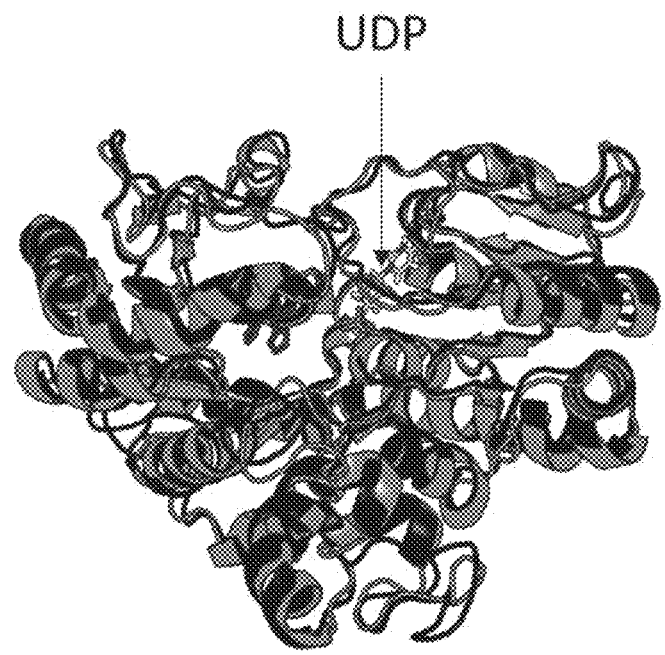
FIG. 10. Shows a comparison of the CP1 and UGT76G1 enzymes. The UGT76G1 crystal structure is colored gray, while the CP1 model is colored black.
Figure 11:
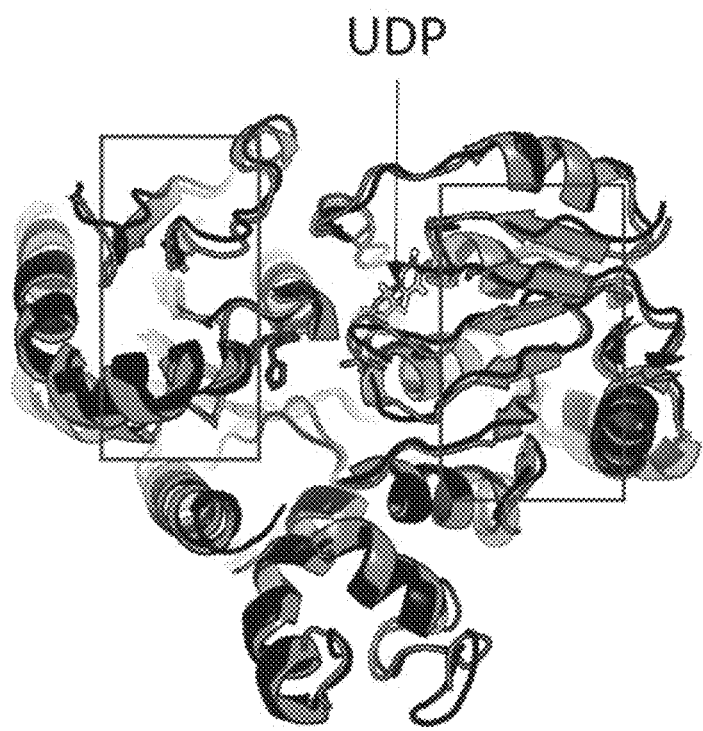
FIG. 11. Shows the UGT76G1 Crystal Structure and its interaction with the CP1 molecule. This crystal structure highlights the absence of beta sheets in the CP1 model. The UGT76G1 crystal structure is colored gray, while the CP1 model is colored black.

The structure of UGT76G1 and CP1 is compared in FIG. 10. Though the majority of the structural features of the UGT76G1 crystal structure are similar as between UGT and CP1 the CP1 has significantly different sequence and structure in the "beta sheets" portion of its structure (FIG. 11).

Figure 12:
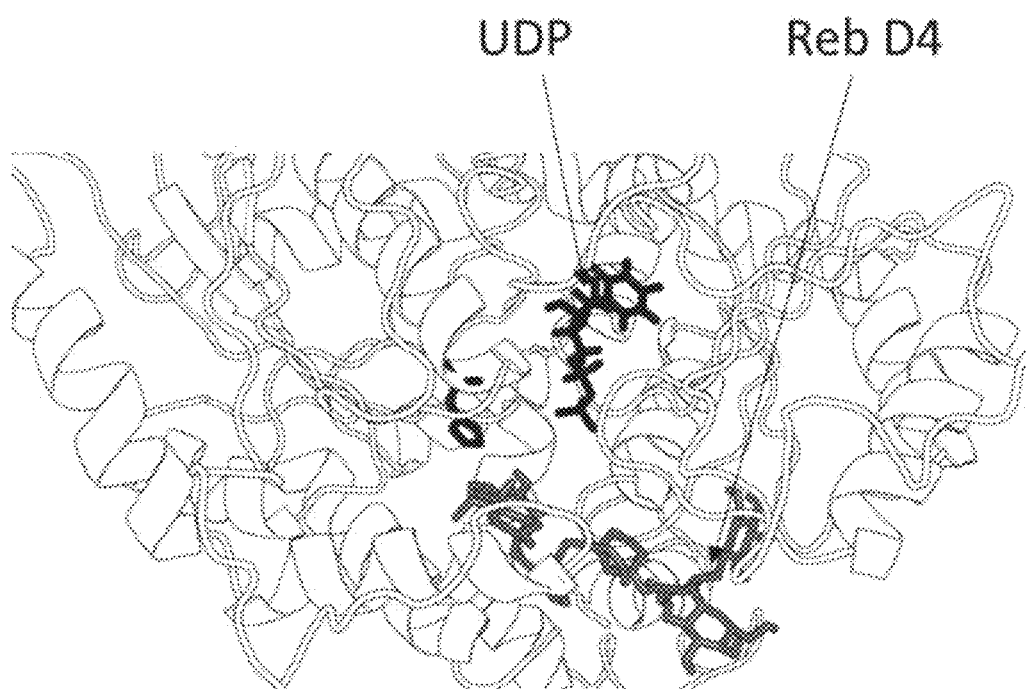
FIG. 12. Shows the Rebaudioside D4 in the reaction center of the enzyme CP1. The dark gray molecule located at the bottom of the image is rebaudioside D4.

In order to predict the catalytic activity of our enzymes, we docked the Reb D4 into the reaction center of CP1. We highlighted the reaction center focusing on the interactions of the enzyme with Reb D4. The docked rebaudioside D4 ligand is in a favorable position relative to the catalytic histidine and the bound UDP (FIG. 12). Based on this docking experiment, we were able to find specific residues worth testing activity via mutagenesis studies.

Based on the CP1 modeling analysis, we selected and tested multiple mutation sites of CP1 to increase enzymatic activity. Finally, we found several mutation sites (Table 2) related to bioconversion of rebaudioside D4 to rebaudioside M. CR1 is a kind of CP1 mutant includes at least one mutation site in the Table 2.

TABLE 2

Summary of mutation sites of CP1.

| Position | Amino acid |
|---|---|
| 3 | W-L |
| 6 | L-A, L-G |
| 90 | T-A, T-G |
| 91 | S-G, S-L |
| 93 | V-A, V-G |
| 181 | S-G |
| 183 | F-V; F-A; F-G |
| 184 | G-A |
| 185 | L-A |
| 350 | G-A |
| 389 | L-V |
| 410 | S-G |
| 418 | H-V |
| 450 | T-A; T-G |
| 451 | K-A |
| 452 | D-A |
| 454 | K-L; K-V |

Example 5: Converting Reb D4 to Reb M by Use of Mutant UGTs

In this Example, to confirm the conversion of Reb D4 to rebaudioside M in vitro, the UGT76G1, CP1 and enzyme mutants were assayed using Reb D4 as the steviol glycoside substrate. The recombinant polypeptide (10 μg) was tested in a 200 μL, in vitro reaction system. The reaction system contained 50 mM potassium phosphate buffer, pH 7.2, 3 mM $MgCl_2$, 1 mg/ml steviol glycoside substrate, and 1 mM UDP-glucose. The reaction was performed at 30° C. and terminated by adding 200 μL of 1-butanol. The samples were extracted three times with 200 μL of 1-butanol. The pooled fraction was dried and dissolved in 70 μL of 80% methanol for high-performance liquid chromatography (HPLC) analysis. Rebaudioside D4 were used as substrate. HPLC analysis was performed using a Dionex UPLC ultimate 3000 system (Sunnyvale, Calif.), including a quaternary pump, a temperature controlled column compartment, an auto sampler and a UV absorbance detector. Synergi Hydro-RP column with guard column was used for the characterization of steviol glycosides. Acetonitrile in water was used for elution in HPLC analysis. The detection wavelength was 210 nm.

As shown in FIG. 13, UGT76G1, CP1 and CR1 mutant can transfer one glucose molecule to Reb D4 to form Reb M. However, CP1 and CR1 has significantly higher enzymatic activity than UGT76G1 enzyme.

Example 6: The Structure of Reb WB2 Analyzed by NMR

The material used for the characterization of Reb WB2 was produced by using enzymatic conversion of Reb W and purified by HPLC. NMR spectra were acquired on Agilent VNMRS 500 MHz instrument instruments using standard pulse sequences. The 1D ($^1$H and $^{13}$C) and 2D (TOCSY, ASAPHMQC, GCOSY and GHMBC) NMR spectra were performed in CD3OD.

The molecular formula of Reb WB2 has been deduced as $C_{38}H_{60}O_{18}$ on the basis of its positive high resolution (HR) mass spectrum which showed adduct ions corresponding to [M+Na]$^+$ at m/z 827.3671; this composition was supported by the NMR spectral data.

The NMR spectral data of Reb WB2 revealed the basic skeleton of ent-kaurane diterpenoids and was further confirmed by the GHMBC, COSY and TOCSY experiments. Carbon multiplicities were confirmed using the APT test. The $^{13}$C NMR showed 3 anomeric carbons (δ 102.8, 101.7, and 92.46) as well as three —CH2OH signals at δ 62.2, 61.14 and 60.88 confirming the 3 sugar units. Also present were one carbonyl resonance at δ177.1 and two alkene carbons at δ 152.2 and 104.4. GHMBC correlations from H21 to C19 confirmed the attachment points of the sugars to the diterpenoid core structure. The Chemical shift of C13 at δ 79.4 indicates an oxygen attached to this carbon. The $^1$H and $^{13}$C NMR values for Reb WB2 were assigned on the basis of TOCSY, HMQC and HMBC data and are given in Table 3.

TABLE 3

$^1$H and $^{13}$C NMR spectral data (chemical shifts and coupling constants) for Reb WB2$^{a-c}$.

| C# | C13 δ | 1H δ (ppm), multp, J (Hz) |
|---|---|---|
| 1 | 40.3 | 1.89m/0.85 dt, J12.8, 4.0 |
| 2 | 19.0 | 1.96 m/1.43 m |
| 3 | 37.2 | 2.39 bd, J13.7/1.02 dd, J13.6, 4.2 |
| 4 | 43.8 | — |
| 5 | 57.2 | 1.09 dd, J10.6, 3.8 |
| 6 | 21.4 | 1.87 m |
| 7 | 41.3 | 1.56 m/1.45 m |
| 8 | 41.3 | — |
| 9 | 53.9 | 0.99 m |
| 10 | 39.2 | — |
| 11 | 39.2 | 1.76 m/1.47 m |
| 12 | 19.9 | 1.73 m/1.60 m |
| 13 | 79.4 | — |
| 14 | 46.2 | 2.05 s/1.30 m |
| 15 | 47.4 | 2.18 m/2.08 m |
| 16 | 155.5 | — |
| 17 | 102.1 | 4.95 s/4.78 s |
| 18 | 28.0 | 1.24 s |
| 19 | 176.1 | — |
| 20 | 15.5 | 0.92 s |
| 21 | 92.5 | 5.58 d, J8.1 |
| 22 | 77.0 | 3.43 m |
| 23 | 68.2 | 3.56 m |
| 24 | 86.6 | 3.86 m |
| 25 | 75.7 | 4.03 t, J8.5 |
| 26 | 60.9 | 3.83 dd, J12.7, 2.7/3.72 dd, J12.1, 4.6 |
| 27 | 102.8 | 4.69 d, J7.8 |
| 28 | 70.2 | 3.30 m |
| 29 | 74.0 | 3.28 m |
| 30 | 76.6 | 3.37 m |
| 31 | 76.8 | 3.38 m |
| 32 | 61.1 | 3.91 m/3.64 m |
| 33 | 101.7 | 5.01 d, J7.9 |
| 34 | 71.2 | 3.18 m |
| 35 | 76.7 | 3.36 m |
| 36 | 76.7 | 3.33 m |
| 37 | 74.4 | 3.12 m |
| 38 | 62.1 | 3.89 m/3.67 m |

$^a$assignments made on the basis of TOCSY, ASAPHMQC, and GHMBC correlations;
$^b$Chemical shift values are in δ (ppm);
$^c$Coupling constants are in Hz.

Figure 15:
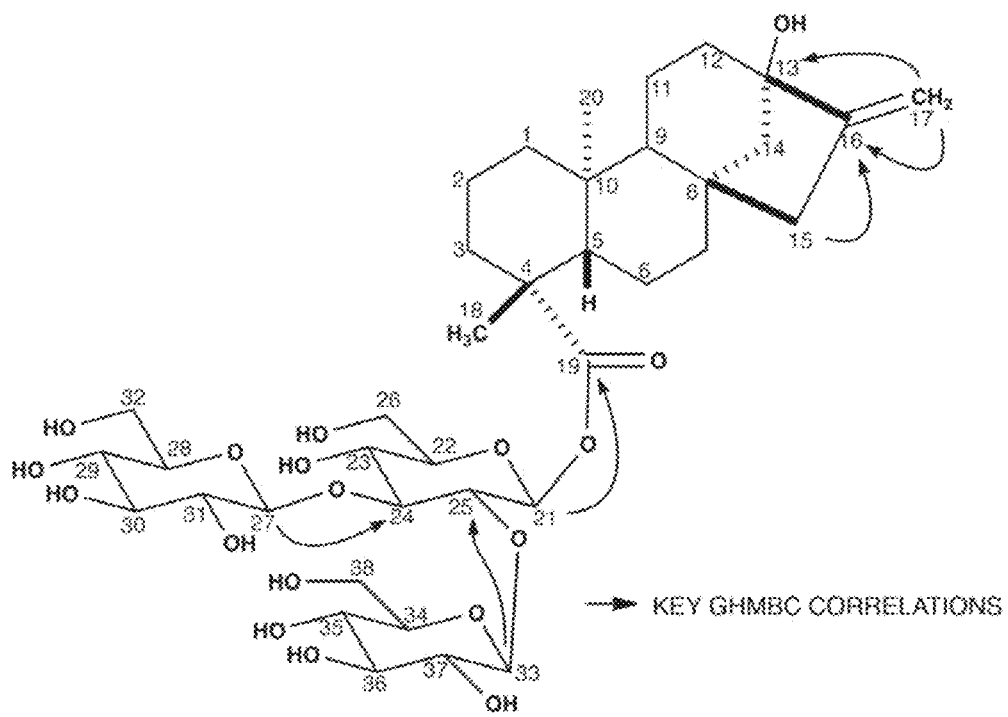
FIG. 15 Shows key GHMBC correlations of Reb WB2.

Key GHMBC correlations between H33 to C25, H27 to C24 confirmed the connectivity of the 3 sugar molecules. Based on all the observed 2D correlations and the chemical shift signals the structure of Reb WB2 as that shown in FIG. 15. The structure of Reb WB2 was deduced as 13-hydroxy-ent-kaur-16-en-19-oic acid-[(2-O-β-D-glucopyranosyl-3-O-β-D-glucopyranosyl-β-D-glucopyranosyl) ester.

Example 7: The Structure of Reb WB1 Analyzed by NMR

The material used for the characterization of Reb WB1 was produced by using enzymatic conversion of Reb W and purified by HPLC. NMR spectra were acquired on Agilent VNMRS 500 MHz instrument instruments using standard pulse sequences. The 1D ($^1$H and $^{13}$C) and 2D (TOCSY, ASAPHMQC, GCOSY and GHMBC) NMR spectra were performed in 80% CD3OD-20% D2O.

The molecular formula of Reb WB1 has been deduced as C44H70O23 on the basis of its positive high resolution (HR) mass spectrum which showed adduct ions corresponding to [M+Na]$^+$ at m/z 989.4206; this composition was supported by the NMR spectral data.

The NMR spectral data of Reb WB1 revealed the basic skeleton of ent-kaurane diterpenoids and was further confirmed by the GHMBC, COSY and TOCSY experiments. Carbon multiplicities were confirmed using the APT test. The $^{13}$C NMR showed 4 anomeric carbons (δ 102.6, 101.6 97.6 and 92.61 as well as four —CH2OH signals at δ 62.0, 61.1, 61.0 and 60.8 confirming the 4 sugar units. Also present were one carbonyl resonance at δ177.0 and two alkene carbons at δ 152.5 and 104.4. GHMBC correlations from H21 to C19 and H39 to C13 confirmed the attachment points of the sugars to the diterpenoid core structure. The $^1$H and $^{13}$C NMR values for Reb WB1 were assigned on the basis of TOCSY, HMQC and HMBC data and are given in Table 4.

TABLE 4

$^1$H and $^{13}$C NMR spectral data (chemical shifts and coupling constants) for Reb WB1$^{a-c}$.

| C# | C13 δ | 1H δ (ppm), multp, J (Hz) |
|---|---|---|
| 1 | 40.2 | 1.86 m/0.83 m |
| 2 | 19.0 | 1.93 m/1.41 m |
| 3 | 37.1 | 2.35 d, J 13.8/1.00 m |
| 4 | 44.0 | — |
| 5 | 51.1 | 1.09 m |
| 6 | 21.5 | 1.89 m |
| 7 | 41.1 | 1.57 m/1.44 m |
| 8 | 41.7 | — |
| 9 | 53.7 | 0.97 m |
| 10 | 39.2 | — |
| 11 | 19.9 | 1.81 m/1.62 m |
| 12 | 37.3 | 1.97 m/1.50 m |
| 13 | 86.7 | — |
| 14 | 43.9 | 2.18 m/1.54 m |
| 15 | 47.6 | 2.15 m/2.05 m |
| 16 | 152.5 | — |
| 17 | 104.4 | 5.17 s/4.88 s |
| 18 | 28.1 | 1.23 s |
| 19 | 177.0 | — |
| 20 | 15.5 | 0.91 s |
| 21 | 92.6 | 5.55d, J7.9 |
| 22 | 85.9 | 3.72 m |
| 23 | 68.2 | 3.57 m |
| 24 | 85.9 | 3.91 m |
| 25 | 75.9 | 4.05 m |
| 26 | 61.1 | 3.90 m/3.72 dd, J12.3, 4.7 |
| 27 | 102.6 | 4.72 d, J8.0 |
| 28 | 76.4 | 3.42 m |
| 29 | 76.6 | 3.45 m |
| 30 | 76.6 | 3.48 m |

TABLE 4-continued

¹H and ¹³C NMR spectral data (chemical shifts and coupling constants) for Reb WB1[a-c].

| C# | C13 δ | 1H δ (ppm), multp, J (Hz) |
|---|---|---|
| 31 | 70.0 | 3.34 m |
| 32 | 61.9 | 3.90 m/3.64 m |
| 33 | 101.6 | 4.96 m |
| 34 | 74.2 | 3.16 m |
| 35 | 76.5 | 3.43 m |
| 36 | 76.1 | 3.23 m |
| 37 | 73.8 | 3.30 m |
| 38 | 60.8 | 3.83 m/3.65 m |
| 39 | 97.6 | 4.54 d, J7.8 |
| 40 | 76.8 | 3.50 m |
| 41 | 73.8 | 3.31 m |
| 42 | 76.4 | 3.40 m |
| 43 | 71.0 | 3.21 m |
| 44 | 61.0 | 3.79 m/3.68 m |

[a]assignments made on the basis of TOCSY, ASAPHMQC, and GHMBC correlations;
[b]Chemical shift values are in δ (ppm);
[c]Coupling constants are in Hz.

Figure 16:
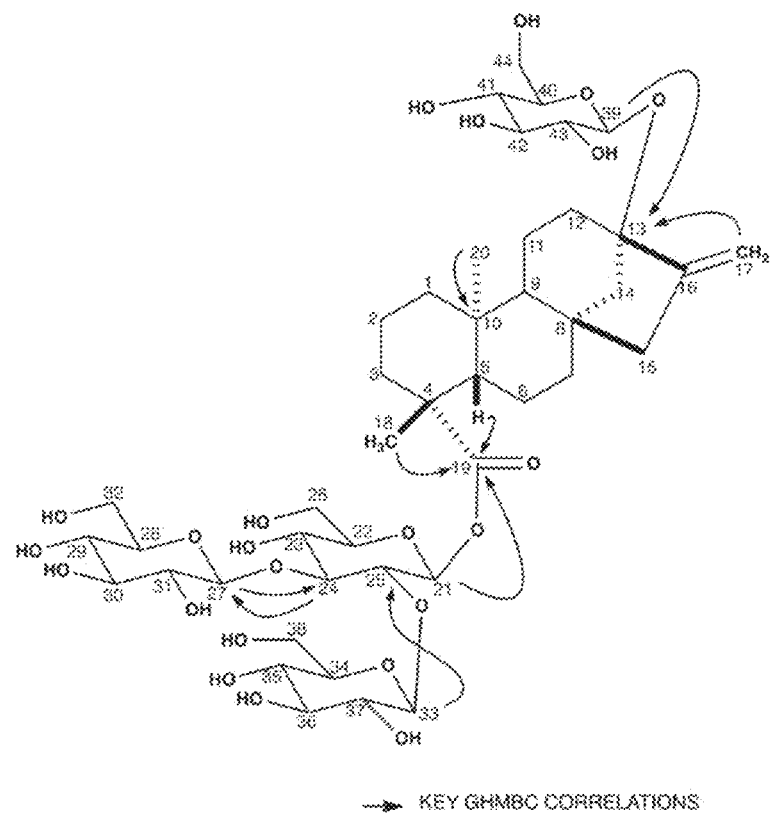
FIG. 16 Shows key GHMBC correlations of Reb WB1.

Other key GHMBC correlations between H33 to C25, H27 to C24 (and vice versa) confirmed the linkages of 3 of the sugar molecules. Based on all the observed 2D correlations and the chemical shift signals the structure of Reb WB1 as that shown in FIG. 16. The structure of Reb WB1 was deduced as 13-O-D-glucopyranosyloxy ent-kaur-16-en-19-oic acid-[(2-O-β-D-glucopyranosyl-3-O-β-D-glucopyranosyl-β-D-glucopyranosyl) ester.

Example 8: The Structure of Reb D4 Analyzed by NMR

The material used for the characterization of Reb D4 was produced by using enzymatic conversion of Reb WB1 and purified by HPLC. NMR spectra were acquired on Agilent VNMRS 500 MHz instrument instruments using standard pulse sequences. The 1D (¹H and ¹³C) and 2D (TOCSY, ASAPHMQC, GCOSY and GHMBC) NMR spectra were performed in 80% CD3OD and 20% D2O.

The molecular formula of Reb D4 has been deduced as $C_{50}H_{80}O_{28}$ on the basis of its positive high resolution (HR) mass spectrum which showed adduct ions corresponding to [M+Na]$^+$ at m/z 1151.4728; this composition was supported by the NMR spectral data.

The ¹H NMR spectral data of Reb D4 showed the presence of two methyl singlets at δ 1.24 and 0.92, two olefinic protons as singlets at δ 5.20 and 4.86 of an exocyclic double bond. The basic skeleton of ent-kaurane diterpenoids was supported by the GHMBC, COSY and TOCSY experiments. Carbon multiplicities were confirmed using the APT test. The ¹³C NMR showed 5 anomeric carbons (δ 103.5, 102.5, 101.8, 95.6 and 92.8) confirming the 5 sugar units, one carbonyl at δ177.1 and two alkene carbons at δ 152.2 and 104.4. GHMBC correlations from H40 to C12 and H22 to C19 confirmed the attachment points of the sugars to the diterpenoid core structure The ¹H and ¹³C NMR values for Reb D4 were assigned on the basis of TOCSY, HMQC and HMBC data and are given in Table 5.

TABLE 5

¹H and ¹³C NMR spectral data (chemical shifts and coupling constants) for Reb D4[a-c].

| C# | C13 δ | 1H δ (ppm), multp, J (Hz) |
|---|---|---|
| 1 | 19.0 | 1.94, m/1.44, m |
| 2 | 37.0 | 2.31, m/1.04, m |
| 3 | 43.9 | — |
| 4 | 57.0 | 1.07, m |
| 5 | 39.2 | — |
| 6 | 40.0 | 1.83, m/0.84, m |
| 7 | 21.9 | 1.89, m |
| 8 | 41.3 | 1.56, m/1.40, m |
| 9 | 41.3 | — |
| 10 | 53.6 | 0.97, m |
| 11 | 43.9 | 2.22, m/1.50, m |
| 12 | 87.2 | — |
| 13 | 37.0 | 1.99, m/1.53, m |
| 14 | 19.7 | 1.62, m |
| 15 | 46.7 | 2.14, m/2.04, m |
| 16 | 152.2 | — |
| 17 | 104.4 | 5.20, s/4.86, s |
| 18 | 27.9 | 1.24, s |
| 19 | 177.1 | — |
| 22 | 92.8 | 5.57, d, J7.6 Hz |
| 24 | 76.7 | 3.92, m |
| 25 | 63.4 | 3.53, m |
| 26 | 85.9 | 4.05, m |
| 27 | 75.9 | 4.01, m |
| 28 | 101.8 | 4.99, d, J7.9 Hz |
| 30 | 70.1 | 3.32, m |
| 31 | 71.1 | 3.21, m |
| 32 | 69.8 | 3.39, m |
| 33 | 70.6 | 3.18, m |
| 34 | 102.5 | 4.76, d, J7.9 Hz |
| 36 | 76.5 | 3.72, m |
| 37 | 74.6 | 3.25, m |
| 38 | 76.2 | 3.66, m |
| 39 | 73.8 | 3.34, m |
| 40 | 103.5 | 4.64, m |
| 42 | 76.9 | 3.69, m |
| 43 | 76.4 | 3.65, m |
| 44 | 76.6 | 3.42, m |
| 45 | 76.5 | 3.45, m |
| 46 | 95.6 | 4.64, m |
| 48 | 76.2 | 3.59, m |
| 49 | 74.4 | 3.30, m |
| 50 | 76.6 | 3.68, m |
| 51 | 80.5 | 3.48, m |
| 59 | 60.9 | 3.78, m |
| 61 | 61.0 | 3.86, m |
| 66 | 62.0 | 3.91, m |
| 74 | 61.8 | 3.84, m |
| 76 | 61.0 | 3.67, m |
| 78 | 15.9 | 0.92, s |

[a]assignments made on the basis of TOCSY, ASAPHMQC, and GHMBC correlations;
[b]Chemical shift values are in δ (ppm);
[c]Coupling constants are in Hz.

Figure 17:
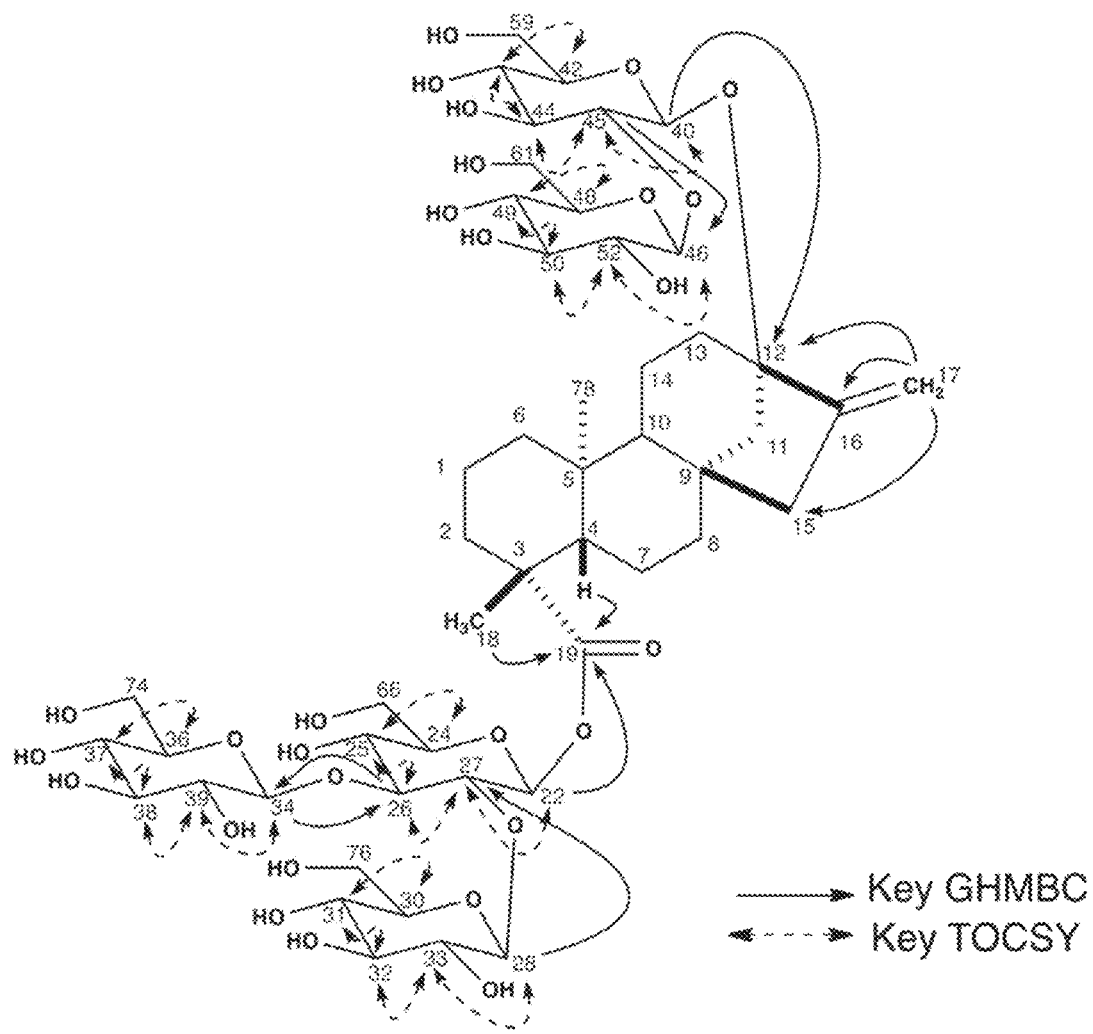
FIG. 17 Shows key TOCSY and GHMBC correlations of Reb D4.

Key GHMBC correlations between H45 to C46, H28 to C27 and H26 to C34 (and vice versa) confirmed the connectivity of the 5 sugar molecules. Based on all the observed 2D correlations and the chemical shift signals the structure of Reb D4 as that shown in FIG. 17. The structure of Reb D4 was deduced as 13-[(2-O-β-D-glucopyranosyl-β-D-glucopyranosyl)oxy] ent-kaur-16-en-19-oic acid-[(2-O-β-D-glucopyranosyl-3-O-β-D-glucopyranosyl-β-D-glucopyranosyl) ester.

Example 9: Taste Test of Rebaudiosides

A sensory evaluation of rebaudiosides was performed using sucrose as a control. The sucrose sample was purchased from Sigma-Aldrich and was used to prepared control samples at three different concentrations of 1.0%, 3.0%, and 6.0% sucrose in bottled water (w/v) at room temperature. The rebaudioside was prepared at 300 ppm for sensory evaluation by adding a corresponding mass into 1000 mL of bottled water. The mixture was stirred at room temperature and the steviol glycoside sample was then evaluated against several control sucrose samples at 1.0%, 3.0%, and 6.0% by a panel of 13 volunteer human subjects. The results of the sensory evaluation are shown in Table 6.

TABLE 6

Sensory evaluation of Reb W1, Reb W2 and Reb D4 compared to sucrose

| Rebaudioside | Fold increase in sweetness relative to sucrose |
|---|---|
| Reb WB1 | 133 |
| Reb WB2 | 79 |
| Reb D4 | 109 |

STATEMENT OF INDUSTRIAL APPLICABILITY/TECHNICAL FIELD

This disclosure has applicability in the food, feed, beverage, and pharmacological industries. This disclosure relates generally to a method for the biosynthetic production of steviol glycosides via a modified microbial strain.

LITERATURE CITED AND INCORPORATED BY REFERENCE

1. Brandle, J. E. et al., (1998). *Stevia Rebaudiana: Its Agricultural, Biological, and Chemical Properties*, CANADIAN J. PLANT SCIENCE. 78 (4): 527-36.
2. Ceunen, S., and J. M. C. Geuns, *Steviol Glycosides: Chemical Diversity, Metabolism, and Function*, J. NAT. PROD., 2013, 76 (6), pp 1201-28 (2013).
3. Du J et al., (2011), *Engineering microbial factories for synthesis of value-added products*, J IND MICROBIOL BIOTECHNOL. 38: 873-90.
4. Hausler A, and Münch T., (1997), *Microbial production of natural flavors*, ASM NEWS 63:551-59.
5. Prakash I., et al.; *Isolation and Characterization of a Novel Rebaudioside M Isomer from a Bioconversion Reaction of Rebaudioside A and NMR Comparison Studies of Rebaudioside M Isolated from Stevia rebaudiana Bertoni and Stevia rebaudiana Morita*, BIOMOLECULES, 2014 Jim; 4(2): 374-89. (Published online 2014 Mar. 31, 2014).
6. Prakash I., et al., *Development of Next Generation Stevia Sweetener: Rebaudioside M*, FOODS, 2014, 3:162-175.
7. Shockey J M. Et a., (2003), *Arabidopsis contains a large superfamily of acyl-activating enzymes: phylogenetic and biochemical analysis reveals a new class of acyl-coenzyme A synthetases*. PLANT PHYSIOL 132 1065-76.

The invention claimed is:

1. A recombinant cell transformed with a polynucleotide that encodes a mutant of an enzyme having the amino acid sequence of SEQ ID NO: 3, wherein the mutant comprises an amino acid sequence having at least 90% sequence identity to the amino acid sequence of SEQ ID NO: 3, comprises at least one mutation at an amino acid residue position corresponding to a position selected from 3, 6, 90, 91, 93, 181, 183, 184, 185, 350, 389, 410, 418, 450, 451, 452, and 454 of SEQ ID NO: 3, wherein the mutant is a UDP-glycosyltransferase capable of converting rebaudioside D4 having the structure:

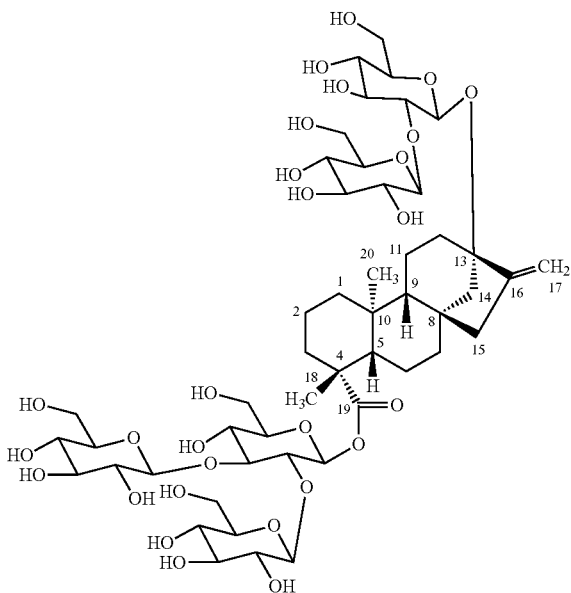

to rebaudioside M.

2. The recombinant cell of claim 1, wherein the cell is a yeast cell.

3. The recombinant cell of claim 1, wherein the cell is a bacterial cell.

4. The recombinant cell of claim 1, wherein the cell is a plant cell.

5. The recombinant cell of claim 1, wherein the mutant has at least one substitution selected from the group consisting of (i) W3L, (ii) L6A or L6G, (iii) T90A or T90G, (iv) S91G or S91L, (v) V93A or V93G, (vi) S181G, (vii) F183V, F183A, or F183G, (viii) G184A, (ix) L185A, (x) G350A, (xi) L389V, (xii) S410G, (xiii) H418V, (xiv) T450A or T450G, (xv) K451A, (xvi) D452A, and (xvii) K454L or K454V.

6. The recombinant cell of claim 1, wherein the mutant comprises a mutation at an amino acid residue position corresponding to position 3 of SEQ ID NO: 3.

7. The recombinant cell of claim 1, wherein the mutant comprises a mutation at an amino acid residue position corresponding to position 6 of SEQ ID NO: 3.

8. The recombinant cell of claim 1, wherein the mutant comprises a mutation at an amino acid residue position corresponding to position 90 of SEQ ID NO: 3.

9. The recombinant cell of claim 1, wherein the mutant comprises a mutation at an amino acid residue position corresponding to position 91 of SEQ ID NO: 3.

10. The recombinant cell of claim 1, wherein the mutant comprises a mutation at an amino acid residue position corresponding to position 93 of SEQ ID NO: 3.

11. The recombinant cell of claim 1, wherein the mutant comprises a mutation at an amino acid residue position corresponding to position 181 of SEQ ID NO: 3.

12. The recombinant cell of claim 1, wherein the mutant comprises a mutation at an amino acid residue position corresponding to position 183 of SEQ ID NO: 3.

13. The recombinant cell of claim 1, wherein the mutant comprises a mutation at an amino acid residue position corresponding to position 184 of SEQ ID NO: 3.

14. The recombinant cell of claim 1, wherein the mutant comprises a mutation at an amino acid residue position corresponding to position 185 of SEQ ID NO: 3.

15. The recombinant cell of claim 1, wherein the mutant comprises a mutation at an amino acid residue position corresponding to position 350 of SEQ ID NO: 3.

16. The recombinant cell of claim 1, wherein the mutant comprises a mutation at an amino acid residue position corresponding to position 389 of SEQ ID NO: 3.

17. The recombinant cell of claim 1, wherein the mutant comprises a mutation at an amino acid residue position corresponding to position 410 of SEQ ID NO: 3.

18. The recombinant cell of claim 1, wherein the mutant comprises a mutation at an amino acid residue position corresponding to position 418 of SEQ ID NO: 3.

19. The recombinant cell of claim 1, wherein the mutant comprises a mutation at an amino acid residue position corresponding to position 450 of SEQ ID NO: 3.

20. The recombinant cell of claim 1, wherein the mutant comprises a mutation at an amino acid residue position corresponding to position 451 of SEQ ID NO: 3.

21. The recombinant cell of claim 1, wherein the mutant comprises a mutation at an amino acid residue position corresponding to position 452 of SEQ ID NO: 3.

22. The recombinant cell of claim 1, wherein the mutant comprises a mutation at an amino acid residue position corresponding to position 454 of SEQ ID NO: 3.

23. The recombinant cell of claim 5, wherein the mutant has the substitution W3L.

24. The recombinant cell of claim 5, wherein the mutant has the substitution L6A.

25. The recombinant cell of claim 5, wherein the mutant has the substitution L6G.

26. The recombinant cell of claim 5, wherein the mutant has the substitution T90A.

27. The recombinant cell of claim 5, wherein the mutant has the substitution T90G.

28. The recombinant cell of claim 5, wherein the mutant has the substitution S91G.

29. The recombinant cell of claim 5, wherein the mutant has the substitution S91L.

30. The recombinant cell of claim 5, wherein the mutant has the substitution V93A.

31. The recombinant cell of claim 5, wherein the mutant has the substitution V93G.

32. The recombinant cell of claim 5, wherein the mutant has the substitution S181G.

33. The recombinant cell of claim 5, wherein the mutant has the substitution F183V.

34. The recombinant cell of claim 5, wherein the mutant has the substitution F183A.

35. The recombinant cell of claim 5, wherein the mutant has the substitution F183G.

36. The recombinant cell of claim 5, wherein the mutant has the substitution G184A.

37. The recombinant cell of claim 5, wherein the mutant has the substitution L185A.

38. The recombinant cell of claim 5, wherein the mutant has the substitution G350A.

39. The recombinant cell of claim 5, wherein the mutant has the substitution L389V.

40. The recombinant cell of claim 5, wherein the mutant has the substitution S410G.

41. The recombinant cell of claim 5, wherein the mutant has the substitution H418V.

42. The recombinant cell of claim 5, wherein the mutant has the substitution T450A.

43. The recombinant cell of claim 5, wherein the mutant has the substitution T450G.

44. The recombinant cell of claim 5, wherein the mutant has the substitution K451A.

45. The recombinant cell of claim 5, wherein the mutant has the substitution D452A.

46. The recombinant cell of claim 5, wherein the mutant has the substitution K454L.

47. The recombinant cell of claim 5, wherein the mutant has the substitution K454V.

48. The recombinant cell of claim 1, wherein the mutant comprises an amino acid sequence having at least 95% sequence identity to the amino acid sequence of SEQ ID NO: 3.

49. The recombinant cell of claim 1, wherein the mutant comprises an amino acid sequence having at least 98% sequence identity to the amino acid sequence of SEQ ID NO: 3.

* * * * *

UNITED STATES PATENT AND TRADEMARK OFFICE
CERTIFICATE OF CORRECTION

PATENT NO. : 11,098,315 B2
APPLICATION NO. : 16/117652
DATED : August 24, 2021
INVENTOR(S) : Mao et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 145 days.

Signed and Sealed this
Twenty-ninth Day of November, 2022

Katherine Kelly Vidal
*Director of the United States Patent and Trademark Office*